US006767742B1

(12) United States Patent
Sukhapinda et al.

(10) Patent No.: US 6,767,742 B1
(45) Date of Patent: Jul. 27, 2004

(54) ANTIBODY-MEDIATED DOWN-REGULATION OF PLANT PROTEINS

(75) Inventors: Kitisri Sukhapinda, Zionsville, IN (US); James M. Hasler, Danville, IN (US); James K. Petell, Zionsville, IN (US); James A. Strickland, Goodlettsville, TN (US); Otto Folkerts, Guilford, CT (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/358,321

(22) Filed: Jul. 21, 1999

Related U.S. Application Data

(60) Provisional application No. 60/093,587, filed on Jul. 21, 1998.

(51) Int. Cl.[7] ........................... C12N 15/82; A01H 5/00

(52) U.S. Cl. ..................... 435/419; 435/320.1; 800/298

(58) Field of Search .............................. 435/320.1, 419, 435/468; 800/298, 278; 536/23.53

(56) References Cited

PUBLICATIONS

Whitelam et al, "Antibody production in transgenic plants", Nov. 1994, Biochem. Soc. Trans. vol. 22 No. 4, pp. 940–944.*

* cited by examiner

*Primary Examiner*—Phuong T. Bui
*Assistant Examiner*—Cynthia Collins
(74) *Attorney, Agent, or Firm*—Ronald S. Maciak; Donald R. Stuart

(57) ABSTRACT

Monoclonal antibodies expressed in plant cells bind targeted transit peptides to decrease steady state levels of passenger proteins in plant organelles.

3 Claims, No Drawings

SEQUENCE LISTING

```
<160> NUMBER OF SEQ ID NOS: 60

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence:5' primer
<221> NAME/KEY: unsure
<222> LOCATION: (12)
<223> OTHER INFORMATION: n can be a,t,g, or c in this degenerate primer

<400> SEQUENCE: 1

gargaraaym gncaygg                                                17


<210> SEQ ID NO 2
<211> LENGTH: 18
<212> TYPE: DNA
<213> ORGANISM: Artificial Sequence
<220> FEATURE:
```

-continued

```
<223> OTHER INFORMATION: Description of Artificial Sequence:3' primer
<221> NAME/KEY: unsure
<222> LOCATION: (7)
<223> OTHER INFORMATION: n can be a,t,g, or c in this degenerate primer

<400> SEQUENCE: 2

ytcrtgncky ttytcrtc                                                 18


<210> SEQ ID NO 3
<211> LENGTH: 276
<212> TYPE: DNA
<213> ORGANISM: Zea mays
<220> FEATURE:
<221> NAME/KEY: CDS
<222> LOCATION: (1)..(276)

<400> SEQUENCE: 3

gag gag aac agg cat ggt gat ctg ctc aac aag tat atg tac ctc act       48
Glu Glu Asn Arg His Gly Asp Leu Leu Asn Lys Tyr Met Tyr Leu Thr
  1               5                  10                  15

ggg agg gtg gat atg agg cag att gag aag aca att cag tat ctt att       96
Gly Arg Val Asp Met Arg Gln Ile Glu Lys Thr Ile Gln Tyr Leu Ile
             20                  25                  30

ggc tct gga atg gat cct agg act gag aat aat cct tat ctt ggt ttc      144
Gly Ser Gly Met Asp Pro Arg Thr Glu Asn Asn Pro Tyr Leu Gly Phe
         35                  40                  45

atc tac acc tcc ttc caa gag cgg gcg acc ttc atc tca cac ggg aac      192
Ile Tyr Thr Ser Phe Gln Glu Arg Ala Thr Phe Ile Ser His Gly Asn
     50                  55                  60

act gct cgt cac gcc aag gac ttt ggc gac tta aag ctt gca caa atc      240
Thr Ala Arg His Ala Lys Asp Phe Gly Asp Leu Lys Leu Ala Gln Ile
 65                  70                  75                  80

tgc ggc atc atc gcc tca gat gag aag cga cat gaa                      276
Cys Gly Ile Ile Ala Ser Asp Glu Lys Arg His Glu
                 85                  90


<210> SEQ ID NO 4
<211> LENGTH: 92
<212> TYPE: PRT
<213> ORGANISM: Zea mays

<400> SEQUENCE: 4

Glu Glu Asn Arg His Gly Asp Leu Leu Asn Lys Tyr Met Tyr Leu Thr
  1               5                  10                  15

Gly Arg Val Asp Met Arg Gln Ile Glu Lys Thr Ile Gln Tyr Leu Ile
             20                  25                  30

Gly Ser Gly Met Asp Pro Arg Thr Glu Asn Asn Pro Tyr Leu Gly Phe
         35                  40                  45

Ile Tyr Thr Ser Phe Gln Glu Arg Ala Thr Phe Ile Ser His Gly Asn
     50                  55                  60

Thr Ala Arg His Ala Lys Asp Phe Gly Asp Leu Lys Leu Ala Gln Ile
 65                  70                  75                  80

Cys Gly Ile Ile Ala Ser Asp Glu Lys Arg His Glu
                 85                  90


<210> SEQ ID NO 5
<211> LENGTH: 1621
<212> TYPE: DNA
<213> ORGANISM: Zea mays
<220> FEATURE:
<221> NAME/KEY: CDS
<222> LOCATION: (146)..(1324)
<221> NAME/KEY: mat_peptide
```

```
<222> LOCATION: (239)..(1324)

<400> SEQUENCE: 5

cgcacgcgcc ctctgccgct tgttcgttcc tcgcgctcgc caccaggcac caccacacac     60

atcccaatct cgcgagggca agcagcaggg tctgcggcgg cggcggcggc cgcgcttccg    120

gctccccttc ccattggcct ccacg atg gcg ctc cgc ctc aac gac gtc gcg      172
                            Met Ala Leu Arg Leu Asn Asp Val Ala
                                -30                 -25

ctc tgc ctc tcc ccg ccg ctc gcc gcc cgc cgc cgc cgc cgc agc agc      220
Leu Cys Leu Ser Pro Pro Leu Ala Ala Arg Arg Arg Arg Arg Ser Ser
        -20                 -15                 -10

ggc agg ttc gtc gcc gtc gcc tcc atg acg tcc gcc gtc tcc acc aag      268
Gly Arg Phe Val Ala Val Ala Ser Met Thr Ser Ala Val Ser Thr Lys
    -5              -1   1               5                  10

gtc gag aat aag aag cca ttt gct cct cca agg gag gta cat gtc cag      316
Val Glu Asn Lys Lys Pro Phe Ala Pro Pro Arg Glu Val His Val Gln
                15                  20                  25

gtt aca cat tca atg cca cct cac aag att gaa att ttc aag tcg ctt      364
Val Thr His Ser Met Pro Pro His Lys Ile Glu Ile Phe Lys Ser Leu
            30                  35                  40

gat gat tgg gct aga gat aat atc ttg acg cat ctc aag cca gtc gag      412
Asp Asp Trp Ala Arg Asp Asn Ile Leu Thr His Leu Lys Pro Val Glu
        45                  50                  55

aag tgt tgg cag cca cag gat ttc ctc ccg gac cca gca tct gaa gga      460
Lys Cys Trp Gln Pro Gln Asp Phe Leu Pro Asp Pro Ala Ser Glu Gly
    60                  65                  70

ttt cat gat gaa gtt aag gag ctc aga gaa cgt gcc aag gaa atc cct      508
Phe His Asp Glu Val Lys Glu Leu Arg Glu Arg Ala Lys Glu Ile Pro
 75                  80                  85                  90

gat gat tat ttt gtt tgt ttg gtg gga gac atg att acc gag gaa gct      556
Asp Asp Tyr Phe Val Cys Leu Val Gly Asp Met Ile Thr Glu Glu Ala
                95                 100                 105

cta cca aca tac cag act atg ctt aac acc ctc gac ggt gtc aga gat      604
Leu Pro Thr Tyr Gln Thr Met Leu Asn Thr Leu Asp Gly Val Arg Asp
            110                 115                 120

gag aca ggt gca agc ccc act gcc tgg gct gtt tgg acg agg gca tgg      652
Glu Thr Gly Ala Ser Pro Thr Ala Trp Ala Val Trp Thr Arg Ala Trp
        125                 130                 135

act gct gag gag aac agg cat ggt gat ctg ctc aac aag tat atg tac      700
Thr Ala Glu Glu Asn Arg His Gly Asp Leu Leu Asn Lys Tyr Met Tyr
    140                 145                 150

ctc act ggg agg gtg gat atg agg cag att gag aag aca att cag tat      748
Leu Thr Gly Arg Val Asp Met Arg Gln Ile Glu Lys Thr Ile Gln Tyr
155                 160                 165                 170

ctt att ggc tct gga atg gat cct agg act gag aat aat cct tat ctt      796
Leu Ile Gly Ser Gly Met Asp Pro Arg Thr Glu Asn Asn Pro Tyr Leu
                175                 180                 185

ggt ttc atc tac acc tcc ttc caa gag cgg gcg acc ttc atc tca cac      844
Gly Phe Ile Tyr Thr Ser Phe Gln Glu Arg Ala Thr Phe Ile Ser His
            190                 195                 200

ggg aac act gct cgt cac gcc aag gac ttt ggc gac tta aag ctt gca      892
Gly Asn Thr Ala Arg His Ala Lys Asp Phe Gly Asp Leu Lys Leu Ala
        205                 210                 215

caa atc tgc ggc atc atc gcc tca gat gag aag cga cat gaa act gcg      940
Gln Ile Cys Gly Ile Ile Ala Ser Asp Glu Lys Arg His Glu Thr Ala
    220                 225                 230

tac acc aag atc gtg gag aag ctg ttt gag atc gac cct gat ggt acc      988
Tyr Thr Lys Ile Val Glu Lys Leu Phe Glu Ile Asp Pro Asp Gly Thr
235                 240                 245                 250
```

-continued

```
gtg gtc gct ctg gct gac atg atg agg aag aag atc tca atg cct gcc     1036
Val Val Ala Leu Ala Asp Met Met Arg Lys Lys Ile Ser Met Pro Ala
                255                 260                 265

cac ctg atg ttt gac ggg cag gac gac aag ctg ttc gag cac ttc tcc     1084
His Leu Met Phe Asp Gly Gln Asp Asp Lys Leu Phe Glu His Phe Ser
            270                 275                 280

atg gtc gcg cag agg ctt ggc gtt tac acc gcc agg gac tac gcc gac     1132
Met Val Ala Gln Arg Leu Gly Val Tyr Thr Ala Arg Asp Tyr Ala Asp
        285                 290                 295

atc ctc gag ttc ctc gtc gac agg tgg aag gtg gcg agc ctg act ggt     1180
Ile Leu Glu Phe Leu Val Asp Arg Trp Lys Val Ala Ser Leu Thr Gly
    300                 305                 310

ctg tcg ggt gaa ggg aac aag gcg cag gac tac ctt tgc acc ctt gct     1228
Leu Ser Gly Glu Gly Asn Lys Ala Gln Asp Tyr Leu Cys Thr Leu Ala
315                 320                 325                 330

tca aga atc agg agg ctg gag gag agg gcc cag agc aga gcc aag aaa     1276
Ser Arg Ile Arg Arg Leu Glu Glu Arg Ala Gln Ser Arg Ala Lys Lys
                335                 340                 345

gcc ggc acg ctg cct ttc agc tgg gta tac ggt agg gac gtc caa ctg     1324
Ala Gly Thr Leu Pro Phe Ser Trp Val Tyr Gly Arg Asp Val Gln Leu
            350                 355                 360

tgagatcgga acctgctgc ggactgctta gacaagacct gctgtgtctg cgttacatag   1384

gtctccaggt tttgatcaaa tggtcccgtg tcgtcttata gagcgatagg agaacgtgtt   1444

ggtctgtggt gtagctttgt ttttattttg tatttttctg ctttgatgta caacctgtgg   1504

ccgcatgaac tggggcgtgg agatgggagc gaccatgccg tactttgtct gtcgctggcg   1564

gtgtgtttcg gtatgttatt tgagttgctc agatctgtta aaaaaaaaaa aaaaaaa      1621


<210> SEQ ID NO 6
<211> LENGTH: 393
<212> TYPE: PRT
<213> ORGANISM: Zea mays

<400> SEQUENCE: 6

Met Ala Leu Arg Leu Asn Asp Val Ala Leu Cys Leu Ser Pro Pro Leu
    -30                 -25                 -20

Ala Ala Arg Arg Arg Arg Arg Ser Ser Gly Arg Phe Val Ala Val Ala
-15                 -10                  -5              -1   1

Ser Met Thr Ser Ala Val Ser Thr Lys Val Glu Asn Lys Lys Pro Phe
              5                  10                  15

Ala Pro Pro Arg Glu Val His Val Gln Val Thr His Ser Met Pro Pro
         20                  25                  30

His Lys Ile Glu Ile Phe Lys Ser Leu Asp Asp Trp Ala Arg Asp Asn
     35                  40                  45

Ile Leu Thr His Leu Lys Pro Val Glu Lys Cys Trp Gln Pro Gln Asp
 50                  55                  60                  65

Phe Leu Pro Asp Pro Ala Ser Glu Gly Phe His Asp Glu Val Lys Glu
                 70                  75                  80

Leu Arg Glu Arg Ala Lys Glu Ile Pro Asp Asp Tyr Phe Val Cys Leu
             85                  90                  95

Val Gly Asp Met Ile Thr Glu Glu Ala Leu Pro Thr Tyr Gln Thr Met
        100                 105                 110

Leu Asn Thr Leu Asp Gly Val Arg Asp Glu Thr Gly Ala Ser Pro Thr
    115                 120                 125

Ala Trp Ala Val Trp Thr Arg Ala Trp Thr Ala Glu Glu Asn Arg His
130                 135                 140                 145
```

-continued

```
Gly Asp Leu Leu Asn Lys Tyr Met Tyr Leu Thr Gly Arg Val Asp Met
                150                 155                 160

Arg Gln Ile Glu Lys Thr Ile Gln Tyr Leu Ile Gly Ser Gly Met Asp
            165                 170                 175

Pro Arg Thr Glu Asn Asn Pro Tyr Leu Gly Phe Ile Tyr Thr Ser Phe
        180                 185                 190

Gln Glu Arg Ala Thr Phe Ile Ser His Gly Asn Thr Ala Arg His Ala
    195                 200                 205

Lys Asp Phe Gly Asp Leu Lys Leu Ala Gln Ile Cys Gly Ile Ile Ala
210                 215                 220                 225

Ser Asp Glu Lys Arg His Glu Thr Ala Tyr Thr Lys Ile Val Glu Lys
                230                 235                 240

Leu Phe Glu Ile Asp Pro Asp Gly Thr Val Val Ala Leu Ala Asp Met
            245                 250                 255

Met Arg Lys Lys Ile Ser Met Pro Ala His Leu Met Phe Asp Gly Gln
        260                 265                 270

Asp Asp Lys Leu Phe Glu His Phe Ser Met Val Ala Gln Arg Leu Gly
    275                 280                 285

Val Tyr Thr Ala Arg Asp Tyr Ala Asp Ile Leu Glu Phe Leu Val Asp
290                 295                 300                 305

Arg Trp Lys Val Ala Ser Leu Thr Gly Leu Ser Gly Glu Gly Asn Lys
                310                 315                 320

Ala Gln Asp Tyr Leu Cys Thr Leu Ala Ser Arg Ile Arg Arg Leu Glu
            325                 330                 335

Glu Arg Ala Gln Ser Arg Ala Lys Lys Ala Gly Thr Leu Pro Phe Ser
        340                 345                 350

Trp Val Tyr Gly Arg Asp Val Gln Leu
    355                 360
```

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 7
atggctagcc tccgcctcaa cgacgtcgcg 30

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 8
aaagctagct catcacagtt ggacgtccct accgta 36

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 9
accatggcta gcatgacgtc cgccgtctcc 30

-continued

```
<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 10

gatgatgcta gctcacagtt ggacgtccct                                  30


<210> SEQ ID NO 11
<211> LENGTH: 1107
<212> TYPE: DNA
<213> ORGANISM: Zea mays
<220> FEATURE:
<221> NAME/KEY: CDS
<222> LOCATION: (4)..(1092)

<400> SEQUENCE: 11

acc atg gct acg atg acg tcc gcc gtc tcc acc aag gtc gag aat aag       48
    Met Ala Thr Met Thr Ser Ala Val Ser Thr Lys Val Glu Asn Lys
      1               5                  10                  15

aag cca ttt gct cct cca agg gag gta cat gtc cag gtt aca cat tca       96
Lys Pro Phe Ala Pro Pro Arg Glu Val His Val Gln Val Thr His Ser
                 20                  25                  30

atg cca cct cac aag att gaa att ttc aag tcg ctt gat gat tgg gct      144
Met Pro Pro His Lys Ile Glu Ile Phe Lys Ser Leu Asp Asp Trp Ala
             35                  40                  45

aga gat aat atc ttg acg cat ctc aag cca gtc gag aag tgt tgg cag      192
Arg Asp Asn Ile Leu Thr His Leu Lys Pro Val Glu Lys Cys Trp Gln
         50                  55                  60

cca cag gat ttc ctc ccg gac cca gca tct gaa gga ttt cat gat gaa      240
Pro Gln Asp Phe Leu Pro Asp Pro Ala Ser Glu Gly Phe His Asp Glu
     65                  70                  75

gtt aag gag ctc aga gaa cgt gcc aag gaa atc cct gat gat tat ttt      288
Val Lys Glu Leu Arg Glu Arg Ala Lys Glu Ile Pro Asp Asp Tyr Phe
 80                  85                  90                  95

gtt tgt ttg gtg gga gac atg att acc gag gaa gct cta cca aca tac      336
Val Cys Leu Val Gly Asp Met Ile Thr Glu Glu Ala Leu Pro Thr Tyr
                100                 105                 110

cag act atg ctt aac acc ctc gac ggt gtc aga gat gag aca ggt gca      384
Gln Thr Met Leu Asn Thr Leu Asp Gly Val Arg Asp Glu Thr Gly Ala
            115                 120                 125

agc ccc act gcc tgg gct gtt tgg acg agg gca tgg act gct gag gag      432
Ser Pro Thr Ala Trp Ala Val Trp Thr Arg Ala Trp Thr Ala Glu Glu
        130                 135                 140

aac agg cat ggt gat ctg ctc aac aag tat atg tac ctc act ggg agg      480
Asn Arg His Gly Asp Leu Leu Asn Lys Tyr Met Tyr Leu Thr Gly Arg
    145                 150                 155

gtg gat atg agg cag att gag aag aca att cag tat ctt att ggc tct      528
Val Asp Met Arg Gln Ile Glu Lys Thr Ile Gln Tyr Leu Ile Gly Ser
160                 165                 170                 175

gga atg gat cct agg act gag aat aat cct tat ctt ggt ttc atc tac      576
Gly Met Asp Pro Arg Thr Glu Asn Asn Pro Tyr Leu Gly Phe Ile Tyr
                180                 185                 190

acc tcc ttc caa gag cgg gcg acc ttc atc tca cac ggg aac act gct      624
Thr Ser Phe Gln Glu Arg Ala Thr Phe Ile Ser His Gly Asn Thr Ala
            195                 200                 205

cgt cac gcc aag gac ttt ggc gac tta aag ctt gca caa atc tgc ggc      672
Arg His Ala Lys Asp Phe Gly Asp Leu Lys Leu Ala Gln Ile Cys Gly
        210                 215                 220
```

-continued

```
atc atc gcc tca gat gag aag cga cat gaa act gcg tac acc aag atc      720
Ile Ile Ala Ser Asp Glu Lys Arg His Glu Thr Ala Tyr Thr Lys Ile
    225                 230                 235

gtg gag aag ctg ttt gag atc gac cct gat ggt acc gtg gtc gct ctg      768
Val Glu Lys Leu Phe Glu Ile Asp Pro Asp Gly Thr Val Val Ala Leu
240                 245                 250                 255

gct gac atg atg agg aag aag atc tca atg cct gcc cac ctg atg ttt      816
Ala Asp Met Met Arg Lys Lys Ile Ser Met Pro Ala His Leu Met Phe
                260                 265                 270

gac ggg cag gac gac aag ctg ttc gag cac ttc tcc atg gtc gcg cag      864
Asp Gly Gln Asp Asp Lys Leu Phe Glu His Phe Ser Met Val Ala Gln
            275                 280                 285

agg ctt ggc gtt tac acc gcc agg gac tac gcc gac atc ctc gag ttc      912
Arg Leu Gly Val Tyr Thr Ala Arg Asp Tyr Ala Asp Ile Leu Glu Phe
        290                 295                 300

ctc gtc gac agg tgg aag gtg gcg agc ctg act ggt ctg tcg ggt gaa      960
Leu Val Asp Arg Trp Lys Val Ala Ser Leu Thr Gly Leu Ser Gly Glu
    305                 310                 315

ggg aac aag gcg cag gac tac ctt tgc acc ctt gct tca aga atc agg     1008
Gly Asn Lys Ala Gln Asp Tyr Leu Cys Thr Leu Ala Ser Arg Ile Arg
320                 325                 330                 335

agg ctg gag gag agg gcc cag agc aga gcc aag aaa gcc ggc acg ctg     1056
Arg Leu Glu Glu Arg Ala Gln Ser Arg Ala Lys Lys Ala Gly Thr Leu
                340                 345                 350

cct ttc agc tgg gta tac ggt agg gac gtc caa ctg tgagctagca tcatc    1107
Pro Phe Ser Trp Val Tyr Gly Arg Asp Val Gln Leu
            355                 360


<210> SEQ ID NO 12
<211> LENGTH: 363
<212> TYPE: PRT
<213> ORGANISM: Zea mays

<400> SEQUENCE: 12

Met Ala Thr Met Thr Ser Ala Val Ser Thr Lys Val Glu Asn Lys Lys
  1               5                  10                  15

Pro Phe Ala Pro Pro Arg Glu Val His Val Gln Val Thr His Ser Met
             20                  25                  30

Pro Pro His Lys Ile Glu Ile Phe Lys Ser Leu Asp Asp Trp Ala Arg
         35                  40                  45

Asp Asn Ile Leu Thr His Leu Lys Pro Val Glu Lys Cys Trp Gln Pro
     50                  55                  60

Gln Asp Phe Leu Pro Asp Pro Ala Ser Glu Gly Phe His Asp Glu Val
 65                  70                  75                  80

Lys Glu Leu Arg Glu Arg Ala Lys Glu Ile Pro Asp Asp Tyr Phe Val
                 85                  90                  95

Cys Leu Val Gly Asp Met Ile Thr Glu Glu Ala Leu Pro Thr Tyr Gln
            100                 105                 110

Thr Met Leu Asn Thr Leu Asp Gly Val Arg Asp Glu Thr Gly Ala Ser
        115                 120                 125

Pro Thr Ala Trp Ala Val Trp Thr Arg Ala Trp Thr Ala Glu Glu Asn
    130                 135                 140

Arg His Gly Asp Leu Leu Asn Lys Tyr Met Tyr Leu Thr Gly Arg Val
145                 150                 155                 160

Asp Met Arg Gln Ile Glu Lys Thr Ile Gln Tyr Leu Ile Gly Ser Gly
                165                 170                 175

Met Asp Pro Arg Thr Glu Asn Asn Pro Tyr Leu Gly Phe Ile Tyr Thr
            180                 185                 190
```

-continued

```
Ser Phe Gln Glu Arg Ala Thr Phe Ile Ser His Gly Asn Thr Ala Arg
        195                 200                 205

His Ala Lys Asp Phe Gly Asp Leu Lys Leu Ala Gln Ile Cys Gly Ile
    210                 215                 220

Ile Ala Ser Asp Glu Lys Arg His Glu Thr Ala Tyr Thr Lys Ile Val
225                 230                 235                 240

Glu Lys Leu Phe Glu Ile Asp Pro Asp Gly Thr Val Val Ala Leu Ala
                245                 250                 255

Asp Met Met Arg Lys Lys Ile Ser Met Pro Ala His Leu Met Phe Asp
            260                 265                 270

Gly Gln Asp Asp Lys Leu Phe Glu His Phe Ser Met Val Ala Gln Arg
        275                 280                 285

Leu Gly Val Tyr Thr Ala Arg Asp Tyr Ala Asp Ile Leu Glu Phe Leu
    290                 295                 300

Val Asp Arg Trp Lys Val Ala Ser Leu Thr Gly Leu Ser Gly Glu Gly
305                 310                 315                 320

Asn Lys Ala Gln Asp Tyr Leu Cys Thr Leu Ala Ser Arg Ile Arg Arg
                325                 330                 335

Leu Glu Glu Arg Ala Gln Ser Arg Ala Lys Lys Ala Gly Thr Leu Pro
            340                 345                 350

Phe Ser Trp Val Tyr Gly Arg Asp Val Gln Leu
        355                 360


<210> SEQ ID NO 13
<211> LENGTH: 9
<212> TYPE: PRT
<213> ORGANISM: Zea mays

<400> SEQUENCE: 13

Met Thr Ser Ala Val Ser Thr Lys Val
  1               5


<210> SEQ ID NO 14
<211> LENGTH: 10
<212> TYPE: PRT
<213> ORGANISM: Zea mays
<220> FEATURE:
<221> NAME/KEY: UNSURE
<222> LOCATION: (8)
<223> OTHER INFORMATION: unknown

<400> SEQUENCE: 14

Glu Val His Val Gln Val Thr Xaa Ser Met
  1               5                  10


<210> SEQ ID NO 15
<211> LENGTH: 31
<212> TYPE: PRT
<213> ORGANISM: Zea mays

<400> SEQUENCE: 15

Met Ala Leu Arg Leu Asn Asp Val Ala Leu Cys Leu Ser Pro Pro Leu
  1               5                  10                  15

Ala Ala Arg Arg Arg Arg Arg Ser Ser Gly Arg Phe Val Ala Val
             20                  25                  30


<210> SEQ ID NO 16
<211> LENGTH: 42
<212> TYPE: DNA
<213> ORGANISM: Artificial Sequence
```

-continued

```
<220> FEATURE:
<223> OTHER INFORMATION: Description of Artificial Sequence:primer

<400> SEQUENCE: 16

gcactgcaag tatctagact sstrwcasty gywgmwggkr yc                          42


<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 17

aaagctagcc tsctgcygyt ctkkttwycw ggtryc                                 36


<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence:primer

<400> SEQUENCE: 18

tacgttacct gagcggccgc gctgggctca agttttttgt ccaccg                      46


<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 19

tttgctagct tactaacact cattcctgtt gaagctct                               38


<210> SEQ ID NO 20
<211> LENGTH: 102
<212> TYPE: DNA
<213> ORGANISM: Artificial Sequence
<220> FEATURE:
<223> OTHER INFORMATION: Description of Artificial Sequence:primer

<400> SEQUENCE: 20

gcactaggtc aatctagaat ggtaagcgct attgttttat atgtgctttt ggcggcggcg      60

cattctgcct ttgcggcggt tgtgatgacc ccaaacccac tc                         102


<210> SEQ ID NO 21
<211> LENGTH: 738
<212> TYPE: DNA
<213> ORGANISM: mouse
<220> FEATURE:
<221> NAME/KEY: unsure
<222> LOCATION: (16)..(21)
<223> OTHER INFORMATION: not known
<221> NAME/KEY: unsure
<222> LOCATION: (26)
<223> OTHER INFORMATION: not known
<221> NAME/KEY: unsure
<222> LOCATION: (32)
<223> OTHER INFORMATION: not known
<221> NAME/KEY: CDS
<222> LOCATION: (37)..(693)

<400> SEQUENCE: 21

accctcctcc tgttcnnnnn ntcagntgtc ancagt gat gtt gtg atg acc cca        54
                                        Asp Val Val Met Thr Pro
```

-continued

```
                                          1               5

aac cca ctc tcc ctg cct gtc agt ctt gga gat caa gcc tcc atc tct        102
Asn Pro Leu Ser Leu Pro Val Ser Leu Gly Asp Gln Ala Ser Ile Ser
             10                  15                  20

tgc aga tct agt cag agc ctt tta cac agt aat gga atc acc tat tta        150
Cys Arg Ser Ser Gln Ser Leu Leu His Ser Asn Gly Ile Thr Tyr Leu
         25                  30                  35

cat tgg tac ctg cag aag cca ggc cag tct cca aag ctc ctg atc tac        198
His Trp Tyr Leu Gln Lys Pro Gly Gln Ser Pro Lys Leu Leu Ile Tyr
     40                  45                  50

aaa gtt tcc aac cga ttt tct ggg gtc cca gac agg ttc agt ggc agt        246
Lys Val Ser Asn Arg Phe Ser Gly Val Pro Asp Arg Phe Ser Gly Ser
 55                  60                  65                  70

gga tca ggg aca gat ttc aca ctc aag atc aac aga gtg gag gct gag        294
Gly Ser Gly Thr Asp Phe Thr Leu Lys Ile Asn Arg Val Glu Ala Glu
                 75                  80                  85

gat ctg gga gtt tat ttc tgc tct caa agt aca cat gtt ccg tac acg        342
Asp Leu Gly Val Tyr Phe Cys Ser Gln Ser Thr His Val Pro Tyr Thr
             90                  95                 100

ttc gga ggg ggg acc aag ctg gaa ata aaa cgg gct gat gct gca cca        390
Phe Gly Gly Gly Thr Lys Leu Glu Ile Lys Arg Ala Asp Ala Ala Pro
        105                 110                 115

act gta tcc atc ttc cca cca tcc agt gag cag tta aca tct gga ggt        438
Thr Val Ser Ile Phe Pro Pro Ser Ser Glu Gln Leu Thr Ser Gly Gly
    120                 125                 130

gcc tca gtc gtg tgc ttc ttg aac aac ttc tac ccc aaa gac atc aat        486
Ala Ser Val Val Cys Phe Leu Asn Asn Phe Tyr Pro Lys Asp Ile Asn
135                 140                 145                 150

gtc aag tgg aag att gat ggc agt gaa cga caa aat ggc gtc ctg aac        534
Val Lys Trp Lys Ile Asp Gly Ser Glu Arg Gln Asn Gly Val Leu Asn
                155                 160                 165

agt tgg act gat cag gac acc aaa gac agc acc tac agc atg agc agc        582
Ser Trp Thr Asp Gln Asp Thr Lys Asp Ser Thr Tyr Ser Met Ser Ser
            170                 175                 180

acc ctc acg ttg acc aag gac gag tat gaa cga cat aac agc tat acc        630
Thr Leu Thr Leu Thr Lys Asp Glu Tyr Glu Arg His Asn Ser Tyr Thr
        185                 190                 195

tgt gag gcc act cac aag aca tca act tca ccc att gtc aag agc ttc        678
Cys Glu Ala Thr His Lys Thr Ser Thr Ser Pro Ile Val Lys Ser Phe
    200                 205                 210

aac agg aat gag tgt tagtaagcta gcacgcccga tggtgggacg gtatgaataa        733
Asn Arg Asn Glu Cys
215

tccgg                                                                  738


<210> SEQ ID NO 22
<211> LENGTH: 336
<212> TYPE: DNA
<213> ORGANISM: mouse
<220> FEATURE:
<221> NAME/KEY: CDS
<222> LOCATION: (1)..(336)

<400> SEQUENCE: 22

gat gtt gtg atg acc cca aac cca ctc tcc ctg cct gtc agt ctt gga         48
Asp Val Val Met Thr Pro Asn Pro Leu Ser Leu Pro Val Ser Leu Gly
  1               5                  10                  15

gat caa gcc tcc atc tct tgc aga tct agt cag agc ctt tta cac agt         96
Asp Gln Ala Ser Ile Ser Cys Arg Ser Ser Gln Ser Leu Leu His Ser
             20                  25                  30
```

-continued

```
aat gga atc acc tat tta cat tgg tac ctg cag aag cca ggc cag tct      144
Asn Gly Ile Thr Tyr Leu His Trp Tyr Leu Gln Lys Pro Gly Gln Ser
         35                  40                  45

cca aag ctc ctg atc tac aaa gtt tcc aac cga ttt tct ggg gtc cca      192
Pro Lys Leu Leu Ile Tyr Lys Val Ser Asn Arg Phe Ser Gly Val Pro
     50                  55                  60

gac agg ttc agt ggc agt gga tca ggg aca gat ttc aca ctc aag atc      240
Asp Arg Phe Ser Gly Ser Gly Ser Gly Thr Asp Phe Thr Leu Lys Ile
 65                  70                  75                  80

aac aga gtg gag gct gag gat ctg gga gtt tat ttc tgc tct caa agt      288
Asn Arg Val Glu Ala Glu Asp Leu Gly Val Tyr Phe Cys Ser Gln Ser
                 85                  90                  95

aca cat gtt ccg tac acg ttc gga ggg ggg acc aag ctg gaa ata aaa      336
Thr His Val Pro Tyr Thr Phe Gly Gly Gly Thr Lys Leu Glu Ile Lys
            100                 105                 110


<210> SEQ ID NO 23
<211> LENGTH: 108
<212> TYPE: DNA
<213> ORGANISM: Artificial Sequence
<220> FEATURE:
<223> OTHER INFORMATION: Description of Artificial Sequence:primer

<400> SEQUENCE: 23

gcactaggtc aatctagaat ggtaagcgct attgttttat atgtgctttt ggcggcggcg     60

gcgcattctg cctttgcggc ggttcaactg cagcagtctg gggctgag                 108


<210> SEQ ID NO 24
<211> LENGTH: 882
<212> TYPE: DNA
<213> ORGANISM: mouse
<220> FEATURE:
<221> NAME/KEY: CDS
<222> LOCATION: (25)..(837)
<221> NAME/KEY: mat_peptide
<222> LOCATION: (79)..(837)

<400> SEQUENCE: 24

ctgcagggta cggccatatt ggcc atg act atc ctt tgc tgg ctg gcc ctt        51
                           Met Thr Ile Leu Cys Trp Leu Ala Leu
                                       -15                 -10

ctg tca act ctg act gcc gtc aac act gcg gtt gtg atg acc cca aac       99
Leu Ser Thr Leu Thr Ala Val Asn Thr Ala Val Val Met Thr Pro Asn
                 -5              -1   1               5

cca ctc tcc ctg cct gtc agt ctt gga gat caa gcc tcc atc tct tgc      147
Pro Leu Ser Leu Pro Val Ser Leu Gly Asp Gln Ala Ser Ile Ser Cys
         10                  15                  20

aga tct agt cag agc ctt tta cac agt aat gga atc acc tat tta cat      195
Arg Ser Ser Gln Ser Leu Leu His Ser Asn Gly Ile Thr Tyr Leu His
     25                  30                  35

tgg tac ctg cag aag cca ggc cag tct cca aag ctc ctg atc tac aaa      243
Trp Tyr Leu Gln Lys Pro Gly Gln Ser Pro Lys Leu Leu Ile Tyr Lys
 40                  45                  50                  55

gtt tcc aac cga ttt tct ggg gtc cca gac agg ttc agt ggc agt gga      291
Val Ser Asn Arg Phe Ser Gly Val Pro Asp Arg Phe Ser Gly Ser Gly
                 60                  65                  70

tca ggg aca gat ttc aca ctc aag atc agc aga gtg gag gct gag gat      339
Ser Gly Thr Asp Phe Thr Leu Lys Ile Ser Arg Val Glu Ala Glu Asp
             75                  80                  85

ctg gga gtt tat ttc tgc tct caa agt aca cat gtt ccg tac acg ttc      387
Leu Gly Val Tyr Phe Cys Ser Gln Ser Thr His Val Pro Tyr Thr Phe
         90                  95                 100
```

-continued

```
gga ggg ggg acc aag ctg gaa ata aaa ggc agc acc agc ggc agc ggc      435
Gly Gly Gly Thr Lys Leu Glu Ile Lys Gly Ser Thr Ser Gly Ser Gly
    105                 110                 115

aag ccg ggc agc ggc gag ggc agc acc aag ggc cat gtt caa ctg cag      483
Lys Pro Gly Ser Gly Glu Gly Ser Thr Lys Gly His Val Gln Leu Gln
120                 125                 130                 135

cag tct ggg gct gag ctg gtg agg cct ggg gct tca gtg acg ctg tcc      531
Gln Ser Gly Ala Glu Leu Val Arg Pro Gly Ala Ser Val Thr Leu Ser
                140                 145                 150

tgc aag gct tcg ggc tac aca ttt act gac tat gaa ata cac tgg gtg      579
Cys Lys Ala Ser Gly Tyr Thr Phe Thr Asp Tyr Glu Ile His Trp Val
            155                 160                 165

agg cag aca cct gtg cat ggc ctg gaa tgg att gga gct att gat cct      627
Arg Gln Thr Pro Val His Gly Leu Glu Trp Ile Gly Ala Ile Asp Pro
        170                 175                 180

gaa act ggt ggt act gcc tac aat cag aag ttc aag gac aag gcc ata      675
Glu Thr Gly Gly Thr Ala Tyr Asn Gln Lys Phe Lys Asp Lys Ala Ile
    185                 190                 195

gtg act gta gac aaa tcc tcc agc aca gcc tac atg gag ctc cgc agc      723
Val Thr Val Asp Lys Ser Ser Ser Thr Ala Tyr Met Glu Leu Arg Ser
200                 205                 210                 215

ctg aca tct gaa gac tct gcc gtc tat tac tat aca aga tgg ttt gag      771
Leu Thr Ser Glu Asp Ser Ala Val Tyr Tyr Tyr Thr Arg Trp Phe Glu
                220                 225                 230

gac tgg ggc caa ggg act ctg gtc act gtc tct gca atg cgg ggt tct      819
Asp Trp Gly Gln Gly Thr Leu Val Thr Val Ser Ala Met Arg Gly Ser
            235                 240                 245

cat cat cat cat cat cat tagggcctct ctggccgatc ccccgaattt             867
His His His His His His
        250

ccccgatcgt tcaaa                                                     882


<210> SEQ ID NO 25
<211> LENGTH: 339
<212> TYPE: DNA
<213> ORGANISM: mouse
<220> FEATURE:
<221> NAME/KEY: CDS
<222> LOCATION: (1)..(339)

<400> SEQUENCE: 25

cag gtt gtg atg acc cca aac cca ctc tcc ctg cct gtc agt ctt gga       48
Gln Val Val Met Thr Pro Asn Pro Leu Ser Leu Pro Val Ser Leu Gly
  1               5                  10                  15

gat caa gcc tcc atc tct tgc aga tct agt cag agc ctt tta cac agt       96
Asp Gln Ala Ser Ile Ser Cys Arg Ser Ser Gln Ser Leu Leu His Ser
             20                  25                  30

aat gga atc acc tat tta cat tgg tac ctg cag aag cca ggc cag tct      144
Asn Gly Ile Thr Tyr Leu His Trp Tyr Leu Gln Lys Pro Gly Gln Ser
         35                  40                  45

cca aag ctc ctg atc tac aaa gtt tcc aac cga ttt tct ggg gtc cca      192
Pro Lys Leu Leu Ile Tyr Lys Val Ser Asn Arg Phe Ser Gly Val Pro
     50                  55                  60

gac agg ttc agt ggc agt gga tca ggg aca gat ttc aca ctc aag atc      240
Asp Arg Phe Ser Gly Ser Gly Ser Gly Thr Asp Phe Thr Leu Lys Ile
 65                  70                  75                  80

agc aga gtg gag gct gag gat ctg gga gtt tat ttc tgc tct caa agt      288
Ser Arg Val Glu Ala Glu Asp Leu Gly Val Tyr Phe Cys Ser Gln Ser
                 85                  90                  95

aca cat gtt ccg tac acg ttc gga ggg ggg acc aag ctg gaa ata aaa      336
Thr His Val Pro Tyr Thr Phe Gly Gly Gly Thr Lys Leu Glu Ile Lys
```

-continued

```
            100                 105                 110

ggc                                                                    339
Gly


<210> SEQ ID NO 26
<211> LENGTH: 64
<212> TYPE: DNA
<213> ORGANISM: Artificial Sequence
<220> FEATURE:
<223> OTHER INFORMATION: Description of Artificial Sequence:primer

<400> SEQUENCE: 26

cccgggtttg gattcggagc cagatcctga ggatttaccc tctgcagaga cagtgaccag     60

agtc                                                                  64


<210> SEQ ID NO 27
<211> LENGTH: 63
<212> TYPE: DNA
<213> ORGANISM: Artificial Sequence
<220> FEATURE:
<223> OTHER INFORMATION: Description of Artificial Sequence:primer

<400> SEQUENCE: 27

gagggtaaat cctcaggatc tggctccgaa tccaaacccg gggatgttgt gatgacccca     60

aac                                                                   63


<210> SEQ ID NO 28
<211> LENGTH: 78
<212> TYPE: DNA
<213> ORGANISM: Artificial Sequence
<220> FEATURE:
<223> OTHER INFORMATION: Description of Artificial Sequence:primer

<400> SEQUENCE: 28

gcactaggtc aagcggccgc ttactaattc agatcctctt ctgagatgag tttttcttct     60

tttatttcca gcttggtc                                                   78


<210> SEQ ID NO 29
<211> LENGTH: 459
<212> TYPE: DNA
<213> ORGANISM: mouse
<220> FEATURE:
<221> NAME/KEY: CDS
<222> LOCATION: (19)..(459)
<221> NAME/KEY: mat_peptide
<222> LOCATION: (79)..(459)

<400> SEQUENCE: 29

gcactaggtc aatctaga atg gta agc gct att gtt tta tat gtg ctt ttg       51
                    Met Val Ser Ala Ile Val Leu Tyr Val Leu Leu
                    -20                 -15                 -10

gcg gcg gcg gcg cat tct gcc ttt gcg gcg gtt caa ctg cag cag tct       99
Ala Ala Ala Ala His Ser Ala Phe Ala Ala Val Gln Leu Gln Gln Ser
                -5              -1   1               5

ggg gct gag ctg gtg agg cct ggg gct tca gtg acg ctg tcc tgc aag      147
Gly Ala Glu Leu Val Arg Pro Gly Ala Ser Val Thr Leu Ser Cys Lys
        10                  15                  20

gct tcg ggc tac aca ttt act gac tat gaa ata cac tgg gtg agg cag      195
Ala Ser Gly Tyr Thr Phe Thr Asp Tyr Glu Ile His Trp Val Arg Gln
     25                  30                  35

aca cct gtg cat ggc ctg gaa tgg att gga gct att gat cct gaa act      243
Thr Pro Val His Gly Leu Glu Trp Ile Gly Ala Ile Asp Pro Glu Thr
 40                  45                  50                  55
```

```
ggt ggt act gcc tac aat cag aag ttc aag gac aag gcc ata gtg act      291
Gly Gly Thr Ala Tyr Asn Gln Lys Phe Lys Asp Lys Ala Ile Val Thr
            60                  65                  70

gta gac aaa tcc tcc agc aca gcc tac atg gag ctc cgc agc ctg aca      339
Val Asp Lys Ser Ser Ser Thr Ala Tyr Met Glu Leu Arg Ser Leu Thr
        75                  80                  85

tct gaa gac tct gcc gtc tat tac tat aca aga tgg ttt gag gac tgg      387
Ser Glu Asp Ser Ala Val Tyr Tyr Tyr Thr Arg Trp Phe Glu Asp Trp
    90                  95                  100

ggc caa ggg act ctg gtc act gtc tct gca gag ggt aaa tcc tca gga      435
Gly Gln Gly Thr Leu Val Thr Val Ser Ala Glu Gly Lys Ser Ser Gly
105                 110                 115

tct ggc tcc gaa tcc aaa ccc ggg                                      459
Ser Gly Ser Glu Ser Lys Pro Gly
120             125

<210> SEQ ID NO 30
<211> LENGTH: 438
<212> TYPE: DNA
<213> ORGANISM: mouse
<220> FEATURE:
<221> NAME/KEY: CDS
<222> LOCATION: (1)..(408)

<400> SEQUENCE: 30

gag ggt aaa tcc tca gga tct ggc tcc gaa tcc aaa ccc ggg gat gtt      48
Glu Gly Lys Ser Ser Gly Ser Gly Ser Glu Ser Lys Pro Gly Asp Val
1               5                   10                  15

gtg atg acc cca aac cca ctc tcc ctg cct gtc agt ctt gga gat caa      96
Val Met Thr Pro Asn Pro Leu Ser Leu Pro Val Ser Leu Gly Asp Gln
            20                  25                  30

gcc tcc atc tct tgc aga tct agt cag agc ctt tta cac agt aat gga     144
Ala Ser Ile Ser Cys Arg Ser Ser Gln Ser Leu Leu His Ser Asn Gly
        35                  40                  45

atc acc tat tta cat tgg tac ctg cag aag cca ggc cag tct cca aag     192
Ile Thr Tyr Leu His Trp Tyr Leu Gln Lys Pro Gly Gln Ser Pro Lys
    50                  55                  60

ctc ctg atc tac aaa gtt tcc aac cga ttt tct ggg gtc cca gac agg     240
Leu Leu Ile Tyr Lys Val Ser Asn Arg Phe Ser Gly Val Pro Asp Arg
65                  70                  75                  80

ttc agt ggc agt gga tca ggg aca gat ttc aca ctc aag atc agc aga     288
Phe Ser Gly Ser Gly Ser Gly Thr Asp Phe Thr Leu Lys Ile Ser Arg
                85                  90                  95

gtg gag gct gag gat ctg gga gtt tat ttc tgc tct caa agt aca cat     336
Val Glu Ala Glu Asp Leu Gly Val Tyr Phe Cys Ser Gln Ser Thr His
            100                 105                 110

gtt ccg tac acg ttc gga ggg ggg acc aag ctg gaa ata aaa gaa gaa     384
Val Pro Tyr Thr Phe Gly Gly Gly Thr Lys Leu Glu Ile Lys Glu Glu
        115                 120                 125

aaa ctc atc tca gaa gag gat ctg aattagtaag gggccgcctt gacctagtgc    438
Lys Leu Ile Ser Glu Glu Asp Leu
    130                 135

<210> SEQ ID NO 31
<211> LENGTH: 830
<212> TYPE: DNA
<213> ORGANISM: mouse
<220> FEATURE:
<221> NAME/KEY: CDS
<222> LOCATION: (7)..(813)
<221> NAME/KEY: mat_peptide
<222> LOCATION: (67)..(813)
```

-continued

```
<400> SEQUENCE: 31

tctaga atg gta agc gct att gtt tta tat gtg ctt ttg gcg gcg gcg        48
       Met Val Ser Ala Ile Val Leu Tyr Val Leu Leu Ala Ala Ala
       -20                 -15                 -10

gcg cat tct gcc ttt gcg gcg gtt caa ctg cag cag tct ggg gct gag       96
Ala His Ser Ala Phe Ala Ala Val Gln Leu Gln Gln Ser Gly Ala Glu
     -5              -1   1               5                  10

ctg gtg agg cct ggg gct tca gtg acg ctg tcc tgc aag gct tcg ggc      144
Leu Val Arg Pro Gly Ala Ser Val Thr Leu Ser Cys Lys Ala Ser Gly
                 15                  20                  25

tac aca ttt act gac tat gaa ata cac tgg gtg agg cag aca cct gtg      192
Tyr Thr Phe Thr Asp Tyr Glu Ile His Trp Val Arg Gln Thr Pro Val
             30                  35                  40

cat ggc ctg gaa tgg att gga gct att gat cct gaa act ggt ggt act      240
His Gly Leu Glu Trp Ile Gly Ala Ile Asp Pro Glu Thr Gly Gly Thr
         45                  50                  55

gcc tac aat cag aag ttc aag gac aag gcc ata gtg act gta gac aaa      288
Ala Tyr Asn Gln Lys Phe Lys Asp Lys Ala Ile Val Thr Val Asp Lys
     60                  65                  70

tcc tcc agc aca gcc tac atg gag ctc cgc agc ctg aca tct gaa gac      336
Ser Ser Ser Thr Ala Tyr Met Glu Leu Arg Ser Leu Thr Ser Glu Asp
 75                  80                  85                  90

tct gcc gtc tat tac tat aca aga tgg ttt gag gac tgg ggc caa ggg      384
Ser Ala Val Tyr Tyr Tyr Thr Arg Trp Phe Glu Asp Trp Gly Gln Gly
                 95                 100                 105

act ctg gtc act gtc tct gca gag ggt aaa tcc tca gga tct ggc tcc      432
Thr Leu Val Thr Val Ser Ala Glu Gly Lys Ser Ser Gly Ser Gly Ser
             110                 115                 120

gaa tcc aaa ccc ggg gat gtt gtg atg acc cca aac cca ctc tcc ctg      480
Glu Ser Lys Pro Gly Asp Val Val Met Thr Pro Asn Pro Leu Ser Leu
         125                 130                 135

cct gtc agt ctt gga gat caa gcc tcc atc tct tgc aga tct agt cag      528
Pro Val Ser Leu Gly Asp Gln Ala Ser Ile Ser Cys Arg Ser Ser Gln
    140                 145                 150

agc ctt tta cac agt aat gga atc acc tat tta cat tgg tac ctg cag      576
Ser Leu Leu His Ser Asn Gly Ile Thr Tyr Leu His Trp Tyr Leu Gln
155                 160                 165                 170

aag cca ggc cag tct cca aag ctc ctg atc tac aaa gtt tcc aac cga      624
Lys Pro Gly Gln Ser Pro Lys Leu Leu Ile Tyr Lys Val Ser Asn Arg
                175                 180                 185

ttt tct ggg gtc cca gac agg ttc agt ggc agt gga tca ggg aca gat      672
Phe Ser Gly Val Pro Asp Arg Phe Ser Gly Ser Gly Ser Gly Thr Asp
            190                 195                 200

ttc aca ctc aag atc agc aga gtg gag gct gag gat ctg gga gtt tat      720
Phe Thr Leu Lys Ile Ser Arg Val Glu Ala Glu Asp Leu Gly Val Tyr
        205                 210                 215

ttc tgc tct caa agt aca cat gtt ccg tac acg ttc gga ggg ggg acc      768
Phe Cys Ser Gln Ser Thr His Val Pro Tyr Thr Phe Gly Gly Gly Thr
    220                 225                 230

aag ctg gaa ata aaa gaa gaa aaa ctc atc tca gaa gag gat ctg          813
Lys Leu Glu Ile Lys Glu Glu Lys Leu Ile Ser Glu Glu Asp Leu
235                 240                 245

aattagtaag cggccgc                                                   830


<210> SEQ ID NO 32
<211> LENGTH: 269
<212> TYPE: PRT
<213> ORGANISM: mouse

<400> SEQUENCE: 32
```

-continued

```
Met Val Ser Ala Ile Val Leu Tyr Val Leu Leu Ala Ala Ala Ala His
-20                 -15                 -10                  -5

Ser Ala Phe Ala Ala Val Gln Leu Gln Gln Ser Gly Ala Glu Leu Val
             -1   1               5                  10

Arg Pro Gly Ala Ser Val Thr Leu Ser Cys Lys Ala Ser Gly Tyr Thr
         15                  20                  25

Phe Thr Asp Tyr Glu Ile His Trp Val Arg Gln Thr Pro Val His Gly
     30                  35                  40

Leu Glu Trp Ile Gly Ala Ile Asp Pro Glu Thr Gly Gly Thr Ala Tyr
 45                  50                  55                  60

Asn Gln Lys Phe Lys Asp Lys Ala Ile Val Thr Val Asp Lys Ser Ser
                 65                  70                  75

Ser Thr Ala Tyr Met Glu Leu Arg Ser Leu Thr Ser Glu Asp Ser Ala
             80                  85                  90

Val Tyr Tyr Tyr Thr Arg Trp Phe Glu Asp Trp Gly Gln Gly Thr Leu
         95                 100                 105

Val Thr Val Ser Ala Glu Gly Lys Ser Ser Gly Ser Gly Ser Glu Ser
    110                 115                 120

Lys Pro Gly Asp Val Val Met Thr Pro Asn Pro Leu Ser Leu Pro Val
125                 130                 135                 140

Ser Leu Gly Asp Gln Ala Ser Ile Ser Cys Arg Ser Ser Gln Ser Leu
                145                 150                 155

Leu His Ser Asn Gly Ile Thr Tyr Leu His Trp Tyr Leu Gln Lys Pro
            160                 165                 170

Gly Gln Ser Pro Lys Leu Leu Ile Tyr Lys Val Ser Asn Arg Phe Ser
        175                 180                 185

Gly Val Pro Asp Arg Phe Ser Gly Ser Gly Ser Gly Thr Asp Phe Thr
    190                 195                 200

Leu Lys Ile Ser Arg Val Glu Ala Glu Asp Leu Gly Val Tyr Phe Cys
205                 210                 215                 220

Ser Gln Ser Thr His Val Pro Tyr Thr Phe Gly Gly Gly Thr Lys Leu
                225                 230                 235

Glu Ile Lys Glu Glu Lys Leu Ile Ser Glu Glu Asp Leu
            240                 245
```

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence:c-myc tag

<400> SEQUENCE: 33
gaagaaaaac tcatctcaga agaggatctg 30

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence:p67 leader

<400> SEQUENCE: 34
atggtaagcg ctattgtttt atatgtgctt ttggcggcgg cggcgcattc tgcctttgcg 60

<210> SEQ ID NO 35
<211> LENGTH: 84

-continued

<212> TYPE: DNA
<213> ORGANISM: Artificial Sequence
<220> FEATURE:
<223> OTHER INFORMATION: Description of Artificial Sequence:primer

<400> SEQUENCE: 35
gcactaggtc aatctagaat gactatcctt tgctggctgg cccttctgtc aactctgact 60
gccgtcaacg ctgcggttgt gatg 84

<210> SEQ ID NO 36
<211> LENGTH: 70
<212> TYPE: DNA
<213> ORGANISM: Artificial Sequence
<220> FEATURE:
<223> OTHER INFORMATION: Description of Artificial Sequence:primer

<400> SEQUENCE: 36
gcccttggtg ccctcgccgc tgcccggctt gccgctgccg ctggtgctgc cttttatttc 60
cagcttggtc 70

<210> SEQ ID NO 37
<211> LENGTH: 74
<212> TYPE: DNA
<213> ORGANISM: Artificial Sequence
<220> FEATURE:
<223> OTHER INFORMATION: Description of Artificial Sequence:primer

<400> SEQUENCE: 37
ggcagcacca gcggcagcgg caagccgggc agcggcgagg gcagcaccaa gggccaggtt 60
caactgcagc agtc 74

<210> SEQ ID NO 38
<211> LENGTH: 72
<212> TYPE: DNA
<213> ORGANISM: Artificial Sequence
<220> FEATURE:
<223> OTHER INFORMATION: Description of Artificial Sequence:primer

<400> SEQUENCE: 38
gcactaggtc aagcggccgc atgatgatga tgatgatgag aaccccgcat tgcagagaca 60
gtgaccagag tc 72

<210> SEQ ID NO 39
<211> LENGTH: 41
<212> TYPE: DNA
<213> ORGANISM: Artificial Sequence
<220> FEATURE:
<223> OTHER INFORMATION: Description of Artificial Sequence:primer

<400> SEQUENCE: 39
aaaatttgcg gccgcctaat gatgatgatg atgatgagaa c 41

<210> SEQ ID NO 40
<211> LENGTH: 462
<212> TYPE: DNA
<213> ORGANISM: mouse
<220> FEATURE:
<221> NAME/KEY: CDS
<222> LOCATION: (19)..(462)
<221> NAME/KEY: mat_peptide
<222> LOCATION: (73)..(462)

<400> SEQUENCE: 40
gcactaggtc aatctaga atg act atc ctt tgc tgg cta gcc ctt ctg tca 51

-continued

```
                  Met Thr Ile Leu Cys Trp Leu Ala Leu Leu Ser
                                  -15                 -10

act ctg act gcc gtc aac gct gcg gtt gtg atg acc cca aac cca ctc       99
Thr Leu Thr Ala Val Asn Ala Ala Val Val Met Thr Pro Asn Pro Leu
         -5              -1   1               5

tcc ctg cct gtc agt ctt gga gat caa gcc tcc atc tct tgc aga tct      147
Ser Leu Pro Val Ser Leu Gly Asp Gln Ala Ser Ile Ser Cys Arg Ser
 10                  15                  20                  25

agt cag agc ctt tta cac agt aat gga atc acc tat tta cat tgg tac      195
Ser Gln Ser Leu Leu His Ser Asn Gly Ile Thr Tyr Leu His Trp Tyr
                 30                  35                  40

ctg cag aag cca ggc cag tct cca aag ctc ctg atc tac aaa gtt tcc      243
Leu Gln Lys Pro Gly Gln Ser Pro Lys Leu Leu Ile Tyr Lys Val Ser
             45                  50                  55

aac cga ttt tct ggg gtc cca gac agg ttc agt ggc agt gga tca ggg      291
Asn Arg Phe Ser Gly Val Pro Asp Arg Phe Ser Gly Ser Gly Ser Gly
         60                  65                  70

aca gat ttc aca ctc aag atc agc aga gtg gag gct gag gat ctg gga      339
Thr Asp Phe Thr Leu Lys Ile Ser Arg Val Glu Ala Glu Asp Leu Gly
     75                  80                  85

gtt tat ttc tgc tct caa agt aca cat gtt ccg tac acg ttc gga ggg      387
Val Tyr Phe Cys Ser Gln Ser Thr His Val Pro Tyr Thr Phe Gly Gly
 90                  95                 100                 105

ggg acc aag ctg gaa ata aaa ggc agc acc agc ggc agc ggc aag ccg      435
Gly Thr Lys Leu Glu Ile Lys Gly Ser Thr Ser Gly Ser Gly Lys Pro
                110                 115                 120

ggc agc ggc gag ggc agc acc aag ggc                                  462
Gly Ser Gly Glu Gly Ser Thr Lys Gly
            125                 130


<210> SEQ ID NO 41
<211> LENGTH: 443
<212> TYPE: DNA
<213> ORGANISM: mouse
<220> FEATURE:
<221> NAME/KEY: CDS
<222> LOCATION: (1)..(423)

<400> SEQUENCE: 41

ggc agc acc agc ggc agc ggc aag ccg ggc agc ggc gag ggc agc acc       48
Gly Ser Thr Ser Gly Ser Gly Lys Pro Gly Ser Gly Glu Gly Ser Thr
  1               5                  10                  15

aag ggc cat gtt caa ctg cag cag tct ggg gct gag ctg gtg agg cct       96
Lys Gly His Val Gln Leu Gln Gln Ser Gly Ala Glu Leu Val Arg Pro
             20                  25                  30

ggg gct tca gtg acg ctg tcc tgc aag gct tcg ggc tac aca ttt act      144
Gly Ala Ser Val Thr Leu Ser Cys Lys Ala Ser Gly Tyr Thr Phe Thr
         35                  40                  45

gac tat gaa ata cac tgg gtg aag cag aca cct gtg cat ggc ctg gaa      192
Asp Tyr Glu Ile His Trp Val Lys Gln Thr Pro Val His Gly Leu Glu
     50                  55                  60

tgg att gga gct att gat cct gaa act ggt ggt act gcc tac aat cag      240
Trp Ile Gly Ala Ile Asp Pro Glu Thr Gly Gly Thr Ala Tyr Asn Gln
 65                  70                  75                  80

aag ttc aag gac aag gcc ata gtg act gta gac aaa tcc tcc agc aca      288
Lys Phe Lys Asp Lys Ala Ile Val Thr Val Asp Lys Ser Ser Ser Thr
                 85                  90                  95

gcc tac atg gag ctc cgc agc ctg aca tct gaa gac tct gcc gtc tat      336
Ala Tyr Met Glu Leu Arg Ser Leu Thr Ser Glu Asp Ser Ala Val Tyr
            100                 105                 110

tac tat aca aga tgg ttt gag gac tgg ggc caa ggg act ctg gtc act      384
```

-continued

```
Tyr Tyr Thr Arg Trp Phe Glu Asp Trp Gly Gln Gly Thr Leu Val Thr
        115                 120                 125

gtc tct gca atg cgg ggt tct cat cat cat cat cat cat gcggccgctt       433
Val Ser Ala Met Arg Gly Ser His His His His His His
    130                 135                 140

gacctagtgc                                                           443


<210> SEQ ID NO 42
<211> LENGTH: 851
<212> TYPE: DNA
<213> ORGANISM: mouse
<220> FEATURE:
<221> NAME/KEY: CDS
<222> LOCATION: (19)..(831)
<221> NAME/KEY: mat_peptide
<222> LOCATION: (73)..(831)

<400> SEQUENCE: 42

gcactaggtc aatctaga atg act atc ctt tgc tgg cta gcc ctt ctg tca       51
                    Met Thr Ile Leu Cys Trp Leu Ala Leu Leu Ser
                                -15                 -10

act ctg act gcc gtc aac gct gcg gtt gtg atg acc cca aac cca ctc       99
Thr Leu Thr Ala Val Asn Ala Ala Val Val Met Thr Pro Asn Pro Leu
        -5              -1   1               5

tcc ctg cct gtc agt ctt gga gat caa gcc tcc atc tct tgc aga tct      147
Ser Leu Pro Val Ser Leu Gly Asp Gln Ala Ser Ile Ser Cys Arg Ser
 10                  15                  20                  25

agt cag agc ctt tta cac agt aat gga atc acc tat tta cat tgg tac      195
Ser Gln Ser Leu Leu His Ser Asn Gly Ile Thr Tyr Leu His Trp Tyr
                 30                  35                  40

ctg cag aag cca ggc cag tct cca aag ctc ctg atc tac aaa gtt tcc      243
Leu Gln Lys Pro Gly Gln Ser Pro Lys Leu Leu Ile Tyr Lys Val Ser
             45                  50                  55

aac cga ttt tct ggg gtc cca gac agg ttc agt ggc agt gga tca ggg      291
Asn Arg Phe Ser Gly Val Pro Asp Arg Phe Ser Gly Ser Gly Ser Gly
         60                  65                  70

aca gat ttc aca ctc aag atc agc aga gtg gag gct gag gat ctg gga      339
Thr Asp Phe Thr Leu Lys Ile Ser Arg Val Glu Ala Glu Asp Leu Gly
     75                  80                  85

gtt tat ttc tgc tct caa agt aca cat gtt ccg tac acg ttc gga ggg      387
Val Tyr Phe Cys Ser Gln Ser Thr His Val Pro Tyr Thr Phe Gly Gly
 90                  95                 100                 105

ggg acc aag ctg gaa ata aaa ggc agc acc agc ggc agc ggc aag ccg      435
Gly Thr Lys Leu Glu Ile Lys Gly Ser Thr Ser Gly Ser Gly Lys Pro
                110                 115                 120

ggc agc ggc gag ggc agc acc aag ggc cat gtt caa ctg cag cag tct      483
Gly Ser Gly Glu Gly Ser Thr Lys Gly His Val Gln Leu Gln Gln Ser
            125                 130                 135

ggg gct gag ctg gtg agg cct ggg gct tca gtg acg ctg tcc tgc aag      531
Gly Ala Glu Leu Val Arg Pro Gly Ala Ser Val Thr Leu Ser Cys Lys
        140                 145                 150

gct tcg ggc tac aca ttt act gac tat gaa ata cac tgg gtg aag cag      579
Ala Ser Gly Tyr Thr Phe Thr Asp Tyr Glu Ile His Trp Val Lys Gln
    155                 160                 165

aca cct gtg cat ggc ctg gaa tgg att gga gct att gat cct gaa act      627
Thr Pro Val His Gly Leu Glu Trp Ile Gly Ala Ile Asp Pro Glu Thr
170                 175                 180                 185

ggt ggt act gcc tac aat cag aag ttc aag gac aag gcc ata gtg act      675
Gly Gly Thr Ala Tyr Asn Gln Lys Phe Lys Asp Lys Ala Ile Val Thr
                190                 195                 200

gta gac aaa tcc tcc agc aca gcc tac atg gag ctc cgc agc ctg aca      723
```

-continued

```
Val Asp Lys Ser Ser Ser Thr Ala Tyr Met Glu Leu Arg Ser Leu Thr
            205                 210                 215

tct gaa gac tct gcc gtc tat tac tat aca aga tgg ttt gag gac tgg      771
Ser Glu Asp Ser Ala Val Tyr Tyr Tyr Thr Arg Trp Phe Glu Asp Trp
        220                 225                 230

ggc caa ggg act ctg gtc act gtc tct gca atg cgg ggt tct cat cat      819
Gly Gln Gly Thr Leu Val Thr Val Ser Ala Met Arg Gly Ser His His
    235                 240                 245

cat cat cat cat gcggccgctt gacctagtgc                                851
His His His His
250


<210> SEQ ID NO 43
<211> LENGTH: 867
<212> TYPE: DNA
<213> ORGANISM: mouse
<220> FEATURE:
<221> NAME/KEY: CDS
<222> LOCATION: (31)..(843)
<221> NAME/KEY: mat_peptide
<222> LOCATION: (85)..(843)

<400> SEQUENCE: 43

aatttaaacg gatcccgggt accttctaga atg act atc ctt tgc tgg cta gcc      54
                                 Met Thr Ile Leu Cys Trp Leu Ala
                                             -15

ctt ctg tca act ctg act gcc gtc aac gct gcg gtt gtg atg acc cca      102
Leu Leu Ser Thr Leu Thr Ala Val Asn Ala Ala Val Val Met Thr Pro
-10                 -5                  -1   1               5

aac cca ctc tcc ctg cct gtc agt ctt gga gat caa gcc tcc atc tct      150
Asn Pro Leu Ser Leu Pro Val Ser Leu Gly Asp Gln Ala Ser Ile Ser
            10                  15                  20

tgc aga tct agt cag agc ctt tta cac agt aat gga atc acc tat tta      198
Cys Arg Ser Ser Gln Ser Leu Leu His Ser Asn Gly Ile Thr Tyr Leu
        25                  30                  35

cat tgg tac ctg cag aag cca ggc cag tct cca aag ctc ctg atc tac      246
His Trp Tyr Leu Gln Lys Pro Gly Gln Ser Pro Lys Leu Leu Ile Tyr
    40                  45                  50

aaa gtt tcc aac cga ttt tct ggg gtc cca gac agg ttc agt ggc agt      294
Lys Val Ser Asn Arg Phe Ser Gly Val Pro Asp Arg Phe Ser Gly Ser
 55                 60                  65                  70

gga tca ggg aca gat ttc aca ctc aag atc agc aga gtg gag gct gag      342
Gly Ser Gly Thr Asp Phe Thr Leu Lys Ile Ser Arg Val Glu Ala Glu
                75                  80                  85

gat ctg gga gtt tat ttc tgc tct caa agt aca cat gtt ccg tac acg      390
Asp Leu Gly Val Tyr Phe Cys Ser Gln Ser Thr His Val Pro Tyr Thr
            90                  95                  100

ttc gga ggg ggg acc aag ctg gaa ata aaa ggc agc acc agc ggc agc      438
Phe Gly Gly Gly Thr Lys Leu Glu Ile Lys Gly Ser Thr Ser Gly Ser
        105                 110                 115

ggc aag ccg ggc agc ggc gag ggc agc acc aag ggc cat gtt caa ctg      486
Gly Lys Pro Gly Ser Gly Glu Gly Ser Thr Lys Gly His Val Gln Leu
    120                 125                 130

cag cag tct ggg gct gag ctg gtg agg cct ggg gct tca gtg acg ctg      534
Gln Gln Ser Gly Ala Glu Leu Val Arg Pro Gly Ala Ser Val Thr Leu
135                 140                 145                 150

tcc tgc aag gct tcg ggc tac aca ttt act gac tat gaa ata cac tgg      582
Ser Cys Lys Ala Ser Gly Tyr Thr Phe Thr Asp Tyr Glu Ile His Trp
                155                 160                 165

gtg aag cag aca cct gtg cat ggc ctg gaa tgg att gga gct att gat      630
Val Lys Gln Thr Pro Val His Gly Leu Glu Trp Ile Gly Ala Ile Asp
            170                 175                 180
```

-continued

```
cct gaa act ggt ggt act gcc tac aat cag aag ttc aag gac aag gcc      678
Pro Glu Thr Gly Gly Thr Ala Tyr Asn Gln Lys Phe Lys Asp Lys Ala
        185                 190                 195

ata gtg act gta gac aaa tcc tcc agc aca gcc tac atg gag ctc cgc      726
Ile Val Thr Val Asp Lys Ser Ser Ser Thr Ala Tyr Met Glu Leu Arg
    200                 205                 210

agc ctg aca tct gaa gac tct gcc gtc tat tac tat aca aga tgg ttt      774
Ser Leu Thr Ser Glu Asp Ser Ala Val Tyr Tyr Tyr Thr Arg Trp Phe
215                 220                 225                 230

gag gac tgg ggc caa ggg act ctg gtc act gtc tct gca atg cgg ggt      822
Glu Asp Trp Gly Gln Gly Thr Leu Val Thr Val Ser Ala Met Arg Gly
                235                 240                 245

tct cat cat cat cat cat cat taggcggccg ctgcagatct gatc               867
Ser His His His His His His
            250
```

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 44

```
tttaaaggcc atattggcca tgactatcct ttgctggct                            39
```

<210> SEQ ID NO 45
<211> LENGTH: 43
<212> TYPE: DNA
<213> ORGANISM: Artificial Sequence
<220> FEATURE:
<223> OTHER INFORMATION: Description of Artificial Sequence:primer

<400> SEQUENCE: 45

```
tttaaaggcc atattggcca tggatgttgt gatgacccca aac                       43
```

<210> SEQ ID NO 46
<211> LENGTH: 54
<212> TYPE: DNA
<213> ORGANISM: Artificial Sequence
<220> FEATURE:
<223> OTHER INFORMATION: Description of Artificial Sequence:primer

<400> SEQUENCE: 46

```
tttaaaggcc agagaggccc taatgatgat gatgatgatg agaaccccgc attg           54
```

<210> SEQ ID NO 47
<211> LENGTH: 882
<212> TYPE: DNA
<213> ORGANISM: mouse
<220> FEATURE:
<221> NAME/KEY: CDS
<222> LOCATION: (25)..(837)
<221> NAME/KEY: mat_peptide
<222> LOCATION: (79)..(837)

<400> SEQUENCE: 47

```
ctgcagggta cggccatatt ggcc atg act atc ctt tgc tgg ctg gcc ctt        51
                           Met Thr Ile Leu Cys Trp Leu Ala Leu
                                       -15                 -10

ctg tca act ctg act gcc gtc aac act gcg gtt gtg atg acc cca aac       99
Leu Ser Thr Leu Thr Ala Val Asn Thr Ala Val Val Met Thr Pro Asn
                 -5              -1   1               5

cca ctc tcc ctg cct gtc agt ctt gga gat caa gcc tcc atc tct tgc      147
```

-continued

```
Pro Leu Ser Leu Pro Val Ser Leu Gly Asp Gln Ala Ser Ile Ser Cys
         10                  15                  20

aga tct agt cag agc ctt tta cac agt aat gga atc acc tat tta cat      195
Arg Ser Ser Gln Ser Leu Leu His Ser Asn Gly Ile Thr Tyr Leu His
     25                  30                  35

tgg tac ctg cag aag cca ggc cag tct cca aag ctc ctg atc tac aaa      243
Trp Tyr Leu Gln Lys Pro Gly Gln Ser Pro Lys Leu Leu Ile Tyr Lys
 40                  45                  50                  55

gtt tcc aac cga ttt tct ggg gtc cca gac agg ttc agt ggc agt gga      291
Val Ser Asn Arg Phe Ser Gly Val Pro Asp Arg Phe Ser Gly Ser Gly
                 60                  65                  70

tca ggg aca gat ttc aca ctc aag atc agc aga gtg gag gct gag gat      339
Ser Gly Thr Asp Phe Thr Leu Lys Ile Ser Arg Val Glu Ala Glu Asp
             75                  80                  85

ctg gga gtt tat ttc tgc tct caa agt aca cat gtt ccg tac acg ttc      387
Leu Gly Val Tyr Phe Cys Ser Gln Ser Thr His Val Pro Tyr Thr Phe
         90                  95                 100

gga ggg ggg acc aag ctg gaa ata aaa ggc agc acc agc ggc agc ggc      435
Gly Gly Gly Thr Lys Leu Glu Ile Lys Gly Ser Thr Ser Gly Ser Gly
    105                 110                 115

aag ccg ggc agc ggc gag ggc agc acc aag ggc cat gtt caa ctg cag      483
Lys Pro Gly Ser Gly Glu Gly Ser Thr Lys Gly His Val Gln Leu Gln
120                 125                 130                 135

cag tct ggg gct gag ctg gtg agg cct ggg gct tca gtg acg ctg tcc      531
Gln Ser Gly Ala Glu Leu Val Arg Pro Gly Ala Ser Val Thr Leu Ser
                140                 145                 150

tgc aag gct tcg ggc tac aca ttt act gac tat gaa ata cac tgg gtg      579
Cys Lys Ala Ser Gly Tyr Thr Phe Thr Asp Tyr Glu Ile His Trp Val
            155                 160                 165

agg cag aca cct gtg cat ggc ctg gaa tgg att gga gct att gat cct      627
Arg Gln Thr Pro Val His Gly Leu Glu Trp Ile Gly Ala Ile Asp Pro
        170                 175                 180

gaa act ggt ggt act gcc tac aat cag aag ttc aag gac aag gcc ata      675
Glu Thr Gly Gly Thr Ala Tyr Asn Gln Lys Phe Lys Asp Lys Ala Ile
    185                 190                 195

gtg act gta gac aaa tcc tcc agc aca gcc tac atg gag ctc cgc agc      723
Val Thr Val Asp Lys Ser Ser Ser Thr Ala Tyr Met Glu Leu Arg Ser
200                 205                 210                 215

ctg aca tct gaa gac tct gcc gtc tat tac tat aca aga tgg ttt gag      771
Leu Thr Ser Glu Asp Ser Ala Val Tyr Tyr Tyr Thr Arg Trp Phe Glu
                220                 225                 230

gac tgg ggc caa ggg act ctg gtc act gtc tct gca atg cgg ggt tct      819
Asp Trp Gly Gln Gly Thr Leu Val Thr Val Ser Ala Met Arg Gly Ser
            235                 240                 245

cat cat cat cat cat cat tagggcctct ctggccgatc ccccgaattt             867
His His His His His His
        250

ccccgatcgt tcaaa                                                     882


<210> SEQ ID NO 48
<211> LENGTH: 846
<212> TYPE: DNA
<213> ORGANISM: mouse
<220> FEATURE:
<221> NAME/KEY: CDS
<222> LOCATION: (25)..(786)

<400> SEQUENCE: 48

ctgcagggta cggccatatt ggcc atg gat gtt gtg atg acc cca aac cca       51
                           Met Asp Val Val Met Thr Pro Asn Pro
                             1               5
```

-continued

```
ctc tcc ctg cct gtc agt ctt gga gat caa gcc tcc atc tct tgc aga       99
Leu Ser Leu Pro Val Ser Leu Gly Asp Gln Ala Ser Ile Ser Cys Arg
 10                 15                  20                  25

tct agt cag agc ctt tta cac agt aat gga atc acc tat tta cat tgg      147
Ser Ser Gln Ser Leu Leu His Ser Asn Gly Ile Thr Tyr Leu His Trp
                30                  35                  40

tac ctg cag aag cca ggc cag tct cca aag ctc ctg atc tac aaa gtt      195
Tyr Leu Gln Lys Pro Gly Gln Ser Pro Lys Leu Leu Ile Tyr Lys Val
            45                  50                  55

tcc aac cga ttt tct ggg gtc cca gac agg ttc agt ggc agt gga tca      243
Ser Asn Arg Phe Ser Gly Val Pro Asp Arg Phe Ser Gly Ser Gly Ser
        60                  65                  70

ggg aca gat ttc aca ctc aag atc agc aga gtg gag gct gag gat ctg      291
Gly Thr Asp Phe Thr Leu Lys Ile Ser Arg Val Glu Ala Glu Asp Leu
     75                  80                  85

gga gtt tat ttc tgc tct caa agt aca cat gtt ccg tac acg ttc gga      339
Gly Val Tyr Phe Cys Ser Gln Ser Thr His Val Pro Tyr Thr Phe Gly
 90                 95                 100                 105

ggg ggg acc aag ctg gaa ata aaa ggc agc acc agc ggc agc ggc aag      387
Gly Gly Thr Lys Leu Glu Ile Lys Gly Ser Thr Ser Gly Ser Gly Lys
                110                 115                 120

ccg ggc agc ggc gag ggc agc acc aag ggc cat gtt caa ctg cag cag      435
Pro Gly Ser Gly Glu Gly Ser Thr Lys Gly His Val Gln Leu Gln Gln
            125                 130                 135

tct ggg gct gag ctg gtg agg cct ggg gct tca gtg acg ctg tcc tgc      483
Ser Gly Ala Glu Leu Val Arg Pro Gly Ala Ser Val Thr Leu Ser Cys
        140                 145                 150

aag gct tcg ggc tac aca ttt act gac tat gaa ata cac tgg gtg agg      531
Lys Ala Ser Gly Tyr Thr Phe Thr Asp Tyr Glu Ile His Trp Val Arg
    155                 160                 165

cag aca cct gtg cat ggc ctg gaa tgg att gga gct att gat cct gaa      579
Gln Thr Pro Val His Gly Leu Glu Trp Ile Gly Ala Ile Asp Pro Glu
170                 175                 180                 185

act ggt ggt act gcc tac aat cag aag ttc aag gac aag gcc ata gtg      627
Thr Gly Gly Thr Ala Tyr Asn Gln Lys Phe Lys Asp Lys Ala Ile Val
                190                 195                 200

act gta gac aaa tcc tcc agc aca gcc tac atg gag ctc cgc agc ctg      675
Thr Val Asp Lys Ser Ser Ser Thr Ala Tyr Met Glu Leu Arg Ser Leu
            205                 210                 215

aca tct gaa gac tct gcc gtc tat tac tat aca aga tgg ttt gag gac      723
Thr Ser Glu Asp Ser Ala Val Tyr Tyr Tyr Thr Arg Trp Phe Glu Asp
        220                 225                 230

tgg ggc caa ggg act ctg gtc act gtc tct gca atg cgg ggt tct cat      771
Trp Gly Gln Gly Thr Leu Val Thr Val Ser Ala Met Arg Gly Ser His
    235                 240                 245

cat cat cat cat cat tagggcctct ctggccgatc ccccgaattt ccccgatcgt      826
His His His His His
250

tcaaacattt ggcaataaag                                                846
```

<210> SEQ ID NO 49
<211> LENGTH: 738
<212> TYPE: DNA
<213> ORGANISM: mouse
<220> FEATURE:
<221> NAME/KEY: CDS
<222> LOCATION: (19)..(687)
<223> OTHER INFORMATION: mature peptide is coded by nucleotides 49 to 687

<400> SEQUENCE: 49

-continued

```
cccgggtacc cttctaga ctc gtg aca gtt gtt gat ggt gcc caa tcc cag        51
                    Leu Val Thr Val Val Asp Gly Ala Gln Ser Gln
                     1               5                  10

gtt caa ctg cag cag tct ggg gct gag ctg gtg agg cct ggg gct tca        99
Val Gln Leu Gln Gln Ser Gly Ala Glu Leu Val Arg Pro Gly Ala Ser
             15                  20                  25

gtg acg ctg tcc tgc aag gct tcg ggc tac aca ttt act gac tat gaa       147
Val Thr Leu Ser Cys Lys Ala Ser Gly Tyr Thr Phe Thr Asp Tyr Glu
         30                  35                  40

ata cac tgg gtg agg cag aca cct gtg cat ggc ctg gaa tgg att gga       195
Ile His Trp Val Arg Gln Thr Pro Val His Gly Leu Glu Trp Ile Gly
     45                  50                  55

gct att gat cct gaa act ggt ggt act gcc tac aat cag aag ttc aag       243
Ala Ile Asp Pro Glu Thr Gly Gly Thr Ala Tyr Asn Gln Lys Phe Lys
 60                  65                  70                  75

gac aag gcc ata gtg act gta gac aaa tcc tcc agc aca gcc tac atg       291
Asp Lys Ala Ile Val Thr Val Asp Lys Ser Ser Ser Thr Ala Tyr Met
                 80                  85                  90

gag ctc cgc agc ctg aca tct gaa gac tct gcc gtc tat tac tat aca       339
Glu Leu Arg Ser Leu Thr Ser Glu Asp Ser Ala Val Tyr Tyr Tyr Thr
             95                 100                 105

aga tgg ttt gag gac tgg ggc caa ggg act ctg gtc act gtc tct gca       387
Arg Trp Phe Glu Asp Trp Gly Gln Gly Thr Leu Val Thr Val Ser Ala
        110                 115                 120

gcc aaa aca aca ccc cca tca gtc tat cca ctg gcc cct ggg tgt gga       435
Ala Lys Thr Thr Pro Pro Ser Val Tyr Pro Leu Ala Pro Gly Cys Gly
    125                 130                 135

gat aca act ggt tcc tct gtg act ctg gga tgc ctg gtc aag ggc tac       483
Asp Thr Thr Gly Ser Ser Val Thr Leu Gly Cys Leu Val Lys Gly Tyr
140                 145                 150                 155

ttc cct gag tca gtg act gtg act tgg aac tct gga tcc ctg tcc agc       531
Phe Pro Glu Ser Val Thr Val Thr Trp Asn Ser Gly Ser Leu Ser Ser
                160                 165                 170

agt gtg cac acc ttc cca gct ctc ctg cag tct gga ctc tac act atg       579
Ser Val His Thr Phe Pro Ala Leu Leu Gln Ser Gly Leu Tyr Thr Met
            175                 180                 185

agc agc tca gtg act gtc ccc tcc agc acc tgg cca agt cag acc gtc       627
Ser Ser Ser Val Thr Val Pro Ser Ser Thr Trp Pro Ser Gln Thr Val
        190                 195                 200

acc tgc agc gtt gct cac cca gcc agc agc acc acg gtg gac aaa aaa       675
Thr Cys Ser Val Ala His Pro Ala Ser Ser Thr Thr Val Asp Lys Lys
    205                 210                 215

ctt gag ccc agc gcggccgctg caggtcttga tcctttcctg ggacccggca          727
Leu Glu Pro Ser
220

agaaccaaaa a                                                          738
```

<210> SEQ ID NO 50
<211> LENGTH: 42
<212> TYPE: DNA
<213> ORGANISM: mouse

<400> SEQUENCE: 50

```
gcactaggtc aagcggccgc ttactaacac tcattcctgt tg                         42
```

<210> SEQ ID NO 51
<211> LENGTH: 753
<212> TYPE: DNA
<213> ORGANISM: mouse
<220> FEATURE:

-continued

<221> NAME/KEY: CDS
<222> LOCATION: (7)..(705)
<221> NAME/KEY: mat_peptide
<222> LOCATION: (67)..(705)

<400> SEQUENCE: 51

```
tctaga atg gta agc gct att gtt tta tat gtg ctt ttg gcg gcg gcg        48
       Met Val Ser Ala Ile Val Leu Tyr Val Leu Leu Ala Ala Ala
       -20                 -15                 -10

gcg cat tct gcc ttt gcg gcg gtt caa ctg cag cag tct ggg gct gag       96
Ala His Ser Ala Phe Ala Ala Val Gln Leu Gln Gln Ser Gly Ala Glu
     -5              -1   1               5                  10

ctg gtg agg cct ggg gct tca gtg acg ctg tcc tgc aag gct tcg ggc      144
Leu Val Arg Pro Gly Ala Ser Val Thr Leu Ser Cys Lys Ala Ser Gly
                15                  20                  25

tac aca ttt act gac tat gaa ata cac tgg gtg agg cag aca cct gtg      192
Tyr Thr Phe Thr Asp Tyr Glu Ile His Trp Val Arg Gln Thr Pro Val
            30                  35                  40

cat ggc ctg gaa tgg att gga gct att gat cct gaa act ggt ggt act      240
His Gly Leu Glu Trp Ile Gly Ala Ile Asp Pro Glu Thr Gly Gly Thr
        45                  50                  55

gcc tac aat cag aag ttc aag gac aag gcc ata gtg act gta gac aaa      288
Ala Tyr Asn Gln Lys Phe Lys Asp Lys Ala Ile Val Thr Val Asp Lys
     60                  65                  70

tcc tcc agc aca gcc tac atg gag ctc cgc agc ctg aca tct gaa gac      336
Ser Ser Ser Thr Ala Tyr Met Glu Leu Arg Ser Leu Thr Ser Glu Asp
 75                  80                  85                  90

tct gcc gtc tat tac tat aca aga tgg ttt gag gac tgg ggc caa ggg      384
Ser Ala Val Tyr Tyr Tyr Thr Arg Trp Phe Glu Asp Trp Gly Gln Gly
                95                 100                 105

act ctg gtc act gtc tct gca gcc aaa aca aca ccc cca tca gtc tat      432
Thr Leu Val Thr Val Ser Ala Ala Lys Thr Thr Pro Pro Ser Val Tyr
            110                 115                 120

cca ctg gcc cct ggg tgt gga gat aca act ggt tcc tct gtg act ctg      480
Pro Leu Ala Pro Gly Cys Gly Asp Thr Thr Gly Ser Ser Val Thr Leu
        125                 130                 135

gga tgc ctg gtc aag ggc tac ttc cct gag tca gtg act gtg act tgg      528
Gly Cys Leu Val Lys Gly Tyr Phe Pro Glu Ser Val Thr Val Thr Trp
    140                 145                 150

aac tct gga tcc ctg tcc agc agt gtg cac acc ttc cca gct ctc ctg      576
Asn Ser Gly Ser Leu Ser Ser Ser Val His Thr Phe Pro Ala Leu Leu
155                 160                 165                 170

cag tct gga ctc tac act atg agc agc tca gtg act gtc ccc tcc agc      624
Gln Ser Gly Leu Tyr Thr Met Ser Ser Ser Val Thr Val Pro Ser Ser
                175                 180                 185

acc tgg acc tgc agc gtt gct cac cca gcc agc agc cca agt cag acc      672
Thr Trp Thr Cys Ser Val Ala His Pro Ala Ser Ser Pro Ser Gln Thr
            190                 195                 200

gtc acc acg gtg gac aaa aaa ctt gag ccc agc tagtaatgag cggccgctgc    725
Val Thr Thr Val Asp Lys Lys Leu Glu Pro Ser
        205                 210

agatctgatc ctttcctggg acccggca                                       753
```

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence:nt 2253 to
2271 of pDAB439

<400> SEQUENCE: 52

-continued

```
tgcatgtgtt ctccttttt                                                 19


<210> SEQ ID NO 53
<211> LENGTH: 44
<212> TYPE: DNA
<213> ORGANISM: Artificial Sequence
<220> FEATURE:
<223> OTHER INFORMATION: Description of Artificial Sequence:nt 4256 to
      4308 of pDAB439

<400> SEQUENCE: 53

ggtacggcca tattggccga gctcggcctc tctggccgat cccc                     44


<210> SEQ ID NO 54
<211> LENGTH: 63
<212> TYPE: DNA
<213> ORGANISM: Artificial Sequence
<220> FEATURE:
<223> OTHER INFORMATION: Description of Artificial Sequence:nt 4744 to
      4807 of pDAB439

<400> SEQUENCE: 54

gcggccgctt taacgcccgg gcatttaaat ggcgcgccgc gatcgcttgc agatctgcat    60

ggg                                                                  63


<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:nt 5417 to
      5436 of pDAB439

<400> SEQUENCE: 55

ggggactcta gaggatccag                                                20


<210> SEQ ID NO 56
<211> LENGTH: 24
<212> TYPE: PRT
<213> ORGANISM: Zea mays

<400> SEQUENCE: 56

Pro Gly Ser Pro Ala Pro Ala Ala Pro Lys Asn Gly Leu Gly Glu Arg
  1               5                  10                  15

Pro Glu Ser Leu Asp Val Arg Gly
             20


<210> SEQ ID NO 57
<211> LENGTH: 12
<212> TYPE: DNA
<213> ORGANISM: Zea mays

<400> SEQUENCE: 57

atggcgctcc gc                                                        12


<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: putative
      N-terminus of the precursor protein

<400> SEQUENCE: 58
```

-continued

```
atggctagcc tccgc                                                          12


<210> SEQ ID NO 59
<211> LENGTH: 4
<212> TYPE: PRT
<213> ORGANISM: Zea Mays

<400> SEQUENCE: 59

Met Ala Leu Arg
  1


<210> SEQ ID NO 60
<211> LENGTH: 5
<212> TYPE: PRT
<213> ORGANISM: Artificial Sequence
<220> FEATURE:
<223> OTHER INFORMATION: Description of Artifical Sequence: putative
      N-terminus of the precursor protein

<400> SEQUENCE: 60

Met Ala Ser Leu Arg
  1               5
```

ANTIBODY-MEDIATED DOWN-REGULATION OF PLANT PROTEINS

RELATED APPLICATION

This application claims the priority of U.S. Provisional Patent Application Ser. No. 60/093,587, filed Jul. 21, 1998.

FIELD OF THE INVENTION

This invention relates to the preparation and use of nucleic acid fragments or genes encoding monoclonal antibodies immunologically reactive to transit peptides and the use of said genes to create transgenic plants having altered protein levels.

BACKGROUND OF THE INVENTION

The modification of plants by genetic engineering has been of considerable interest in recent years. To date, several different plant species have been modified by introducing new genes encoding proteins having enzymatic activity. In essence, presence of these enzymes encoded by transgenes results in the production of proteins which can alter existing plant properties and/or produce new and enhanced characteristics. When said proteins are expressed, new or modified enzymatic activities not previously endogenous to the plant can be observed, or levels of proteins found therein can be increased.

Another genetic approach that has been used to modify plant species is down-regulation of a particular plant protein. Down-regulation can result in either partial or complete elimination of a particular enzymatic activity of choice by decreasing overall steady state levels of the protein associated therewith. A common down-regulation approach used to modify a desired plant enzyme level or activity is antisense RNA technology. Antisense RNA results in down-regulation at the RNA translational level. Down-regulation by antisense RNA, as described in U.S. Pat. No. 5,107,065 to Calgene, has been shown effective with a variety of plant genes as described by Shimada et al., (1993) Theor. Appl. Genet. 86:665–672; Kull, et al., (1995) J. Genet. Breed. 49:67–76; Slabas and Elborough, (1997) WO 97/07222 to Zeneca, published Feb. 27, 1997; and Knutzon et al., (1992) Proc. Natl. Acad. Sci USA 89:2624–2628.

Another down regulation approach involves the use of ribozyme technology as described by Hasselhoff and Gerlach, (1988) Nature 342:76–79. Ribozyme technology, like antisense methodologies, also works at the RNA translational level and involves making catalytic RNA molecules which bind to and cleave the mRNA of interest. Ribozymes have recently been demonstrated as an effective method for the down-regulation of plant proteins as described in WO97/10328 to Ribozyme Pharmaceuticals and Dow AgroSciences, LLC, formally DowElanco.

Co-suppression, as described by Seymour et al., (1993, Plant Mol. Biol. 23:1–9) is another approach applicable for down-regulation of plant gene expression. At present, the precise mechanism of down-regulation via co-suppression is not known. However, it has been used extensively to produce transgenic plants having modified gene expression levels as described in Brusslan et al., (1993) Plant Cell 5:667–677; Vaucheret et al., (1995) Mol. Gen. Genet. 248:311–317; and Jorgensen et al., (196) Plant Mol. Biol. 31:957–973.

As disclosed herein, Applicants have invented an alternative approach to down-regulate proteins in plants relying on the use of monoclonal antibodies (MAb) and functional fragments thereof, such as single chain antibodies (SCAb) that specifically recognize and bind transit peptides. As a result, steady-state levels of corresponding passenger proteins can be reduced. The proposed approach is further exemplified, as shown in the non-limiting examples, through down-regulation of maize stearoyl-ACP Δ-9 desaturase.

In many situations it will be desirable to modify an existing trait of a plant cell rather than introduce a new trait. Thus, one may wish to modify the overall activity levels of a particular enzyme, provide for preferential accumulation of one allele as compared to another, one isozyme as compared to another or the like. In other instances, one may only wish to reduce the amount of expression of a protein encoded by a gene rather than inhibit expression entirely. It is therefore of interest to use the invention disclosed herein which will allow for directed modification of specific proteins in particular plant cells, plant tissues, or plants.

SUMMARY OF THE INVENTION

In the present invention, monoclonal antibodies have been generated against transit peptides that direct plant passenger proteins to organelles. Steady state levels of passenger proteins in plant cells can be altered by expressing antibodies which immunologically react to said transit peptides found attached to said passenger proteins in the precursor form.

One aspect of the invention is identification of transit peptides and genes and nucleic acids encoding the same. Information obtained from said genes and nucleic acids can be used to synthesize transit peptides.

Another aspect of the present invention relates to production of hybridoma cells lines producing monoclonal antibodies immunologically reactive to said transit peptides. Said antibodies can exhibit specificity for and high binding affinity to said transit peptides.

Another aspect of the disclosed invention is related to genes and nucleic acid fragments encoding monoclonal antibodies immunologically reactive to plant transit peptides. Said genes are obtained for the heavy chain and light chain portion of said antibodies.

Yet an additional aspect of the present invention relates to modifying genes encoding said monoclonal antibodies thus designing and expressing single chain antibodies (SCAb) derived therefrom. Said SCAbs can exhibit binding specificity and antigen affinity similar to said monoclonal antibodies but are encoded by a single gene.

An additional aspect of the present invention is the production of chimeric genes encoding monoclonal antibodies and single chain antibodies (SCAb) immunologically reactive to said transit peptides in combination with promoter regulatory elements and use of said chimeric genes within a plant cell. Expression of said genes can result in functional antibody proteins which bind to transit peptides and thus lowers steady state levels of passenger proteins in a cell organelle.

Yet an additional aspect of the present invention is transformation of plant species disclosed herein with said chimeric genes.

Other aspects, embodiments, advantages, and features of the present invention will become apparent from the following specification.

DETAILED DESCRIPTION OF THE INVENTION

The present invention relates to methods and compositions for obtaining transgenic plants having altered steady state passenger protein levels due to expression of antibodies being immunologically reactive to transit peptides. The following phrases and terms are defined below:

By "altered steady state" is meant that the total level of a particular passenger plant protein having a transit peptide in a modified plant is different from that of a normal or non-modified plant under similar conditions. Decreased steady state levels can be achieved by expressing antibodies immunologically reactive to said transit peptide.

By "antibody" is meant a protein molecule having functional activity comprising two identical polypeptide chains of about 600 amino acid residues (usually referred to as heavy chains, H) covalently attached to each other by disulfide bonds, and two identical shorter polypeptide chains of about 220 amino acid residues (usually referred to as the light chains, L) each light chain being covalently attached to each other by disulfide bonds. The term antibody also includes immunologically-active fragments of the above described tetramer, as well as fragments, segments, proteolytically cleaved portions or recombinantly-prepared portions that still maintain antigen binding capacity as disclosed herein.

By "cDNA" is meant DNA that is complementary to and derived from a mRNA.

By "chimeric DNA construction" is meant a recombinant DNA containing genes or portions thereof from one or more species.

By "constitutive promoter" is meant promoter elements that direct continuous gene expression in all cell types and at all times (i.e., actin, ubiquitin, CaMV 35S, 35T, and the like).

By "cosuppression" is meant the introduction of a foreign gene having substantial homology to an endogenous gene, and in a plant cell can cause reduction in activity of the foreign gene and/or the endogenous protein product.

By "developmental specific" promoter is meant promoter elements responsible for gene expression at specific plant developmental stages, such as in early or late embryogenesis.

By "enhancer" is meant nucleotide sequence elements which can stimulate promoter activity such as those from maize streak virus (MSV) and alcohol dehydrogenase intron 1.

By "expression" as used herein, is meant the transcription and stable accumulation of the antibody RNA inside a plant cell.

By "foreign" or "heterologous gene" is meant a gene encoding a protein whose exact amino acid sequence is not normally found in the host cell, but is introduced therein.

By "functional" fragments, and "functional antibodies" is meant that the antibody or fragments thereof retain their ability to bind epitopes used in the immunization process and production of said antibody.

By "gene" is meant to include all genetic material involved in protein expression including chimeric DNA constructions, genes, plant genes and portions thereof.

By "genome" is meant genetic material contained in each cell of an organism and/or virus.

By "indigenous" gene is meant the gene encoding the precursor protein, passenger protein, or transit peptide as found in the native organism. Typically, the transit peptide and passenger protein are found together in the source from which the gene was isolated, although not required to be within the scope of the invention. A non-limiting example of an indigenous gene would be the gene encoding the precursor protein maize Δ-9 desaturase, said gene being found in maize.

By "inducible promoter" is meant promoter elements which are responsible for expression of genes in response to a specific signal, such as: physical stimuli (heat shock genes); light (RUBP carboxylase); hormone (Em); metabolites and stress.

By "mature protein" or "passenger protein" is meant the protein which is found after processing and passing into an organelle. Passenger proteins are originally made in a precursor form that includes a transit peptide and said passenger protein. Upon entry into an organelle, the transit peptide portion is cleaved, thus leaving the "passenger" or "mature" protein. Passenger protein are the proteins typically obtained upon purification from an homogenate, as described herein. The sequence of passenger proteins can be determined as described herein. Passenger proteins can be indigenous in that they are naturally found in the organelle of interest. Passenger proteins can also be non-indigenous in that a plant may be transformed using a heterologous gene encoding a passenger protein not naturally found therein.

By "modified plant" is meant a plant wherein the protein levels or total protein specific activity levels of a passenger protein have been altered relative to that seen in a unmodified plant due to functional activity of an antibody.

By "nucleic acids" is meant to include all forms of DNA and RNA.

By "organelle" or "plant organelle" is meant to include chloroplasts, chromoplast, leucoplast, amyloplast, mitochondria, the nucleus, and the like.

By "phenotypic change" is meant to include alterations in steady state protein levels in a transformed or modified plant due to the expression of an antibody or fragments thereof binding to a organeller transit peptide.

By "plant" is meant a photosynthetic organism including both eukaryotes and prokaryotes.

By "precursor" protein is meant a protein having a transit peptide and a passenger protein covalently attached to each other. The passenger protein and transit peptide can be homologous to each other in that they are encoded in a manner isolated from nature. A non-limiting example could be the native maize transit peptide of Δ-9 desaturase covalently linked to the native maize Δ-9 desaturase passenger protein. In addition, the transit peptide and passenger protein can be heterologous to each other. A non-limiting example could be the native transit peptide for Δ-9 desaturase heterologously attached to the passenger protein gene encoding chlorophyll a/b binding protein.

By "promoter regulatory element" is meant nucleotide sequence elements within a nucleic fragment or gene which control the expression of that nucleic acid fragment or gene. Promoter sequences provide the recognition for RNA polymerase and other transcriptional factors required for efficient transcription. Promoter regulatory elements are also meant to include constitutive, tissue-specific, developmental-specific, inducible promoters and the like. Promoter regulatory elements may also include certain enhancer sequence elements that improve transcriptional efficiency. In addition, promoters and promoter regulatory elements, as used herein, are meant to include subgenomic promoters found in +sense, single-stranded RNA viruses such as tobacco mosaic virus and the like.

By "tissue-specific" promoter is meant promoter elements responsible for gene expression in specific cell or tissue types, such as the leaves or seeds (i.e., zein, oleosin, napin, ACP, globulin and like).

By "transgenic plant" is meant a plant expressing a chimeric gene introduced through transformation efforts.

By "transit peptide" or "signal peptide" is meant those amino acids that direct a passenger protein to a particular organelle as defined herein. It is within the scope of this invention that the transit peptide can be either indigenous or non-indigenous to the plant cell of interest. In addition, as further described herein, the transit peptide can be either homologous or heterologous to the passenger protein of interest in that it is natively found with said passenger protein as isolated from nature (homologous) or not (heterologous).

The present invention is directed to down regulation of organeller proteins by expression of antibodies or functional fragments thereof that are immunologically reactive to transit peptides. Down regulation can result in decreased steady state levels of the passenger proteins or enzymatic activity levels of said passenger proteins. Passenger protein may be homologous or heterologous with respect to the transit peptide. Furthermore, transit peptides may be homologous or heterologous with respect to passenger proteins. Both transit peptides and passenger proteins may be, either together or separately, indigenous or non-indigenous to the plant cell in which they are found.

In plants, chloroplast, mitochondria, the nucleus and other organelles as defined herein, use transit peptides to direct passenger proteins to the appropriate organelle. Transit peptides can be used as antigens, as disclosed herein, in the production of functional antibodies immunoreactive thereto. Said functional antibodies can then be expressed within the cell whereby they can bind to said transit peptides and prevent accumulation of the passenger protein in the organelle and hence the cell. While chloroplast, mitochondria, and the nucleus are the primary organelles found in plant tissue, cells are also likely to have other kinds of organelles including amyloplasts, chromoplast, leucoplast and the like, all of which use transit peptides for protein localization. Therefore, protein uptake can be inhibited in plant organelles by practicing the invention as disclosed herein.

As further disclosed herein, expression of functional antibodies within plant cells which can bind transit peptides can result in decreased steady-state levels of the passenger protein associated therewith when compared to non-transformed plants. Preferably, steady state levels of passenger proteins can be decreased from about 10% to about 90%; more preferably from about 50% to about 90%; with steady state levels of passenger proteins being decreased about 90% compared to non-modified being most preferred.

As further described herein, amino acid, gene, and nucleic acid fragment sequence encoding transit peptides can be used to produced antibodies which can then be used in transgenic applications to produce plants having altered steady-state protein levels. The invention is exemplified by determining the transit peptide sequence of maize stearoyl-ACP Δ-9 desaturase (Δ-9 desaturase) followed by producing, cloning, and expressing functional antibodies having an affinity to the same. In some cases, transit peptide sequences can be determined by comparison of the gene and amino acid sequence encoding for the complete precursor protein as described herein. Preferably, genes and nucleic acid fragments encoding for passenger proteins and the use of said genes to determine nucleic acid fragments and genes encoding transit peptides are isolated from plants. More preferred are those amino acid, gene, and nucleic acid fragments disclosed herein as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 SEQ ID NO:14 and SEQ ID NO:15.

Hybridoma cell lines producing monoclonal antibodies can be obtained as disclosed herein. Said cell line most preferred is 10E10 (Mab-Tp1), which was deposited in accordance with the terms of the Budapest Treaty at the American Type Culture Collection, 10801 University Boulevard, Manassas, Va. 20110-2209, on Jun. 18, 1998 (ATTC Designation HB-12544). Monoclonal antibodies which are immunoreactive to the transit peptides disclosed herein can be produced from hybridoma cell lines. Preferably, the amino acid sequence, gene sequence and nucleic acid fragments encoding precursor proteins, transit peptides, and passenger proteins can be determined. Most preferred are those amino acid, gene and nucleic acid sequences disclosed herein as SEQ ID NO:21, SEQ ID NO:22, SEQ ID NO:24, SEQ ID NO:25, SEQ ID NO:26, SEQ ID NO:27 SEQ ID NO:28 SEQ ID NO:29, SEQ ID NO:30, SEQ ID NO:31, SEQ ID NO:32, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50 and SEQ ID NO:51.

As disclosed herein, the invention relates to identification and production of functional antibodies against transit peptides which direct passenger proteins to organelles. The amino acid sequence and hence the nucleic acid sequence of a transit peptide can be determined in a variety of ways available to the skilled artisan. For example, passenger proteins of interest can be purified using a variety of techniques as disclosed herein. Once purified, amino terminal sequencing of said protein can be determined. The gene encoding said protein can then be cloned. Comparison of the amino acid sequence determined by and from the cDNA to that obtained from amino terminal sequence of the passenger protein will allow determination of the transit peptide sequence. In addition, many transit peptide sequences are available in the art and can easily be obtained from GenBank located at the National Center for Biotechnology Information web site. In plants, transit peptides are typically cleaved and degraded upon entry of the passenger protein into the organelle of interest, therefore, purification of transit peptides from plant tissues is typically not possible.

Transit peptides of the present invention provide intracellular transport to plastids and mitochondria. The subject of transit peptides in plants has been extensively reviewed by Keegstra et al., (1989) Cell, 56:247–253), which is incorporated herein by reference. Typically, there is very little primary amino acid sequence homology between different plant transit peptides. In addition, even though passenger proteins may have amino acid and nucleic acid sequence similarities between cultivars, lines, and species, transit peptides obtained therefrom may show very little amino acid or DNA sequence homology. Furthermore, the length of transit peptides can vary, with some passenger proteins having transit peptides with as little as about 30 amino acid while other can be about 150 amino acids or longer. Nearly all transit peptide amino acid sequences nearly all start with Met-Ala at the amino terminus. The carboxy terminus can often be determined by inspection in that cleavage most often occurs at or near the motif Val-Ala-Val-Val, Val-Ala-Ala-Val or variations thereof. In many cases, transit peptides may also contain further information for organeller targeting. Depending of the source of the transit peptide, precursor proteins may display differences in import behavior, activity and efficiency. These differences are thought not to be only due solely to the transit peptide but also to passenger proteins and interaction associated therewith. Additional descriptions of transit peptide characteristics in plants and mechanisms associated therewith can be found in Pfanner et al., (1988) Eur. J. Biochem, 175:205–212; Ko and Ko, (1992) J. Biol. Chem. 267, 13910–13916; Pfanner et al., (1988) TIBS 13:165–167; Bascomb et al. (1992) Plant Microb. Biotechnol. Res. Ser. 1:142–163; and Bukau et al., (1996) Trends in Cell Biol. 6:480–486; which are incorporated herein by reference.

Transit peptides used to import proteins into the nucleus are also within the scope of this invention. Antibodies can be made against said peptides and used to lower steady state levels of the passenger proteins as disclosed herein. Nuclear transit peptides are typically comprised of short polypeptide regions and can be classified as one of three distinct types. For example, one type possesses a single short region enriched in basic amino acids. Another type is composed of two basic regions separated by a spacer. Finally, a third type possesses both hydrophobic and basic amino acids. Nuclear transit peptides in plants are further described in Silver (1991) Cell 64:489–497; Hicks et al., (1995) Plant Physiol. 107:1055–1058; Ballas and Citovsky, (1997) Proc. Natl. Acad. Sci. USA, 94:10723–10728; Citovsky et al., (1994) Proc. Natl. Acad. Sci. USA (91): 3210–3214; Lyck et al., (1997) Planta, 202:117–125; Reiss et al., (1997) Mol. Gen. Genet. 253:695–702; Sakamoto et al., (1996) Plant J., 10:859–868; and Raikhel (1992) Plant Physiol. 100:1627–1632, which are incorporated herein by reference.

As further described herein, transit peptides once identified can be produced using a variety of methods. Such methods can include heterologous expression in an appropriate system such as *E. coli*, Baculovirus, yeast and the like. The preferred method of peptide production is through chemical synthesis using either t-butyloxycarbonyl (t-BOC) or 9-fluorenylmethoxycarbonyl (FMOC) as described in Baraby and Merrifield (1980) In The Peptides Vol. 2 (E. Gross and Meienhofer, eds) pp.1–284, Academic Press, San Diego, Calif.; and Stewart and Young, (1984) Solid Phase Peptide Synthesis, $2^{nd}$ ed. Pierce Chemical Co., Rockford, Ill., which are incorporated herein by reference.

It is not necessary for the entire transit peptide to be used in antibody production to be within the scope of this invention. Generally, peptides with a length of about 10 to about 15 residues can be used; however, peptides with as few as about 6 and up to about 150 amino acids or more are considered to be within the scope of the invention. Typically, polypeptide fragments rich in hydrophilic amino acids induce the best immunological response. Said hydrophilic amino acids include arginine, aspartic acid, glutamic acid, lysine, serine, asparagine, glutamine, glycine, and proline. However, polypeptide fragments with other amino acids can be used as well.

Antibodies bind to epitope sites based on amino acid/amino acid interactions and are thus highly specific for individual epitope sites. However, as stated herein, there is a distinct lack of amino acid and DNA homology between different transit peptides found in plants. Therefore, the use of antibodies immunologically reactive thereto in one genus, species, cultivar, or line may or may not be immunologically reactive to said transit peptides for the same passenger protein found in another genus, species, cultivar, or line. To ensure function, transit peptides from which the passenger protein of interest is derived are typically sequenced from a variety of species, cultivars, or lines to see if common amino acid motifs can be determined. If so, these common amino acid motifs can be chosen for synthetic peptide and antibody production. If said sites do not exist, individual hybridoma lines for the transit peptide of each passenger protein of interest may be required. This feature is especially important to consider in the production of hybrid crops, said crops being derived from transgenic and/or other parental lines.

Once a transit peptide is synthesized, it can be purified prior to conjugation. A variety of purification methods are available to the artisan including gel filtration, dialysis, reverse phase high performance liquid chromatography, ion exchange chromatography and the like.

After the transit peptide is synthesized and purified it may be desirable to conjugate said peptide with an appropriate carrier protein to increase the immunogenic response. A carrier protein should be a good immunogen and have a sufficient number of amino acid residues with reactive side chains for coupling to the synthetic peptide. Keyhole Limpet haemocyanin (KLH) is commonly used because of its proven efficacy. Other proteins useful as carrier molecules include thyroglobulin, bovine serum albumin, tetanus toxin, and the like.

In addition to the choice of carrier protein, a method of coupling the synthetic peptide (antigen) to the carrier protein can also be selected. Most coupling methods rely on the presence of free amino, sulfhydryl, phenolic, or carboxylic groups. The chosen coupling method can link the transit peptide to the carrier either through the carboxy- or amino terminal residue. A variety of coupling reagents are available to the artisan including glutaraldehyde, Bis-imido esters, bis-diaotized benzidine, m-maleimidobenzoyl-N-hydroxysuccinimide and the like.

In accordance with the present invention, there is provided material suitable for eliciting an immunogenic response in a system of mammalian origin. Preferably, the mammal can be of rat, mouse, horse, goat, rabbit, and the like. Most preferred is wherein a mouse is used for antibody production. Elicitation of said response is typically induced by immunization. Immunization protocols are well known in the art and can vary considerably yet remain effective as described in Current Protocols in Immunology, Edited by John E. Coligan et al., John Wiley & Sons, Inc. (1991), which is incorporated herein by reference. Typically, about 1 μg to 50 μg of antigen are given in emulsions of about 1 mL to about 2 mL for a rat and about one-tenth as much for mice. The first injection of antigen into a host animal may be subcutaneous, intramuscular, intraperitoneal or intravasular. Thereafter, about 1 to about 10 or more booster immunizations may be given at intervals of between about 2 and about 8 weeks. The route of immunization may be varied according to protocol. Immune response elicited following injection is typically monitored by performing western analysis to determine the level of antibody present in the animal's serum using techniques commonly available to one having ordinary skill in the art of immunology. Injections of antigen are typically continued until the immunological response reaches a plateau of maximal response.

After immunization is complete, immune lymphocytes from the immunized animal are typically fused to myeloma cells to generate hybridoma cell lines, which are immortal and produce.monoclonal antibodies. Lymphocytes are generally taken from either lymph node tissue or spleen tissue and are fused to plasmocytoma cells, which are specialized myeloma cells available to the artisan from the American Type Culture Collection, Manassas, Va. In a typical fusion, a suspension of lymphocyte cells is added to the myeloma cells in the presence of a fusogen such as polyethylene glycol (PEG). However, other methods of cell transformation are possible including transformation of myeloma cells with viruses such as Epstein-Barr virus and the like.

After fusion, cells are harvested, diluted, and cultured for a week or more in separate wells containing the appropriate selective agent such as hypoxanthine, aminopterin, and thymidine (HAT) which is capable of extinguishing non-fused cells. Cultured supernatants from said wells can be screened to determine hybridoma growth as well as determine the selectivity and affinity of a given antibody to the antigen. The cells may be screened for the presence of antibodies capable of recognizing selected antigenic determinants by using methods available to the skilled artisan such as solid phase radioimmunoassay, enzyme-linked immunosorbent assays, western analysis, and the like. The cells so selected can then be placed in individual wells as single cell colonies by limiting dilution. Feeder cells (e.g. thymocytes, peritoneal exudate cells, and the like) may be added as necessary. After growing, supernatants therefrom can be characterized for antibody production by rescreening as described herein.

In accordance to the present invention, antibodies may be categorized by class or subclass, depending on which of a number of heavy chain constant domains they possess. Heavy chains are classified according to their constant region: IgA, IgD, IgE, IgG or IgM, with some subclasses among them. Light chains are classified as either kappa or lambda. Categorization of antibodies may be performed using commercially available isotyping kits as disclosed herein.

Once hybridoma cell lines have been established and antibodies have been produced and characterized, the antibodies can be purified for further analysis using a variety of techniques. Such techniques can include the use of Sepharose-protein G columns wherein the antibodies are bound followed by elution with 0.5 M ammonium acetate (pH 3.0) and neutralization with 1 M Tris. Other purification techniques can include the use ammonium sulfate precipitation/size exclusion chromatography, affinity chromatography using protein-A Sepharose, as well as standard ion exchange chromatographic techniques available to the artisan skill in the area of protein biochemistry. For purifying engineered antibodies, affinity tags can be encoded by the DNA so that amino acids are expressed which allow binding to a predetermined matrix. Such tags can include the 6X Histidine motif which can bind to a Ni-Sepharose column, a c-myc tag, and the like.

The amino acid sequence of said antibody can be determined using a variety of methods available to the artisan. Such methods can involve direct protein sequencing using a variety of techniques including Edman degradation, mass spectroscopy, nuclear magnetic resonance, and the like. Other methods to determine amino acid sequence can involve the use of molecular biological techniques whereby the gene encoding said antibodies are cloned and sequenced, as disclosed herein. The determination of amino acid sequence allows the antibody or derivatives thereof to be synthesized using a variety of peptide synthesis methods available to the artisan including solid phase t-butyloxycarbonyl (t-BOC), solid phase 9-fluorenylmethyloxycarbonyl (t-FMOC) methods, as well as methods developed by Geysen et al., (1987, J. Immunnol. Methods, 102:259–274); Houghton et al., (1985, Proc. Natl. Acad. Sci. USA, 82:5131–5135); and the like.

In a preferred embodiment, antibodies can be prepared in vitro from chromosomal DNA, cDNA or synthetic oligonucleotides using molecular biology techniques and heterologous expression systems such as *E. coli*, yeast, Baculoviruses, and the like. Cells or other source material containing DNA or RNA coding for the desired antibody may be isolated. In some instances, it may be desirable to isolate the genomic DNA or mRNA (to generate cDNA) from such source material as described in Goldfein et al., (1987, J. Immunology, 138:940–944). When significant levels of nucleic acids are not available, one can use polymerase chain reactions (PCR) to isolate nucleic acid fragments encoding the antibody of choice, as disclosed herein.

If the amino acid sequence has been previously determined using methods disclosed herein or others available to the skilled artisan, the genetic code can be used to reverse translate said amino acid sequence into a DNA sequence. A series of oligonucleotides ranging from about 20 to about 50 bases or more can then be synthesized in order to provide a series of overlapping fragments. The synthesized oligonucleotides can be annealed and ligated to create the gene encoding said antibody.

The complete genomic sequence of a particular antibody may be obtained by screening of a genomic or cosmid library with a probe. Probes can be considerably shorter than the entire gene sequence, but should be at least about 10 nucleotides, preferably at least about 15 nucleotides, more preferably at least about 20 or so nucleotides in length. Longer oligonucleotides up to the full length of the gene encoding the polypeptide of interest are also useful. Both DNA and RNA can be used as probes. In use, probes are typically labeled with $^{32}P$, biotinylated, and the like in a manner that allows for detection thereof. Said probes are often incubated with single stranded DNA from the source of which the gene is desired. Hybridization, or the act of the probe binding to the DNA, is detected usually after binding using nitrocellulose paper or nylon membranes by means of the label on said probe. Hybridization techniques are well known to the person skilled in the art of molecular biology. Thus, antibody genes may be so isolated.

In a preferred embodiment, mRNA can easily be isolated from hybridoma cell lines expressing the antibody of interest using a variety of well known methods. Continually culturing said lines in conjunction with limiting dilutions as disclosed herein effectively results in a monoculture whereby cDNA obtained therefrom essentially encodes for only one antibody. After isotyping said antibody, use of oligonucleotide primers corresponding to constant regions found therein allows for the cloning thereof without necessarily proceeding through the steps common to other cloning procedures such as creation of libraries in phagemids, cosmids, and the like. Once cloned, the cDNA can be sequenced and the amino acid sequence can be determined via the genetic code.

One may engineer an antibody heavy chain or light chain variable region effectively homologous to the antibody heavy chain or light chain variable region of a known antibody. The term "effectively homologous" refers to the concept that the primary amino acid sequence of the variable region may be altered yet the antibody may retain a functional binding site with the capacity to bind to the same antigen or epitope. Accordingly, such variations and derivations are considered to be within the scope of the present invention. Antibodies so engineered may be experimentally determined using cross-blocking techniques wherein binding of one antibody prevents binding of a second antibody to the same epitope through either local or distant steric hindrance.

Modifications contemplated by the present invention include the addition, deletion, or conservative substitution of a limited number of various amino acids. Generally, an amino acid sequence is effectively homologous to a second amino acid sequence if at least about 70 percent, preferably at least about 80 percent, and most preferably, at least about 90 percent of the amino acid sequence of the variable portions of the two antibodies in question are homologous. Conservative substitutions are those exemplified such as glutamic acid and aspartic acid; valine, leucine, and isoleucine; asparagine and glutamine; threonine and serine; glycine and alanine; phenylalanine, tyrosine, and tryptophan; and lysine and arginine. Accordingly, such variations and derivations are considered to be within the scope of the present invention.

Binding affinities between the original and homologous antibody to the antigen of choice can also be used to determine "effective homology" Effectively homologous antibodies would be expected to have antibody:antigen binding constants that are at least within about 3 orders of magnitude compared to the original antibody, and more preferably binding constants that are within about 2 orders of magnitude relative to the original antibody, with binding constants essentially the same as the original antibody being most preferred. Determination of antibody binding constants is well known in the art.

Fragments of antibodies which maintain their ability to bind to the antigen are considered functional and thus considered to be within the scope of the present invention. Said fragments include segments which are generated upon proteolytic cleavage or recombinantly prepared portions thereof. Thus, for example, portions of variable and constants domains of the antibody may be specifically altered or partially or completely omitted. Nonlimiting examples of such recombinant fragments include Fab, $F(ab)_2$, and Fv fragments as described in U.S. Pat. No. 4,642,334 to Moore and U.S. Pat. No. 4,816,567 to Genentech. In addition, antibodies may be modified to form single chain Fv molecules as described in U.S. Pat. No. 4,946,778 to Genex Corp. and as disclosed herein. Said fragments and modifications thereto can also be created by manipulating genes encoding said fragments as disclosed herein. Recombinant constructs containing nucleic acid sequences encoding a functional antibody of interest or fragments thereof and heterologous nucleic acid sequences may be prepared. By heterologous is meant any sequence which is not naturally found joined to the antibody sequence. Hence, by definition, a DNA sequence joined to a sequence not naturally found in a gene encoding an antibody is considered to be heterologous.

Constructs may be designed to produce antibodies of interest or functional fragments thereof in either prokaryotic or eukaryotic cells. The expression of antibodies in a plant cells is of special interest. Moreover, the nucleic acid sequences encoding said antibodies may be integrated into a plant host genome. By transcribing and translating nucleic acid sequences encoding said antibodies or functional fragments thereof in a plant host, said plant is expected to exhibit properties wherein steady state passenger protein levels associated with a gene transit peptide are lower than that observed in the non-transformed plant under similar conditions.

The scope of the invention as disclosed herein relates to decreased steady state levels of passenger proteins being targeted to organelles. A wide variety of modifications may be made in numerous types of plants. Preferred monocotyledonous plants, for example, include rice, corn, wheat, barley, oats, rye and sorghum. Examples of preferred dicotyledonous plants included canola, pea, soybean, sunflower, tobacco, cotton, sugar beet, petunia, tomato, broccoli, lettuce, apple, plum, orange, and lemon.

Modification to plants using the invention as disclosed herein may include varying the steady state protein levels involved in fatty acid distribution of a fatty acid source, such as rapeseed, Cuphea, corn, soybean, canola or any oilseed crop of interest. Antibodies can also be made against the transit peptide of passenger proteins such as Δ-9 desaturase, palmitoyl-ACP thioesterase, β-ketoacyl-ACP synthase, oleyl-ACP thioesterase, and the like. Antibodies can also be made against the transit peptide of proteins such as chlorophyll a/b binding proteins as a way to reduce chlorophyll content. Other organeller localized proteins having transit peptides, of which antibodies can be made using said transit peptide as an antigen as disclosed herein, include: NADPH+ dependent glyceraldehyde-3-phosphate dehydrogenase, early light inducible protein, clip protease regulatory protease, pyruvate orthophosphate dikinase, chlorophyll a/b binding protein, triose phosphate-3-phosphoglycerate phosphate translocator, 5-enol pyruval shikimate-3-phosphate synthase, dihydrofolate reductase, thymidylate synthase, acetyl-coenzyme A carboxylase, Cu/Zn superoxide dismutase, cysteine synthase, rubisco activase, ferritin, granule bound starch synthase, pyrophosphate, glutamine synthase, aldolase, glutathione reductase, nitrite reductase, 2-oxoglutarate/malate translocator, ADP-glucose pyrophosphorylase, ferrodoxin, carbonic anhydrase, polyphenol oxidase, ferrodoxin NADP=oxidoreductase, platocyannin, glycerol-3-phosphate dehydrogenase, lipoxygenase, o-acetylserine (thiol)-lysase, acyl carrier protein, 3-deoxy-D-arabino-heptulosonate 7-phosphate synthase, chloroplast-localized heat shock protein, starch phosphorylase, pyruvate orthophosphate dikinase, starch glycosyltransferase, and the like.

It is within the scope of the present invention that the steady state levels of passenger proteins can be decreased by transforming a plant cell with a gene encoding an antibody directed to the transit peptide associated with said passenger protein in a precursor protein form. It is also within the scope of this invention that transit peptides can be homologous or heterologous to the passenger protein as described herein. As further disclosed herein, transit peptides can be either indigenous or non-indigenous to the transformed plants. In a like manner, passenger proteins can be either indigenous or non-indigenous to the transformed plant cell.

Transit peptides and passenger proteins can be heterologous to each other in that they may not be associated in a manner found in nature. For example, the transit peptide from the small subunit of Rubisco (SSU) can be used to place a variety of proteins in the chloroplast of a plant cell thus causing proteins not normally found to accumulate therein. Antibodies reactive against SSU transit peptide would be expected to prevent accumulation and decrease steady state levels of passenger proteins associated therewith relative to non-transformed controls.

To obtain high expression of heterologous genes in plants it may be preferred to reengineer said genes so that they are more efficiently expressed in the cytoplasm of plant cells. Maize is one such plant where it may be preferred to reengineer the heterologous gene(s) prior to transformation to increase the expression level thereof in said plant. Therefore, an additional step in the design of genes encoding antibodies for plant expression may involve reengineering of a heterologous gene for optimal expression.

One reason for the reengineering an antibody gene for expression in maize is to ensure the optimal G+C content of the native gene as well as eliminate any sequences mimicking or duplicating plant gene control sequences. The presence of some A+T-rich sequences within the DNA of gene(s)

introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one aspect in the design of genes encoding an antibody gene for maize expression, more preferably referred to as plant optimized gene(s), is to generate a DNA sequence having a higher G+C content, and preferably one close to that of maize genes coding for metabolic enzymes. Another goal in the design of the plant optimized gene(s) is to generate a DNA sequence in which the sequence modifications do not hinder translation.

The table below (Table 1) illustrates how high the G+C content is in maize. For the data in Table 1, coding regions of the genes were extracted from GenBank (Release 71) entries, and base compositions were calculated using the MacVector™ program (IBI, New Haven, Conn.). Intron sequences were ignored in the calculations.

Due to the plasticity afforded by the redundancy of the genetic code (i.e., some amino acids are specified by more than one codon), evolution of the genomes in different organisms or

- classes of organisms has resulted in differential usage of redundant codons. This "codon bias" is reflected in the mean base composition of protein coding regions. For example,
- organisms with relatively low G+C contents utilize codons having A or T in the third position of redundant codons, whereas those having higher G+C contents utilize codons having
  - G or C in the third position. It is thought that the presence of "minor" codons within a mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

In reengineering genes encoding an antibody for maize expression, the codon bias of the plant has been determined. The codon bias for maize is the statistical codon distribution that the plant uses for coding its proteins and the preferred codon usage is shown in Table 2. After determining the bias, the percent frequency of the codons in the gene(s) of interest is determined. The primary codons preferred by the plant should be determined as well as the second and third choice of preferred codons. Afterwards, the amino acid sequence of the gene of interest is reverse translated so that the resulting nucleic acid sequence codes for exactly the same protein as the native gene wanting to be heterologously expressed. The new

TABLE 1

Compilation of G + C contents of protein coding regions of maize genes.

| Protein Class[a] | Range % G + C | Mean % G + C[b] |
|---|---|---|
| Metabolic Enzymes (76) | 44.4–75.3 | 59.0 (±8.0) |
| Structural Proteins (18) | 48.6–70.5 | 63.6 (±6.7) |
| Regulatory Proteins (5) | 57.2–68.9 | 62.0 (±4.9) |
| Uncharacterized Proteins (9) | 41.5–70.3 | 64.3 (±7.2) |
| All Proteins (108) | 44.4–75.3 | 60.8 (±5.2) |

[a]Number of genes in class given in parentheses.
[b]Standard deviations given in parentheses.
[c]Combined groups mean ignored in mean calculation.

DNA sequences are designed using codon bias information so that they correspond to the most preferred codons of the desired plant. The new sequences are then analyzed for restriction enzyme sites that might have been created by the modifications. The identified sites are further modified by replacing the codons with second or third choice with preferred codons. Other sites in the sequence which could affect transcription or translation of the gene of interest are the exon:intron 5' or 3' junctions, poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

It is preferred that the plant optimized gene(s) encoding an antibody contain about 63% of first choice codons, between about 22% to about 37% second choice codons, and between about 15% to about 0% third choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The preferred codon usage for engineering genes for maize expression are shown in Table 2. The method described above enables one skilled in the art to modify gene(s) that are foreign to a particular plant so that the genes are optimally expressed in plants. The method is further illustrated in pending PCT application WO 97/13402, which is incorporated herein by reference.

In order to design plant optimized genes, the amino acid sequence of the antibody of interest is reverse translated into a DNA sequence utilizing a non-redundant genetic code established from a cadon bias table compiled for the gene sequences for the particular plant, as shown in Table 2. The resulting DNA sequence, which is completely homogeneous in codon usage, is further modified to establish a DNA sequence that besides having a higher degree of codon diversity, also contains strategically placed restriction enzyme recognition sites, desirable base composition, and a lack of sequences that might interfere with transcription of the gene or translation of the product mRNA.

In designing an antibody gene for optimal plant expression, it may be necessary to add nucleic acid sequences encoding amino acids that have been proven to increase the expression levels thereof. For example, Schouten et al., (1996, Plant Molecular Biology, 30:781–793) have shown that the carboxy-terminal amino acid sequence KDEL increased antibody accumulation in transgenic tobacco. Other strategies for increasing expression of antibody genes have been explored by Owen et al., (1992, Chem. Ind., 11:406–408); Ma (1995, ACS Symp. Ser., 604:56–59); Schouten et al., (1997 FEBS Lett. 415:235–241); Conrad and Fiedler, (1994, Plant Mol. Biol. 26:1023–1030); Fiedler et al., (1997, Immunotechnology 3:205–216); van Engelen et al., (1994, Plant Mol. Biol. 26:1701–1710); Hiatt et al., (1989, Nature 342: 76–78); Firek et al., (1993, Plant Mol. Biol. 23:861–870); Ma et al., (1994, Eur. J. Immunol. 24:131–138), which are incorporated herein by reference.

In another aspect of the invention, genes encoding the antibodies are expressed from transcriptional units inserted into the plant genome. Preferably, said transcriptional units are recombinant vectors capable of stable integration into the plant genome and selection of transformed plant lines expressing mRNA encoding for said antibodies are expressed either by constitutive or inducible promoters in the plant cell. Once expressed, mRNA is translated into proteins, thereby incorporating amino acids of interest. Genes encoding antibodies expressed in plant cells can be under the control of a constitutive promoter, a tissue-specific promoter, an inducible promoter, and the like. Several techniques exist for introducing foreign recombinant vectors into plant cells, and for obtaining plants that stably maintain and express the introduced gene. Such techniques include acceleration of genetic material coated onto microparticles directly into cells (U.S. Pat. No. 4,945,050 to Cornell and U.S. Pat. No. 5,141,131 to DowElanco, now Dow AgroSciences, LLC). In addition, plants may be transformed using Agrobacterium technology, see U.S. Pat. No. 5,177, 010 to University of Toledo, U.S. Pat. No. 5,104,310 to Texas A&M, European Patent Application 0131624B1, European Patent Applications 120516, 159418B1 and 176, 112 to Schilperoot, U.S. Pat. Nos. 5,149,645, 5,469,976, 5,464,763 and 4,940,838 and 4,693,976 to Schilperoot, European Patent Applications 116718, 290799, 320500 all to Max Planck, European Patent Applications 604662, 627752 and U.S. Pat. No. 5,591,616 to Japan Tobacco, European Patent Applications 0267159, and 0292435 and U.S. Pat. No. 5,231,019 all to Ciba Geigy, now Novartis, U.S. Pat. Nos. 5,463,174 and 4,762,785 both to Calgene, and U.S. Pat. Nos. 5,004,863 and 5,159,135 both to Agracetus. Other transformation technology includes whiskers technology, see U.S. Pat. Nos. 5,302,523 and 5,464,765 both to Zeneca. Electroporation technology has also been used to transform plants, see WO 87/06614 to Boyce Thompson Institute, U.S. Pat. No. 5,472,869 and 5,384,253 both to Dekalb, WO09209696 and WO9321335 both to Plant Genetic Systems. Furthermore, viral vectors can also be used in produce transgenic plants expressing the protein of interest. For example, monocotyledonous plant can be transformed with a viral vector using the methods described in U.S. Pat. No. 5,569,597 to Mycogen and Ciba-Giegy, now Novartis, as well as U.S. Pat. Nos. 5,589,367 and 5,316,931, both to Biosource. All of these patents and publications on transformation are incorporated herein by reference.

As mentioned previously, the manner in which the DNA construct is introduced into the plant host is not critical to this invention. Any method which provides for efficient transformation may be employed. For example, various methods for plant cell transformation are described herein and include the use of Ti or Ri-plasmids and the like to perform Agrobacterium mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation.

Where Agrobacterium is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the Agrobacterium host is not critical to this invention. The Ti or Ri plasmid containing the T-DNA for recombination may be capable or incapable of causing gall formation, and is not critical to said invention so long as the vir genes are present.

TABLE 2

Preferred amino acid codons for proteins expressed in maize.

| Amino Acid | Codon* |
|---|---|
| Alanine | GCC/GCG |
| Cysteine | TGC/TGT |
| Aspartic Acid | GAC/GAT |
| Glutamic Acid | GAG/GAA |
| Phenylalanine | TTC/TTT |
| Glycine | GGC/GGG |
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |
| Tryrosine | TAC/TAT |
| Stop | TGA/TAG |

*The first and second preferred codons for maize.

In some cases where Agrobacterium is used for transformation, the expression construct being within the T-DNA borders will be inserted into a broad spectrum vector such as pRK2 or derivatives thereof as described in Ditta et al., (PNAS USA (1980) 77:7347–7351 and EPO 0 120 515, which are incorporated herein by reference. Included within the expression construct and the T-DNA will be one or more markers as described herein which allow for selection of transformed Agrobacterium and transformed plant cells. The particular marker employed is not essential to this invention, with the preferred marker depending on the host and construction used.

For transformation of plant cells using Agrobacterium, explants may be combined and incubated with the transformed Agrobacterium for sufficient time to allow transformation thereof. After transformation, the agrobacteria are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage may not always be necessary. After shoot formation, said plant cells can be transferred to medium which encourages root formation thereby completing plant regeneration. The plants may then be grown to seed and said seed can be used to establish future generations. Regardless of transformation technique, the antibody gene is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue which is contacted with the foreign genes may vary as well. Such tissue would include but would not be limited to embryogenic tissue, callus tissue types I, II, and III, hypocotyl, meristem, root tissue and the like. Almost all plant tissues may be transformed during cellular dedifferentiation using appropriate techniques described herein.

Another variable is the choice of a selectable marker. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialophos); imidazolinones, sulfonylureas and triazolopyrimidine herbicides, such as chlorsulfuron; bromoxynil, dalapon and the like.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Wising et al. (1988) Ann. Rev. Genetics, 22:421, which is incorporated herein by reference. Preferred reporter genes include the beta-glucuronidase (GUS) of the uida locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (1987 Biochem. Soc. Trans. 15, 17–19) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see WO 97/13402 published Apr. 17, 1997) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters and tissue specific promoters.

Other elements such as matrix attachment regions, scaffold attachment regions, introns, enhancers, polyadenylation sequences, and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, the maize streak virus coat protein leader sequence, as well as others available to a skilled artisan.

Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin, and the like) and these may also be used.

Promoter regulatory elements may also be active during a certain stage of the plants' development as well as active in plant tissues and organs. Examples of such include but are not limited to pollen-specific, embryo specific, corn silk specific, cotton fiber specific, root specific, seed endosperm, fruit-specific, specific promoter regulatory elements and the like. Under certain circumstances it may be desirable to use an inducible promoter regulatory element, which is responsible for expression of genes in response to a specific signal, such as: physical stimulus (heat shock genes); light (RUBP carboxylase); hormone (Em); metabolites; chemical; and stress. Other desirable transcription and translation elements that function in plants may be used.

The present invention also contemplates the use of transformed plants which are selfed to produce an inbred plant. The inbred plant can produce seed containing genes encoding antibodies. The inbred lines can also be crossed with other inbred lines to produce hybrids. Parts obtained from the regenerated plant, as flowers, seeds, leaves branches, fruit and the like are covered by the invention provided that said parts contain genes encoding and/or express the antibody of interest. Progeny and variants, and mutants of the regenerated plants are also included within the scope of the invention.

In diploid plants, typically one parent may be transformed and the other parent maybe wild type. After crossing the parents, the first generation hybrids ($F_1$) can be selfed to produce second generation hybrids ($F_2$). Those plants expressing the highest levels of the antibody or having the desired phenotype can be chosen.

Another way to generate plants expressing active antibodies is to transform two plant lines, one with a gene encoding either a heavy chain or light chain and the other plant with the complimentary chain. The two or more plant lines can then be crossed to create progeny contain both heavy chain and light chain components. Functional antibodies can be obtained in this manner as described by Ma et al., (1995) Science 268:716–719.

Plant RNA viral based systems can also be used to express the antibody genes for the purposes as disclosed herein. In so doing, the gene can be inserted into the coat protein region of a suitable plant virus which will infect the host plant of interest. The antibody can then be expressed thus modifying steady state passenger protein levels. Plant RNA viral based systems are described in U.S. Pat. No. 5,500,360 to Mycgoen Plant Sciences, Inc. and U.S. Pat. Nos. 5,316,931 and 5,589,367 to Biosource Genetics Corp. which are incorporated herein by reference.

Standard and molecular biology techniques may be used to clone and sequence the toxins described herein. Additional information may be found in Sambrook, J., Fritsch, E. F., and Maniatis, T. (1989), Molecular Cloning, A Laboratory Manual, Cold Spring Harbor Press, which is incorporated herein by reference.

The invention is illustrated in further details by the following non-limiting examples. The examples are for the purpose of illustration only and are not to be construed as limiting the scope of the present invention.

EXAMPLE 1

Isolation and Cloning of Stearoyl-ACP Δ-9 Desaturase (Δ-9 Desaturase) from Maize A cDNA clone encoding maize stearoyl-ACP Δ-9 desaturase (Δ-9 desaturase) was obtained from a cDNA library derived from maize kernels of inbred CS608 (Mycogen Seeds, San Diego, Calif.) that had been grown in a greenhouse and hand pollinated. The cDNA library was prepared from said kernels harvested at 20 days after pollination, hereinafter 20-DAP. Upon harvest, embryos were immediately collected, frozen on dry ice, and stored at −70° C. RNA was extracted by grinding 2.5 g to a fine powder in liquid nitrogen. Afterwards, 10 mL of extraction buffer [50 mM Tris-HCl, pH 8.0, 4% para-amino salicyclic acid (Sigma Chemical Co), 1% tri-iso-propylnaphtalenesulfonic acid (Eastman Kodak Co., Rochester, N.Y.), 10 mM DTT, and 10 mM sodium meta-bisulfite (Sigma Chemical Co., St. Louis, Mo.)] was added and the mixture was homogenized for 1 min using a TEKMAR TISSUMIZER (Tekmar Co., Cincinnati, Ohio). The homogenate was extracted with an equal volume of phenol equilibrated with 0.1 M Tris-HCl, pH 8.0. Organic and aqueous phases were separated by centrifugation at 4° C. The aqueous phase was removed and extracted with an equal volume of chloroform/octanol (24:1). The supernatant was then transferred, centrifuged, transferred again, and a one-half volume of 7.5 M ammonium acetate (pH 8.0) was added. RNA was then precipitated on ice for 30 min.

Precipitated RNA was collected by centrifugation and dissolved in 1 mL of diethylpyrocarbonate-treated water (0.1% v/v), hereinafter DEPC-water. One-half volume of 7.5 M ammonium acetate (pH 8.0) and two volumes of 100% ethanol were added and the RNA was allowed to precipitate at −20° C. for 30 min. The precipitate was collected by centrifugation, washed in ice-cold 70% ethanol, air dried, and dissolved in 0.5 mL DEPC-treated water.

PolyA$^+$ mRNA was purified on oligo dT-cellulose (Collaborative Biomedical Products, Bedford, Mass.) columns. Type 3 oligo-dT cellulose (0.1 g) was equilibrated in 5 mL of buffer 1 for 30 min, where buffer 1 was loading buffer with 0.5 M NaCl and loading buffer was 20 mM Tris-HCl, pH 7.6, 1 mM EDTA, and 0.1% sodium lauryl sulfate (SDS). The column was washed with 3 volumes of DEPC-water, 3 volumes of wash buffer [0.1 N NaOH, 5 mM EDTA], 3 volumes of DEPC-water, and 5 volumes of buffer 1. The dissolved RNA pellet was heated at 65° C. for 5 min, diluted 2× with buffer 2 [2×loading buffer] and then applied to the oligo-dT column. The flow through material was then collected, reheated, and reapplied to the column. Following, the column was washed with 10 volumes of buffer 1 followed by 10 volumes of buffer 3 [loading buffer having 0.1 M NaCl]. PolyA$^+$ RNA was eluted with 3 volumes of elution buffer [10 mM Tris-HCl, pH 7.5, 1 mM EDTA, 0.05% SDS] and collected in 0.5 mL fractions. RNA fractions were combined, buffered to 0.3 M sodium acetate pH 5.2, and precipitated at −20° C. for 16 h after addition of 2.2 volumes of 100% ethanol. The precipitate was collected by centrifugation, washed with 70% ethanol, dried, and dissolved in 50 pL DEPC-treated water. This material was then repurified on a fresh oligo-dT column as described herein to produce highly-enriched polyA$^+$ mRNA. RNA concentrations were determined by measuring $OD_{260\ nm}$.

Five μg of polyA$^+$ RNA was converted to cDNA and cloned into the LAMBDA UNI-ZAP vector using the Lambda ZAP-cDNA synthesis and cloning kit according to the manufacturers protocols (Stratagene, La Jolla, Calif.). The resulting library had an original titer of $3.38\times10^{10}$ plaque forming units/mL (pfu/mL), greater than 95% recombinants and an average insert size of 1.35 kb. The cDNA library was amplified according to Sambrook et al., (Molecular Cloning, A Laboratory Manual, 2$^{nd}$ Ed. (1989) Cold Spring Harbor Laboratory Press) and had a titer of $6.0\times10^6$ pfu/mL. Total library cDNA was batch rescued and isolated as follows: 5 mL of XL1 Blue *E. coli* cells (Stratagene) at $OD_{600nm}$=1.0 in 10 mM $MgSO_4$ were mixed with 8.3 μL ($5\times10^8$ pfu) of amplified embryo cDNA library phage-stock, and 100 μL EXASSIST helper phage (Stratagene) and incubated at 37° C. for 20 min. Twenty-five mL of TY medium [8.0 g/L tryptone, 5.0 g/L yeast extract, and 2.5 g/L NaCl, pH 7.8] were added and cells were incubated at 37° C. for 3 h while shaking. Afterwards, bacterial cells were heat killed at 68° C. for 15 min and the supernatant was recovered. Five hundred μL supernatant was mixed with 14.5 mL of SOLR cells (Stratagene) ($OD_{600nm}$=1.5), incubated at 37° C. for 15 min, added to 500 mL LB [10 g/L tryptone, 10 g/L NaCl, and 5 g/L yeast extract containing 50 μg/mL Ampicillin], and grown overnight. Afterwards, plasmid DNA was obtained by alkaline lysis/CsCl purification, according to Sambrook et al (Molecular Cloning, A Laboratory Manual, 2$^{nd}$ Ed. (1989) Cold Spring Harbor Laboratory Press), which is incorporated by reference, and analyzed by agarose gel electrophoresis following digestion with EcoRI/XhoI. A smear ranging from 0.5 to 3.0 kb was observed following electrophoresis.

To isolate a clone encoding maize Δ-9 desaturase, a DNA fragment was amplified using polymerase chain reaction technology, hereinafter PCR, to produce a probe which could be used to isolate a full length cDNA. A 5' primer with 128-fold degeneracy and a 3' primer with 128-fold degeneracy, entered herein as SEQ ID NO:1 and SEQ ID NO:2, respectively, were synthesized on an Applied Biosystems High-Throughput DNA Synthesizer Model 394 (Foster City, Calif.). Double stranded cDNA was used as template. PCR amplification was performed as follows: 10 ng template DNA, 5 μL 10×reaction buffer, hereinafter 10×RB, [100 mM Tris-HCl pH 8.3, 500 mM KCl, 15 mM $MgCl_2$, 0.01% (w/v) gelatin], 5 μL of 2 mM deoxyribose nucleotides triphosphate (dNTPs), 50 pmole primers (SEQ ID NO:1 and SEQ ID NO:2), 2.5 units AMPLITAQ DNA Polymerase (Perkin-Elmer, Norwalk, Conn.) and water for a total volume of 50 μL. A DNA Thermal Cycler (Perkin-Elmer Cetus Model #9600, Norwalk, Conn.) was programmed as follows: 96° C. for 1 min; followed by [94° C. (1 min), 37° C. (2 min), and 72° C. (3 min)] for 35 cycles; followed by 7 min at 72° C. A DNA product of 276 base pairs (bp) was obtained, sequenced as described, infra, and entered herein as SEQ ID NO:3.

The PCR fragment was cloned directly into the pBC vector (Stratagene, LaJolla, Calif.) and transformed into One Shot™ INVaF' competent cells (Invitrogen) according to manufacturers specifications. The DNA was extracted using the Qiawell Plasmid Purification System (Qiagen, Santa Clarita, Calif.) according to the manufacturer's instructions. Recombinant clones were sequenced by dideoxy chain termination using PRISM AMPLITAQ READY REACTION DYEDEOXY Terminator cycle sequencing kit #401384 according to the manufacturer (Perkin-Elmer, Applied Biosystems Division, Foster City, Calif.). Samples were run on an ABI373A automated DNA sequencer (Perkin-Elmer, Applied Biosystems Division). DNA sequence analysis of SEQ ID NO:3 was performed using MACVECTOR v. 4.1.4 (Oxford Molecular, Campbell, Ky.), which gave theoretical translations and alignments thus generating the amino acid sequence entered herein as SEQ ID NO:4.

The CS608 embryo cDNA library described herein was screened using a DNA fragment which was essentially SEQ ID NO:3. This fragment was used to obtain full length clones encoding maize Δ-9 desaturase. Probe DNA was obtained by digesting the cloned PCR fragment (SEQ ID NO:3) with the appropriate restriction enzymes. This material was then run on a preparative 1% agarose gel, the band was excised and the DNA was extracted with QIAEX (Qiagen). An $\alpha^{32}$P-deoxyribocytosine triphosphate (dCTP)-labeled probe was generated using QUICKPRIME Random Labeling kit (Stratagene, LaJolla, Calif.) according to the manufacturer instructions using 5 μL of [$\alpha^{32}$P]-dCTP (3000 Ci/mmole, 10 μCi/μL, DuPont, NEN Life Science Products, Boston, Mass.). Afterwards, the labeling reaction was applied to a NucTrap column (Stratagene) equilibrated with TE [10 mM Tris-HCl, pH 8.0, 1 mM EDTA]. Labeled DNA was eluted with 2 volumes of TE (400 μL each). The probe was heat denatured before being added to hybridization buffer as described herein.

Methods for phage titering, plating, coring and rescuing were as described in the LAMBDA ZAP II Library (Stratagene) instruction manual. The cDNA library was plated (100,000 pfu/plate) on five 22.5×22.5 cm NUNC assay plates (Nunc Inc. Roskilde, Denmark). Duplicate phage lifts were taken from each plate using 0.45 μm Hybond N+ nylon membranes (Amersham, Arlington Heights, Ill.). Following transfer of the phage to the filters, cells and phage were denatured and DNA was fixed to the membranes by autoclaving for 8 min at 125° C. followed by UV-crosslinking using a STRATALINKER UV Crosslinker (Stratagene).

Prior to hybridization, filters were extensively washed in 2×SSC [1×SSC is 150 mM NaCl, 15 mM sodium citrated, pH 7.0] 0.1% sodium dodecyl sulfate (SDS) at 65° C. Filter prehybridization was performed at 42° C. for 1 h in 200 mL hybridization buffer containing 50% (v/v) formamide, 3×SSC, 10×Denhardt's solution [1×Denhardt's solution is 0.02% Ficoll (Type 400, Pharmacia), 0.02% polyvinylpyrollidone, and 0.02% bovine serum albumin], 0.1% (w/v) SDS, and 100 μg/mL sheared and denatured salmon sperm DNA. Afterwards, used hybridization buffer was replaced with 100 mL of fresh hybridization buffer containing labeled probe (final activity =$6.1\times10^6$ dpm/mL). Hybridization continued for 18–20 h at 42° C. with gentle rotation. Afterwards, filters were washed twice at room temperature for 40 min in 100 mL of wash solution containing 0.1×SSC and 0.1% SDS, followed by 3–1 h washes with 1 L of the same at 60° C., followed by 2–1 h washes with 2 L of the same at 60° C. Filters were then exposed to Kodak XOMAT-AR Film (Eastman Kodak Company, Rochester, N.Y.) with intensifying screens (Lightening Plus, DuPont CRONEX, DuPont, Wilmington Del.) for 16 h at −70° C. Examination of films allowed the identification of positive plaques.

Some of the positive plaques were cored out and stored in 1 mL SM buffer [5.8 g/L NaCl, 2 g/L $MgSO_4$, 20 mM Tris-HCl, pH 7.5, 5 mL/L of 2% (w/v) gelatin] with 50 μL chloroform. Phage were plated for secondary screening using 50 μL of a 1:1000 dilution of the primary phage stock. Positive plaques from the secondary screening were cored out and stored in 500 μL of SM buffer. Phage from these stocks were then plated for tertiary screenings using amounts ranging from 5 μL of undiluted secondary stock to 20 μL of 1:100 dilution in SM buffer. All subsequent hybridizations were performed as described, supra. Isolates were rescued into phagemid form per the LAMBDA-ZAP II Library Instruction Manual (Stratagene). Rescued phagemid were plated by combining 200 μL SOLR cells (Stratagene) grown to $OD_{600nm}$=0.5 to 1.0 with 50–100 μL phagemid and incubating for 15 min at 37° C. Cells containing phagemid were streaked on LB agar containing Ampicillin (75 μg/mL) and grown overnight at 37° C. DNA was extracted from 4 mL liquid cultures grown overnight at 37° C. in TB [1.2% tryptone, 2.4% yeast extract, 0.4% glycerol, 0.17 M $KH_2PO_4$, and 0.72 M $K_2HPO_4$] using the alkaline lysis/polyethylene glycol protocol described in the PRISM READY REACTION DYEDEOXY Terminator Cycle Sequencing Kit Protocol#401388 Rev. B (Perkin-Elmer, Applied Biosystems Division). A sequence of the full length maize Δ-9 desaturase cDNA and corresponding amino acid sequence is entered herein as SEQ ID NO:5 and SEQ ID NO:6, respectively.

EXAMPLE 2

Expression of the Genes Encoding Maize Stearoyl-ACP Δ-9 Desaturase (Δ-9 Desaturase) Mature Protein and Precursor Protein The coding sequence of maize Δ9 desaturase was cloned in expression vector pET9d DN using standard molecular cloning techniques. pET9d DN is a modified version of expression vector pET9d (Novagen Inc., Madison, Wisc.) allowing subcloning of fragments in a unique NheI site downstream from the Shine & Dalgarno sequence and translation initiation ATG codon. To facilitate subcloning the cDNA clone (SEQ ID NO:5) was amplified with primers having the sequence entered herein as SEQ ID NO:7 and SEQ ID NO:8. Following amplification, the PCR product was digested with an excess of NheI, purified through agarose gel and directly ligated into vector pET9d DN which had been cut with NheI and dephosphorylated with calf intestinal phosphatase. The ligation was transformed into *E. coli* DH5α cells and recombinant plasmids containing inserts were selected by miniprep screening and digestion with NheI. One clone with the appropriate sized insert in the correct orientation relative to the T7 promoter was identified by separate digestion with NheI, NcoI or XhoI. By subcloning fragment in the NheI site of pET9d DN, the putative precursor polypeptide was joined to the ATG codon downstream from the T7 promoter and bacterial Shine & Dalgarno sequence provided by pET9d DN. This NheI site changed the nucleotide sequence of the putative N-terminus of the precursor protein from SEQ ID NO: 57 to SEQ ID NO.: 58, which changed the encoded acid sequence SEQ ID NO.: 59 to SEQ ID NO.: 60. The insert of this clone was sequenced entirely and the clone was assigned number pDAB432D.

The precursor maize Δ9 desaturase was expressed in *E. coli* BL21(DE3) (Novagen Inc., Madison, Wis.). For small scale expression, 1 μg of plasmid pDAB432D was transformed into 200 μL $CaCl_2$ competent cells and plated on two LB plates containing kanamycin at 25 μg/mL. Following overnight incubation at 37° C. colonies were scraped off the plate and resuspended in 10 mL of LB Broth containing kanamycin (50 μg/mL) and isopropyl-β-D-thiogalactoside (IPTG) at 1.0 mM. Cells were allowed to express proteins for 3 hr during vigorous shaking at 37° C. Cells were harvested by centrifugation at 3000 rpm for 10 min at 4° C. The cell pellet was frozen and thawed twice in dry ice-ethanol to improve cell lysis. Next, the cell pellet was resuspended in 1.0 mL of lysis buffer (10 mM Tris HCl pH 8.0, 1.0 mM EDTA, 150 mM NaCl, 0.1% Triton×100, 100 μg/mL DNaseI, 100 μg/mL RNaseH, 1.0 mg/mL lysozyme) and incubated at 37° C. until it was no longer viscous. Soluble proteins were separated from aggregated denatured proteins by centrifugation at 4° C. for 10 min. The insoluble pellet was resuspended in about 300 μL of the above lysis buffer. Both fractions had an approximate final volume of 0.5 mL.

Protein expression experiments were analyzed by electrophoresis of small aliquots (1.0 to 2.0 μL) of the soluble and pellet fractions on 10–15% gradient SDS polyacrylamide Phast Gels (Pharmacia LKB Biotechnology, Piscataway, N.J.). Protein bands were visualized by staining with Coomassie Brilliant Blue in the Phast Gel apparatus, and destained overnight by shaking in a small volume of 10% glycerol, 10% acetic acid. Molecular size of bands was determined by comparison to Bio-Rad Low Molecular Weight markers (Bio-Rad Laboratories, Hercules, Calif.). Western blot analysis was performed using antibodies produced as described herein specific to the mature portion of maize Δ9-desaturase. Expression of plasmid pDAB432D in *E.coli* resulted in the production of a 42 kDa protein in the cell pellet, indicating that the precursor protein produced in *E. coli* was insoluble.

In production of mature Δ-9 desaturase protein, the portion of the cDNA clone encoding the mature desaturase protein was subcloned into pETd DΔN. The amino terminus of the mature maize Δ-9 desaturase protein determined as described herein. In order to express the mature protein, DNA corresponding to SEQ ID NO:11 was cloned into the expression vector pET9dΔN which is a modified version of pET9d (Novagen, Inc.). The vector pET9dΔN allowed subcloning of fragments in a unique NheI site downstream from the Shine and Dalgarno sequence and translation initiation ATG codon.

To facilitate subcloning, DNA corresponding to SEQ ID NO:5 was amplified with primers entered herein as SEQ ID NO:9 and SEQ ID NO:10. The DNA product had the sequence entered herein as SEQ ID NO:11 and encoded a protein having the amino acid sequence entered herein as SEQ ID NO:12. Following amplification, the PCR product was digested with an excess of NheI, gel purified through agarose gel and directly ligated into vector pET9dΔN which had been cut with NheI and dephosphorylated with calf intestinal phosphatase. The ligation was transformed into *E. coli* DH5α cells, and recombinant plasmid containing inserts were selected by miniprep screening and digestion with NheI. Clones with the insert in the correct orientation relative to the T7 promoter were identified by separate digestions with NcoI or XhoI. The plasmid having the DNA construct in the correct orientation was named pDAB428. Expression of protein from said plasmid was performed in a manner similar to that described for plasmid pDAB432D.

EXAMPLE 3

Purification and Characterization of Native and *E. coli* Expressed Maize Stearoyl-ACP Δ-9 Desaturase (Δ-9 Desaturase)

An *E. coli* produced supernatant containing mature maize Δ-9 desaturase, as described above, was adjusted to 25 mM sodium phosphate buffer (pH 6.0) and chilled on ice for 1 h. Afterwards, the resulting flocculant precipitant was removed by centrifugation. The ice incubation step was repeated twice after which the solution remained clear. The clarified solution was loaded onto a Mono S HR10/10 column (Pharmacia) that had been equilibrated in 25 mM sodium phosphate buffer (pH 6.0). Proteins bound to the column matrix were eluted using a 0–500 mM NaCl gradient over 1 h (2 mL/min; 2 mL fractions). Fractions containing Δ-9 desaturase activity as described herein were pooled and separated based on size using a Superose 12B HR16/50 (Pharmacia) column) at a flow rate of 1.2 mL/min that had been equilibrated in 50 mM Tris-HCl (pH 7.5). Fractions were collected (1.2 mL/fraction) and samples were assayed for the presence of Δ-9 desaturase protein via SDS-PAGE. Molecular size calculations were based on column calibration using the following standards: ribonuclease A (13.7 kDa); ovalbumin (43.0 kDa); bovine serum albumin (67.0 kDa); aldolase (158.0 kDa); catalase (232.0 kDa); ferritin (440.0 kDa) and blue dextran (2,000 kDa).

The putative protein of interest was subjected to SDS-PAGE, blotted onto ProBlott membrane (Amersham), visualized with 0.02% amido black, excised, and sent to Harvard Microchem, (Boston, Mass.) for amino-terminal sequence analysis thus yielding the sequence entered herein as SEQ ID NO:13. Spectrophotometric analysis of the diiron-oxo component associated with the expressed protein (Fox et al., 1993, Proc. Natl. Acad. Sci. USA 90:2486–2490), as well as identification using a stain specific for nonheme iron (Leong et al., 1992, Anal. Biochem. 207:317–320) were also used to confirmed that the protein was mature Δ-9 desaturase.

The *E. coli* produced mature Δ-9 desaturase, as determined by amino terminal sequencing, was gel purified via SDS-PAGE and sent in the gel matrix to Berkeley Antibody Co. (Richmond, Calif.) for production of polyclonal antiserum in rabbits. Inoculations of antigen were initiated with 200 μg protein followed by three boosting injections of 100 μg each at three week intervals. Evaluations of antibody titers against mature Δ-9 desaturase were performed via western analysis using the ECL detection system (Amersham, Inc.; Arlington Heights, Ill.).

Polyclonal antiserum produced above were used for western analysis as follows: purified or partially purified proteins were subjected to SDS-PAGE analysis on a 10–20% polyacrylamide gel (Integrated Separation Systems, Natick, Mass.) using the method described by Laemmli (1970, Nature 277:680). Proteins were then transferred to nitrocellulose paper using a Pharmacia Semi-Dry Blotter and the nonspecific binding sites were blocked with BLOTTO (5% dry milk in phosphate buffered saline [PBSI]/0.05% Tween-20). The membrane was incubated in the polyclonal media (polyclonal antibody diluted 1:1000 in BLOTTO) for 1 h at room temperature while agitating on an orbital shaker. Afterwards, membranes were washed three times for 0.5 h each with excess BLOTTO followed by incubation for 0.5 h with a 1:2000 dilution of horseradish peroxidase linked goat-anti-rabbit polyclonal serum (BioRad, Hercules, Calif.). Following incubation, blots were washed three times for 10 min each with an excess of BLOTTO and then developed using the ECL Detection System (Amersham Inc.) as per the manufacturer's instructions.

Δ-9 desaturase was purified from corn kernels following homogenization using a Warring blender in 25 mM sodium phosphate buffer (pH 7.0) containing 25 mM sodium bisulfite and 2.5% polyvinylpolypyrrolidone. The crude homogenate was filtered through cheesecloth, centrifuged (10,000×g) for 0.25 h and the resulting supernatant was filtered once more through cheesecloth. In some cases, the supernatant was fractionated via saturated ammonium sulfate precipitation at 20%. (v/v). Upon centrifugation, the resulting supernatant was then precipitated with 80% (v/v) ammonium sulfate. Resulting pellets were dialyzed extensively against 25 mM sodium phosphate buffer (pH 6.0). After dialysis, the material was clarified via centrifugation and applied to a Mono S HR10/10 column (Pharmacia, Inc. Piscataway, N.J.) equilibrated in 25 mM sodium phosphate buffer (pH 6.0). After extensive column washing, proteins bound to the column matrix were eluted using a 0–500 mM NaCl gradient over 1 h (2 mL/min; 2 mL fractions). Upon dialysis, this material was further fractionated by acyl carrier protein (ACP)-sepharose and phenyl Superose chromatography.

ACP-sepharose matrix was prepared as follows: ACP was purchased from Sigma Chemical Co. (St. Louis, Mo.) and purified by repeated precipitation at PH 4.1 followed by resolubilization (Rock and Cronan, 1981, Methods in Enzymology 71:341–351). Attachment of ACP to cyanogen bromide-activated Sepharose 4-B beads was performed essentially as described by Pharmacia, Inc., in the package insert. After linkage and blocking of the remaining sites with glycine, the ACP-sepharose material was packed into a HR 5/5 column (Pharmacia, Inc.) and equilibrated in 25 mM sodium phosphate buffer (pH 7.0). Mono-S fractions identified as having Δ-9 desaturase activity were then loaded onto the ACP-Sepharose column as described previously (McKeon and Stumpf, 1982, J. Biol. Chem. 254:7116–7122; Thompson et al., 1991, J. Biol. Chem. 257:12141–12147). After extensive column washing, ACP-binding proteins were eluted using 1M NaCl.

Fractions containing Δ-9 desaturase activity obtained from the ACP-sepharose column were adjusted to 0.4 M ammonium sulfate (25 mM sodium phosphate, pH 7.0) and loaded onto a Pharmacia Phenyl Superose column (HR 10/10). Proteins were eluted by running a gradient (0.4–0.0 M ammonium sulfate) at 2 mL/min for 1 hr. Δ-9 desaturase activity typically eluted between 60- and 30 mM ammonium sulfate as determined by enzymatic and western analysis. Proteins were dialyzed extensively and concentrated using a Centricon-10 concentrator (Amicon, Inc., Beverly, Mass.). Samples were then blotted to PVDF membrane as described herein and sent to Harvard Microchem for amino terminal analysis. The amino terminal sequence is entered herein as SEQ ID NO:14.

Production of substrate for Δ-9 desaturase activity assays was performed as follows. Cells harboring a plasmid encoding acyl-ACP synthetase (Jackowski et al., 1994, J. Biol. Chem. 269:2921–2928) were grown, heat shock induced, and the acyl-ACP synthetase protein produced therein was partially purified essentially as described by Rock and Cronan, (1979, J. Biol. Chem. 254:7116–7122). [9,10 (n)-$^{3}$H] stearic acid (specific activity=49 Ci/mmol) was custom synthesized by Amersham Life Sciences, Inc. Radioactive and non radioactive ACP-stearate was synthesized essentially as described by Rock et al., (1981, Methods in Enzymology 71:341–351). Substrate production reactions were allowed to proceed for 16 h at 37° C. before termination and purification. Non-radioactive substrate was made by using nonlabeled stearic acid. All reagents, unless otherwise specified, were obtained from Sigma Chemical Co.

Analysis of Δ-9 desaturase enzymatic activity was performed essentially as described by Thompson et al., (1991, Proc. Natl. Acad. Sci USA 88:2578–2582). Reactions were typically performed in triplicate and at three different enzyme concentrations to ensure linearity. Non-radioactive ACP-stearate was spiked with $^{3}$H-substrate and used at 60 μM final concentration (total volume=500 μL; total radioactivity=$5.1\times10^{4}$ dpm/sample). Reactions were allowed to proceed for 10 min at 25° C. and were terminated by adding 0.5 mL of 12% (w/v) trichloroacetic acid (TCA). After incubation for 5 min, the resulting precipitate was centrifuged and an aliquot of the remaining supernatant was removed (0.5 mL) and pH adjusted by adding 500 μL of 1M Tris (pH 8.0). The Δ-9 desaturase enzymatic activity was quantitated by measuring the amount of $^{3}$H released by liquid scintillation counting. A unit of activity was defined as the production of 1 μmole of oleate/min as determined by the release of $^{3}H_2O$ (McKeon and Stumpf, 1982, J. Biol. Chem. 257, 12141–12147). Testing of the maize purified and *E. coli* expressed Δ-9 desaturase protein proved that both protein preparations had the appropriate desaturase enzymatic activity.

EXAMPLE 4

Production of Synthetic Δ-9 Desaturase Transit Peptide (Δ-9TP) and Production of Polyclonal Antibodies Specific Thereto As described herein, the maize Δ-9 desaturase gene was cloned and the amino acid sequence of the putative transit peptide (Δ-9TP) was determined and entered herein as SEQ ID NO:15. This sequence information was sent to BioSynthesis, Inc., (Lewisville, Tex.) for peptide synthesis. Once received, the peptide was dissolved in sterile water and aliquots thereof were analyzed by gel electrophoresis on a 4–27% gradient gel (Integrated Separation Science, Inc., Natick, Mass.). By comparing to the molecular weight markers, the synthetic Δ-9TP was determined to be about 4.0 kDa. The synthetic Δ-9TP was then conjugated to Keyhole Limpet hemacyanin (KLH) and injected into rabbits for polyclonal antibody production by BioSynthesis, Inc. Serum was taken at 10 weeks and 13 weeks after the initial injection. Polyclonal antibodies derived from this production were so named Pab-TP.

Immunospecificity of Pab-TP to the Δ-9TP peptide was determined by Western blot analysis using *E. coli* produced precursor (pDAB432D) and mature Δ-9 desaturase protein (pDAB428), as well as the synthetically made Δ-9TP polypeptide. Proteins were loaded onto a SDS-PAGE gel as described herein and were then blotted to PVDF membrane for western analysis as previously described. In testing Pab-TP antibodies, it was observed that said antibodies were immunologically reactive to both the precursor Δ-9 desaturase and the Δ-9TP polypeptide but did not recognize the mature protein. These data indicated that Pab-TP antibodies were specific for the transit peptide portion only of maize Δ-9 desaturase.

EXAMPLE 5

Production and Screening of Hybridoma Cell Lines

Approximately 100 to 200 μg of KLH conjugated Δ-9TP or Δ-9 desaturase mature protein was mixed with 1.0 mL of 1:1 mixture of Freund's Complete adjuvant and Freund's Incomplete adjuvant (Sigma Chemical Co.) for the initial immunizations. Samples were mixed only with Freund's incomplete adjuvant for subsequent immunization. Approximately 150 mL of the antigen was injected intraperitoneally into individual Balb/c mice at two week intervals. After 5 injections, immunogenic response was determined by Western analysis of sera from said mice. Injections were continued if the immunogenic response was weak, otherwise, mice were used in the production of hybridoma cell lines.

The cell fusion protocol was based on the procedure described by Galfre and Milstein (1981, Methods in Enzymology 73:3–46). After the spleen was aseptically removed from an individual mouse, spleen cells were separated and washed twice with RPMI 1640 medium (Cellgro™ , Fisher Scientific, Pittsburgh, Pa.). A viable cell count was determined after addition of an equal volume of Red Blood Cell Lysis Buffer (Sigma, St. Louis, Mo.), and 2 volumes of Trypan blue (Sigma, St. Louis, Mo.). Myeloma cells (X63Ag8) originally purchased from American Tissue Culture Collection (ATCC) were used as the fusion partner.

Myeloma cells were grown at a density of $7\times10^5$ cells/mL. Two days prior to cell fusion, cultures were diluted to $2\times10^5$ cells/mL and washed twice with RPMI 1640 medium. Approximately $10^8$ spleen cells and $3.5\times10^7$ myeloma cells (a ratio of 3:1 spleen cells:myeloma cells) were used for each fusion. These cells were washed together once and the wash medium was discarded. One mL of pre-melted PEG 4000 (5.0 mg in 2.5 mL RPMI 1640 medium, 40° C.) was added to the cell pellet. After 1 min, 20 mL of RPMI 1640 medium was gently added and the mixture was incubated at 37° C. for 20 min. The medium was removed by centrifugation. Cell pellets were then resuspended in 200 mL of selection medium containing: complete medium [500 mL RPMI 1640, 50 mL fetal bovine serum (Sigma Chemical Co.), 6 mL 200 mM L-glutamine (Cellgro™), 6 mL 100 mM sodium pyruvate (Cellgro™), 5000 units penicillin-streptomycin (Cellgro™)], 10% Origen Hybridoma Cloning Factor (HCF; Origen, Fisher Scientific), and 1×HAT solution (hypoxanthine, aminopterin, and thymidine (Cellgro™). Cells were incubated for 1 h at 37° C. and 200 $\mu$L thereof were distributed into each well of 96-well plates. After 10 to 14 days, media from each well were screened for antibody-producing hybridomas.

ELISA techniques were used to screen for Δ-9TP specific monoclonal antibody (Mab) producing hybridoma cell lines. The assay involved first applying the antigen (10–50 ng of synthetic Δ-9TP or precursor protein produced from pDAB432D) in 0.1 M sodium carbonate into wells of microtiter plates (Dynatech Laboratories, Chantilly, Va.) and incubating overnight at 4° C. Afterwards, the excess antigen solution was discarded and the wells were blocked with 1% BSA (bovine serum albumin) in PBS (phosphate buffer saline, Sigma) at 37° C. for at least 1 h. The blocking solution was discarded, and 100 $\mu$L of hybridoma cell medium was added to each well. Plates were incubated at 37° C. for at least 1 h, after which they were washed 3 times with wash solution (0.025% Tween 20 in PBS). A 100 $\mu$L volume of a 1:1000 dilution of alkaline phosphatase conjugated anti-IgG+IgM antibodies (Kirkegaard & Perry, Gaithersburg, Md.) in 1% BSA in PBS was added to each well. The plates were incubated at 37° C. for 1 h and washed 3 times with the wash solution. Finally, the phosphatase substrate p-NPP (para-nitrophenyl phosphate; Kirkegaard & Perry, Gaithersburg, Md.) prepared according to the manufacturer's procedure was added to the wells. The color was allowed to develop for 10 to 30 min before the $A_{405nm}$ was determined using a plate reader (Molecular Devices, Sunnyvale, Calif.).

Cell lines determined positive by ELISA were increased by transferring the cells to 6-well plates containing fresh complete medium supplemented with 5% HCF. Once established, cell lines were re-screened by standard Western Blot analysis. Typically, 20 to 50 ng of precursor Δ-9 desaturase protein (pDAB432D) was applied to each well of a SDS polyacrylamide gel. After gel electrophoresis was completed, proteins were electroblotted onto Hybond-ECL nitrocellulose membrane (Amersham, Arlington Heights, Ill.) and western analysis was performed as described previously. Hybridoma cell medium obtained from test lines was used as the primary antibody. Secondary antibodies were typically goat-anti-mouse IgG conjugated to horseradish peroxidase (BioRad). Detection of immunological binding was performed using an ECL detection kit (Amersham) according to manufacturer's instruction.

Antibodies of interest were purified from the cell media using a Pure I antibody purification kit (Sigma). Two antibodies obtained from monoclonal cell lines (Mab-TP1 and Mab-Δ9M) were further characterized by isotyping. Antibody isotype was classified using a Mouse Isotyping Kit (Boehringer Mannheim, Indianapolis, Ind.). Mab-TP1 and Mab-Δ9M were determined to be IgG 2b Kappa Light Chain, and IgG1 Kappa Light Chain, respectively.

To determine binding specificity of the selected MAbs, a Western blot analysis was performed using the following as antigen: black mexican sweet corn (BMS) callus tissue, Type II corn callus tissue, maize seed extract, *E.coli* produced precursor protein (pDAB432D), and purified mature Δ-9 desaturase protein. Duplicate blots were made and each blot was incubated with MAb-TP1, or MAb-Δ9M. The result showed that MAb-TP1 could only recognize Δ-9 desaturase precursor protein and did not recognize mature Δ9-desaturase or only other proteins in callus tissues or seeds. These data indicated that the Mabs generated against Δ-9TP were specific thereto.

EXAMPLE 6

Cloning of Genes from Monoclonal Cell Lines

Hybridoma cell lines of interest were grown in two 150 mL flasks containing 60 mL of hybridoma medium. Seven days after inoculation, about $1\times10^8$ cells were harvested into 50 mL centrifuge tubes and pelleted by centrifugation at 800 rpm using a table-top centrifuge. The medium was discarded and the cells were washed twice with sterile PBS. Tubes containing washed cells were placed on dry ice for 15 min prior to mRNA isolation.

PolyA+ mRNA was isolated using a Fast Track mRNA Isolation Kit (Invitrogen, Carlsbad, Calif.). Hybridoma cells were resuspended in 15 mL of lysis buffer provided therein. Cells were sheared by passing through a sterile 60 cc syringe fitted with an 18–21 gauge needle. This process was repeated 4 times. Lysates were incubated at 45° C. for 15 min while shaking after which 950 $\mu$L of 5M NaCl was added. Upon mixing thoroughly, the solution was passed through the syringe an additional 4 times in order to cause DNA shearing. Seventy-five mg of powdered Oligo (dt) Cellulose was then added and the tube was rocked gently at room temperature for 1 h. Afterwards, lysates were centrifuge at 2000–4000×g in a table top centrifuge for 5 min, supernatants were discarded, and pellets were washed twice with binding buffer and low salt buffer as provided. Pellets were then resuspended in 800 $\mu$L of low salt buffer. Cellulose suspensions were transferred into a spin column and washed 3 times by centrifugation and by addition of low salt buffer. After the last centrifugation, pellets were resuspended in 200 $\mu$L of Elution Buffer, the solution was collected by centrifugation and the process was repeated for a total volume of 400 $\mu$L. To precipitate the RNA, 60 $\mu$L of 2M sodium acetate and 1000 $\mu$L of absolute ethanol were added to the collected solution followed by freezing on dry ice.

Following, tubes were centrifuged at 14,000×g for 15 min and the mRNA pellet was resuspended in 20 to 40 μL of sterile filtered water.

The mRNA obtained above was used to produce cDNA by reverse transcriptase reactions using cDNA Cycling® Kit (Invitrogen, Carlsbad, Calif.) according manufacturer's instructions. Typically, the total reaction volume was 20 μL with 8 μL of mRNA added thereto. Reactions were started by adding mRNA and water followed by heating for 10 min at 65° C. and then followed by cooling for 2 min at room temperature. Afterwards, RNase inhibitor, buffer, nucleotide triphosphates, sodium pyrophosphate and reverse transcriptase were added. Ingredients were mixed and tubes were spun briefly before incubating at 42° C. for 1 h. Tubes were then incubated at 95° C. for 2 min before being placed on ice. cDNA synthesis was repeated again by adding additional reverse transcriptase followed by incubation for 1 h, followed by phenol extraction with 1 μL 0.5 M EDTA, pH 8.0 and 20 μL of Phenol/Chloroform/Isoamyl Alcohol (25:24:1). The tube was vortexed, centrifuged and the aqueous solution was recovered. To the aqueous solution was added 22 μL of ammonium acetate and 88 μL of absolute ethanol followed by freezing on dry ice and collection of pellets by centrifugation. Pellets were dissolved in sterile water and stored until further use.

Degenerate primers were designed and synthesized as disclosed herein. The 5' primers were designed to anneal to the signal peptide of the heavy (SEQ ID NO:16) or light chain genes (SEQ ID NO:17) based on published sequences (Kabat et al., 1987, Sequences of Proteins of Immunological Interest; $4^{th}$ Ed. U.S. Department of Health and Human Services, Public Health Service, NIH). The 3' primers were designed to anneal to the constant region of the heavy (SEQ ID NO:18) and light chain genes (SEQ ID NO:19).

Genes of interest were obtained by PCR. The reaction (100 μL total volume) was prepared using a PCR Core Kit (Boehringer Mannheim, Corp., Indianapolis, Ind.) and typically contained 0.5 μg cDNA template and 100 pm of each primer. The heavy and light chain cDNAs were PCR amplified in separate experiments. PCR conditions were as follows: [95° C. (1 min); 55° C. (0.5 min); 72° C. (0.5 min)] for 30 cycles followed by 1 cycle of 95° C. (1 min); 55° C. (0.5 min); 72° C. for 2 min. PCR products were observed using agarose gel electrophoresis and ethidium bromide staining. Amplification of the heavy and light chains resulted in DNA fragments of about 730 bp each entered herein as SEQ ID NO:24 and SEQ ID NO:21, respectively. Products were then digested with the NheI, cloned into pBlueBac1 (Invitrogen, Carlsbad, Calif.) and transformed into DH5α strain of *E. coli* using standard procedures. Clones were recovered and digested with NheI to verify the DNA insert. Plasmid DNA was produced, isolated, and sequenced as previously described using several external and internal primers. The DNA encoding the light chain (SEQ ID NO:50) was modified as follows: a 5' primer, entered herein as SEQ ID NO:20, was designed to replace the native mouse signal peptide with a Baculovirus gp67 and (p67) leader (Murphy et al., 1993, Protein Expression and Purification, 4:349–357). SEQ ID NO:50 was used as the 3' primer. After performing PCR as described herein, the DNA was digested with Xba I and Not I enzymes and inserted into a Baculovirus transfer plasmid, pAcMP3 (PharMingen, San Diego, Calif.). The cloned plasmid (AcMP3/TpLCp67) was transformed into the DH5α strain of *E. coli* (Gibco, Gaithersburg, Md). Several clones were recovered on the selection plates. Plasmid DNA was isolated from a selected clone and re-sequenced. Said sequence is entered herein as SEQ ID NO:49. The DNA encoding the hypervariable region of said clone is entered herein as SEQ ID NO:22. Comparison of sequence information indicated that the cloned Kappa chain was the authentic light chain of the Mab-Δ-9TP1 gene and not the endogenous non-functional light chain of myeloma cells (X63Ag8).

The DNA encoding the heavy chain (SEQ ID NO:24), obtained by using PCR primers SEQ ID NO: 16 and SEQ ID NO:18, was purified, digested with Xba I and Not I and ligated into pAcMP3. Sequencing data indicated that said clone was an authentic IgG2B heavy chain gene. The gene was re-amplified by PCR using primers with a sequence according to SEQ ID NO:23 and SEQ ID NO:18 to add a p67 Baculovirus leader, cloned into the AcMP3 Baculovirus transfer plasmid (AcMP3/TpHCp67) and transformed into *E. coli* as described herein. Colonies were screened and an appropriate clone was sequenced. The sequence (SEQ ID NO:51) matched that previously determined for the Mab-TP1 heavy chain. Comparison to known heavy chains revealed that the two CH1 sequences were identical indicating that the cloned heavy chain gene is an authentic IgG2B sequence. The sequence of the hypervariable region is entered herein as SEQ ID NO:25.

EXAMPLE 7

Generation of Recombinant Baculovirus Expressing Mab-TP1

SF9 (Invitrogen) cells were cultured at 27° C. in spinner flasks with Sf900II (Gibco, Gaithersburg, Md.) serum free complete medium supplemented with penicillin/streptomycin/fungizone at ½ rate. Cells were split to $3\times10^5$ cells/mL every four days. SF9 cells were seeded at $8\times10^5$ cells/well in a six well plate and allowed to attach for 1 h at 27° C. The medium was discarded and cells were washed twice with fresh medium without antibiotics. After the last wash, 1.5 mL of fresh medium without antibiotics was added. In a polystyrene tube, 0.1 μg of linearized parental Baculovirus DNA (Baculogold, PharMingen, San Diego, Calif.) was mixed with 0.5 μg of the transfer vector (AcMP3/TpLCp67 or AcMP3/TpHCp67 plasmid), followed by transfection mix as described in the standard cationic lipisome mediated transfection protocol as provided by CLONTECH (Palo Alto, Calif.). Transfection medium was harvested after four days and samples of medium and cell pellet were analyzed for protein expression by western analysis as described herein. A 1:1000 dilution of goat anti-mouse FAb-specific IgG conjugated to horseradish peroxidase (Sigma Chemical Co.) was used with a ECL detection kit (Amersham). The results indicated that light chain and heavy chain proteins could be produced and recognized by appropriate antibodies, thus authenticity was confirmed.

To determine if functional antibodies could be produced, recombinant virus, AcMP3/TpLCp67 and AcMP3/TpHCp67 were co-infected in SF9 cells. The cell medium was harvested and used as the primary antibody in Western analysis using precursor Δ-9 desaturase (pDAB432D) as antigen. The expected sized band (42 kDa) was observed indicating that the recombinant antibody produced was indeed functional.

EXAMPLE 8

Construction of the Single Chain Antibody-TP1 (SCAb-TP1) Gene

Generation of the SCAb-Tp1 gene was accomplished via a two step PCR reaction using the PCR core kit (Boehringer Mannheim). Standard reactions contained 200 $\mu$M dNTPs, 100 pM primer, SEQ ID NO:24 or SEQ ID NO:49 as template (0.5 $\mu$g), PCR buffer and 4 units of Taq polymerase as described previously. A sample of each reaction was analyzed in a 1% agarose gel. Approximately equal molar amounts of light and heavy chain product were then added to a second reaction using the same conditions as above except that different primers were used. The resulting PCR products were then isolated and purified from 1% agarose gels using the Qaiex II kit (Qiagen).

Amplification of the heavy chain variable region of SEQ ID NO:24 (which is SEQ ID NO:25) with primers according to SEQ ID NO:23 and SEQ ID NO:26 resulted in a PCR product of ~450 bp entered herein as SEQ ID NO:29. Amplification of the light chain variable region of SEQ ID NO: 21 (which is SEQ ID NO:22) with primers according to SEQ ID NO:27 and SEQ ID NO:28 resulted in PCR product of ~440 bp entered herein as SEQ ID NO:30. A sewing reaction using equal molar amounts DNA according to SEQ ID NO:29 and SEQ ID NO:30 using primers according to SEQ ID NO:23 and SEQ ID NO:28 yielded the SCAb-Tp1 gene product of ~830 bp and having a DNA and amino acid sequence entered herein as SEQ ID NO:31 and SEQ ID NO:32, respectively. The DNA was then digested with Xba I and Not I and ligated into the AcMP3 Baculovirus transfer vector (PharMingen). A positive clone was identified and sequenced (SEQ ID NO:31), a c-myc tag (SEQ ID NO:33) was added to the 3' end of the gene and the p67 leader sequence (SEQ ID NO:34) was added at the 5' terminus.

The SCAb-TP1 gene (SEQ ID NO:31) was reconstructed by PCR using the reaction conditions described above. Amplification of DNA according to SEQ ID NO:22 with primers according to SEQ ID NO:35 and SEQ ID NO:36 resulted in a product of ~450 bp, having the sequence entered herein as SEQ ID NO:40. Amplification of DNA according to SEQ ID NO:25 with primers according to SEQ ID NO:37 and SEQ ID NO:38 (TABLE V) resulted in a product of ~440 bp having a DNA sequence according to SEQ ID NO:41. Approximately equal molar amounts of each product (SEQ ID NO:40 and SEQ ID NO:41) were added to another reaction with primers according to SEQ ID NO:35 and SEQ ID NO:38 yielding a product of ~846 bp (SEQ ID NO:42). An additional PCR reaction was performed with DNA according to SEQ ID NO:42 using the primer pair having a DNA sequence according to SEQ ID NO:35 and SEQ ID NO:39 to add a stop codon to the 3' end of the gene. The ~849 bp product (SEQ ID NO:43) was isolated from a 1% agarose gel, digested with Xba I/Not I and ligated into the AcMP3 transfer vector (AcMP3/TPSCegt). An appropriate clone was identified and sequenced.

AcMP3/TPSCegt and BacPAK6 Bsu36 I linear parental DNA (Clontech) were co-transfected into SF9 insect cells to create recombinant virus. Cationic lipisome mediated transfection was performed as described in the instructions included with the BacPAK6 DNA. The transfection media was harvested after 48 h and 0.5 mL was used to infect a 175 $cm^2$ flask containing $2\times10^7$ SF9 cells to amplify the recombinant virus. Western analysis performed as described herein identified a ~28 kD protein in infected cells using an anti-HIS antibody (Qiagen, Inc., Chatsworth, Calif.). SCAb-Tp1 produced in the Baculovirus system was compared to the native MAb-Δ-9TP1 in Western blots using *E. coli* expressed Δ-9 desaturase precursor (pDAB432D) as antigen. These blots indicated no difference in the binding pattern between the native MAb TP1 and the recombinant SCAb-TP1.

The SCAb-TP1 gene was rebuilt to facilitate cloning into the pDAB439 plant transformation vector. PCR reactions were performed using the DNA according to SEQ ID NO:43 with the primer pairs having DNA sequences according to SEQ ID NO:44/SEQ ID NO:46 and primer pairs having DNA sequences according to SEQ ID NO:45/SEQ ID NO:46. The resulting products (SEQ ID NO:47 and SEQ ID NO:48) were isolated from a 1% agarose gel, digested with Sfi I and ligated into pDAB439. An appropriate clone was identified for each construct, grown up and sequenced thus yielding the plasmids pDAB439/TPE containing SEQ ID NO:47 and pDAB439/TPnoE containing SEQ ID NO:48.

Plasmid pDAB439 was a 7040 base pairs double stranded plant transformation vector composed of the following sequences in clockwise order. The plasmid backbone was derived from pUC19 (Yanish-Perron et al., (1985) Gene 33:103–119). Nucleotides 1 to 2252 of pDAB439 corresponded to the reverse complement of nucleotides 435 to 2686 of pUC19. Nucleotides 2253 to 2271 of pDAB439 had the sequence TGCATGTGTT CTCCTTTTT (SEQ ID NO:52). Nucleotides 2272 to 4264 of pDAB439 were the maize ubiquitin promoter and first intron, and were PCR amplified from genomic DNA of maize genotype B73 (Christensen et al., (1992) Plant Mol. Biol. 18:675–689). Nucleotides 4265 to 4308 of pDAB439 had the sequence GGTACGGCCA TATTGGCCGA GCTCGGCCTC TCTGGCCGAT CCCC (SEA ID NO:53). Nucleotides 4309 to 4576 of pDAB439 corresponded to nucleotides 4420 to 4687 of plasmid pBI101 (Clontech, Palo Alto, Calif.) followed by the linker GG as nucleotides 4577 and 4578 of pDAB439. Nucleotides 4579 to 4743 of pDAB439 were the reverse complement of nucleotides 238–402 of pUC19. Nucleotides 4744 to 4807 of pDAB439 corresponded to: GCGGCCGCTT TAACGCCCGG GCATTTAAAT GGCGCGCCGC GATCGCTTGC AGATCTGCAT GGG (SEQ ID NO:54). Nucleotides 4808–5416 of pDAB439 comprised the double enhanced 35S promoter, with nucleotides 5070 to 5416 corresponding to nucleotides 7093 to 7439 of the Cauliflower Mosaic Virus genome (Franck et al., (1980) Cell 21:285–294). Nucleotides 4808 to 5061 of pDAB439 were a duplication of nucleotides 5068 to 5321. Nucleotides 5062 to 5067 of pDAB439 comprised the linker CATCGA. Nucleotides 5417–5436 of pDAB439 comprised the linker GGGGACTCTA GAGGATCCAG (SEQ ID NO:55). Nucleotides 5437 to 5547 of pDAB439 corresponded to nucleotides 167 to 277 of the Maize Streak Virus genome (Mullineaux et al., (1984) EMBO J. 3:3063–3068). Nucleotides 5548 to 5764 of pDAB439 corresponded to the modified first intron of the maize alcohol dehydrogenase gene (Adh1-S) (Dennis et al., (1984) Nucleic Acids Res. 12:3983–4000). The modification resulted in removal of 343 nucleotides (bases 1313 to 1656) with bases 1222 to 1312 (intron 5' end) and nucleotides 1657 to 1775 (intron 3' end) of the maize Adh1-S gene remaining. Nucleotides 5765 to 5802 of pDAB439 corresponded to Maize Streak Virus (MSV) nucleotides 278 to 312, followed by the linker sequence CAG. Both sections of the Maize Streak Virus, hereinafter MSV, sequence comprised the untranslated leader of the MSV coat protein V2 gene, and were interrupted in plasmid pDAB439 by the modified Adh1 intron. Nucleotides 5803 to 6359 of plasmid pDAB439 corresponded to nucleotides 29 to 585 of the phosphinotricin acetyl transferase (BAR) gene of Streptomyces hygroscopicus (White et al., (1989) Nucleic Acids Res. 18:1062). To facilitate cloning, nucleotides 34 and 575 of the published sequence were changed from A and G to G and A, respectively. This sequence served as the selectable marker in plant cells. Nucleotides 6360 to 6364 comprised the linker GATCT. Nucleotides 6365 to 6635 of pDAB439 corresponded to nucleotides 4420 to 4683 of plasmid pBI101 (Clontech, Palo Alto, Calif.) followed by the linker sequence AGATCGC. Nucleotides 6636 to 6639 of pDAB439 comprised the linker TCGG. The remaining sequence of pDAB439 (nucleotides 6640 to 7040) corresponded to nucleotides 284 to 684 of pUC19.

EXAMPLE 9

Generation of Transgenic Maize Plants Containing and Expressing the Genes of Interest Type II callus cultures were initiated from immature zygotic embryos of the genotype "Hi-II." (Armstrong et al, (1991) Maize Cooperation Newsletter, pp.92–93). Embryos were isolated from greenhouse-grown ears from crosses between Hi-II parent A and Hi-II parent B or F2 embryos derived from a self- or sib-pollination of a Hi-II plant. Immature embryos (1.5 to 3.5 mm) were cultured on initiation medium consisting of N6 salts and vitamins (Chu et al, (1978) The N6 medium and its application to anther culture of cereal crops. Proc. Symp. Plant Tissue Culture, Peking Press, 43–56) 1.0 mg/L 2,4-D, 25 mM L-proline, 100 mg/L casein hydrolysate, 10 mg/L $AgNO_3$, 2.5 g/L GELRITE, and 20 g/L sucrose, with a pH of 5.8. Selection for Type II callus took place for ca. 2–12 weeks. After four to six weeks callus was subcultured onto maintenance medium (initiation medium in which $AgNO_3$ was omitted and L-proline was reduced to 6 mM).

The plasmids pDAB439/TPE and pDAB439/TPnoE were transformed into embryogenic callus via helium bombardment. For blasting 140 $\mu$g of plasmid DNA was precipitated onto 60 mg of alcohol-rinsed, spherical gold particles (1.5–3.0 $\mu$m diameter) by adding 74 $\mu$L of 2.5 M $CaCl_2$ $H_2O$ and 30 $\mu$L of 0.1 M spermidine (free base) to 300 $\mu$L of plasmid DNA and $H_2O$. The solution was immediately vortexed and the DNA-coated gold particles were allowed to settle. The resulting clear supernatant was removed and the gold particles were resuspended in 1 mL of absolute ethanol. This suspension was diluted with absolute ethanol to obtain 15 mg DNA-coated gold/mL. Approximately 600 mg of embryogenic callus tissue was spread over the surface of Type II callus maintenance medium as described herein lacking casein hydrolysate and L-proline, but supplemented with 0.2 M sorbitol and 0.2 M mannitol as an osmoticum. Following a 4 h pre-treatment, tissue was transferred to culture dishes containing blasting medium (osmotic media solidified with 20 g/L tissue culture agar (JRH Biosciences, Lenexa, Kans.) instead of 7 g/L GELRITE (Schweizerhall, South Plainfield, N.J.). Helium blasting accelerated suspended DNA-coated gold particles towards and into the prepared tissue targets. The device used was an earlier prototype of that described in U.S. Pat. No. 5,141,131 which is incorporated herein by reference. Tissues were covered with a stainless steel screen (104 $\mu$m openings) and placed under a partial vacuum of 25 inches of Hg in the device chamber. The DNA-coated gold particles were further diluted 1:1 with absolute ethanol prior to blasting and were accelerated at the callus targets four times using a helium pressure of 1500 psi, with each blast delivering 20 $\mu$L of the DNA/gold suspension. Immediately post-blasting, tissue was transferred to osmotic media for a 16–24 h recovery period. Afterwards, the tissue was divided into small pieces and transferred to selection medium (maintenance medium lacking casein hydrolysate and L-proline but having 30 mg/L BASTA (Agrevo)). Every four weeks for 3 months, tissue pieces were non-selectively transferred to fresh selection medium. After 7 weeks and up to 22 weeks, callus sectors found proliferating against a background of growth-inhibited tissue were removed and isolated. The resulting BASTA-resistant tissue was subcultured biweekly onto fresh selection medium. Following gas chromatography/fatty acid methyl ester, hereinafter GC/FAME, analyses, as described herein, positive transgenic lines were identified and transferred to regeneration media.

Regeneration was initiated by transferring callus tissue to cytokinin-based induction medium, which consisted of Murashige and Skoog salts, hereinafter MS salts, and vitamins (Murashige and Skoog, (1962) Physiol. Plant. 15: 473–497) 30 g/L sucrose, 100 mg/L myo-inositol, 30 g/L mannitol, 5 mg/L 6-benzylaminopurine, hereinafter BAP, 0.025 mg/L 2,4-D, 30 mg/L BASTA, and 2.5 g/L GELRITE (Schweizerhall) at pH 5.7. The cultures were placed in low light (125 ft-candles) for one week followed by one week in high light (325 ft-candles). Following a two week induction period, tissue was non-selectively transferred to hormone-free regeneration medium, which was identical to the induction medium except that it lacked 2,4-D and BAP, and was kept in high light. Small (1.5–3 cm) plantlets were removed and placed in 150×25 mm culture tubes containing SH medium (SH salts and vitamins (Schenk and Hildebrandt, (1972) Can. J. Bot. 50:199–204), 10 g/L sucrose, 100 mg/L myo-inositol, 5 mL/L FeEDTA, and 2.5 g/L GELRITE (Schweizerhall), pH 5.8). Plantlets were then transferred to 10 cm pots containing approximately 0.1 kg of METRO-MIX 360 (The Scotts Co. Marysville, Ohio) in the greenhouse as soon as they exhibited growth and developed a sufficient root system. They were grown with a 16 h photoperiod supplemented by a combination of high pressure sodium and metal halide lamps, and were watered as needed with a combination of three independent Peters Excel fertilizer formulations (Grace-Sierra Horticultural Products Company, Milpitas, Calif.). At the 3–5 leaf stage, plants were transferred to five gallon pots containing approximately 4 kg METRO-MIX 360. Primary regenerants were self- or sib-pollinated, or outcrossed to either elite inbreds or transgenic plants after an additional 6–10 weeks in the 5 gallon pots. $R_1$ seed was collected at 40–45 days post-pollination.

Embryogenic callus material containing the genes of interest was maintained as described herein. Continuous production of somatic embryos, which make up a large portion of embryogenic callus, was performed by transferring the callus tissue every two weeks. While the somatic embryos continued to proliferate, they usually remained in an early stage of embryo development because of the continued presence of 2,4-D in the culture medium. Somatic embryos could be regenerated into plantlets when callus was subjected to the regeneration procedure described-herein. During regeneration, somatic embryos formed roots and a shoot, subsequently ceasing development as an embryo.

Somatic embryos were made to develop as seed embryos by growing embryogenic callus on MS medium containing 6% (w/v) sucrose. The callus was grown for 7 days and then somatic embryos were individually transferred to MS medium with 6% sucrose and 10 $\mu$M abscisic acid, hereinafter ABA.

EXAMPLE 10

Southern Analysis of Transformed Callus and Plant Tissues

BASTA resistant lines transformed with various plasmids were characterized by Southern analysis to confirm the presence of the transgene using a DNA probe specific for the coding region of the gene of interest. DNA from leaf material was analyzed.

Leaf material from plants was harvested at the 6–8 leaf stage. Genomic DNA was prepared from lyophilized tissue as described by Saghai-Maroof et. al. ((1984) *Proceed. Nat. Acad. Sci. USA* 81:8014–8018). Eight μg of each DNA was digested with the restriction enzyme(s) specific for each plasmid construct using conditions suggested by the manufacturer (Bethesda Research Laboratory) and separated by electrophoresis on a 0.8% agarose gel. The DNA was then blotted onto nylon membranes as described by Southern ((1975) J. Mol. Biol., 98:503–517). The radioactive probe was then hybridized to the genomic DNA on the blots in 45 mL of minimal hybridization buffer [10% polyethylene glycol, 7% SDS, 0.6×SSC, 10 mM sodium phosphate, 5 mM EDTA and 100 μg/mL denatured salmon sperm DNA] overnight at 60° C. After hybridization, blots were washed at 60° C. in 0.25×SSC and 0.2% SDS for 45 min., blotted dry and exposed to XAR-5 film (Kodak) overnight on two intensifying screens (DuPont).

All lines analyzed showed at least one copy of the expected sized fragment indicating a complete copy of SCAb-TP1 gene.

EXAMPLE 11

SCAB-TP1 Expression in Maize

For RNA isolation, the tissue was pulverized using a Bessman Tissue Pulverizer (Spectrum Medical Industries, Houston, Tex.). RNA was extracted from the frozen powder using RNEASY Plant mini kits (Qiagen) according to the manufacturer's instructions. For expression analysis (Northern analysis), 5 μg RNA per sample was fractionated by electrophoresis in non-denaturing 10 mM $NaPO_4$ pH 6.8, 1.0% agarose gels. The volume of sample containing said RNA was dried using a SAVANT SpeedVac (Savant Instruments, Inc., Farmingdale, N.Y.), resuspended in 8 μL water, and denatured with an equal volume of 2×sample buffer (40 mM $NaHPO_4$, pH 6.8; 10 mM EDTA, 6% formaldehyde, 50% formamide) and heated to 68° C. for 15 minutes. The denatured sample was chilled on ice and 4 μL loading buffer (50% glycerol, 10 mM EDTA, 5 mM $NaPO_4$, 0.25% bromophenol blue) was added. The samples were loaded on the gel and electrophoresed for 3 h at 60 V in 10 mM phosphate buffer. RNA was transferred from the gel to GENESCREEN PLUS membrane (NEN Research Products, Boston, Mass.) by capillary transfer with sterile water as the transfer medium. Following transfer, the RNA was crosslinked to said membrane by UV (STRATALINKER, Stratagene Cloning Systems, Inc., La Jolla, Calif.).

The RNA blot was prehybridized for 3 h at 42° C. in hybridization buffer (50 mM sodium phosphate, pH 6.5, 0.8 M sodium chloride, 1 M EDTA, 0.2% sodium dodecyl sulfate, 0.05% bovine serum albumin, 0.05% Ficoll Type 40, 10% dextran sulfate). A hybridization probed specific for the antibody made against the.transit peptide was labelled with 50 μCi of α-$^{32}$P-dCTP (NEN Research Products) using READY-TO-GO labelling beads (Pharmacia, Piscataway, N.J.) according to the manufacturers instructions and purified over NUCTRAP columns (Stratagene). The labeled probe was denatured by boiling for 5 min, chilled on ice for 5 min, and added directly to the prehybridization blots. Hybridization was done in SEAL-A-MEAL bags (Dazey Corp., Industrial Airport, Kans.), at 42° C. for 16 h. Blots were washed 6 times for 0.5 h each in large excess of prewarmed washing solution (20 mM $NaPO_4$, pH 6.5, 50 mM NaCl, 1 mM EDTA, and 0.1% sodium dodecyl sulfate) at 60° C. The blot was exposed to a phosphor storage screen, scanned on a Molecular Dynamics Personal PHOSPHORIMAGER (Molecular Dynamics, Inc., Sunnyvale, Calif.) for analysis.

For analysis of $R_0$ plants, leaf tissue (~0.2 g) was harvested from plants transformed with pDAb439/TPE and pDAB439/TPnoE. RNA was extracted, fractionated, blotted to membranes and probed as described above. Lines that were positive for transgenic RNA at the callus stage were found to be positive at the R0 plants stage. These data indicated that the transgene was integrated and expressing mRNA related to the gene of interest.

To examine protein expression, SCAb-TP1 protein was purified from transformed maize callus tissue using the Qiagen Ni-NTA kit. Callus tissue (0.75–1.45 g) was ground with 400–600 μL 1xbinding buffer containing 1 mM Phenylmethylsulfonyl fluoride (PMSF) using a plastic tissue grinder and a small amount of sand. The lysate was then spun in a microfuge for 10 min to pellet cellular debris. The supernatant was filtered through a 0.2 μm syringe filter and applied to Ni-NTA spin column (Qiagen). The column was washed with 600 μL wash buffer and eluted with 400 μL elution buffer. The eluted material was then precipitated with acetone or concentrated with 3000 mw micro spin column (Amicon, Beverly, Mass.) and buffer exchanged with 10 mM phosphate. The concentrated protein was then run in 4–20% SDS-PAGE gels (Integrated Separation Systems, Natick, Mass.) and Western analysis were performed as described herein. A MRGS 6×HIS MAb preparation (Qiagen) was used as primary antibody. Detectable levels of SCAb-TP1 protein were observed in lines transformed with pDAB439/TPE and pDAB439/TPnoE.

EXAMPLE 12

Effect of SCAb-TP1 Expression on Endogenous Δ-9 Deaturase Levels in Transformed Maize The effects of SCAb-TP1 protein expression on endogenous levels of Δ-9 desaturase were examined using transformed maize callus tissues via Western analyses as described herein. Polyclonal antibodies immunologically reactive against mature Δ-9 desaturase were used as the primary antibody. Western data indicated that expression of SCAb-TP1 in callus tissue caused about 70% reduction in the levels of Δ-9 desaturase compared with control callus lines that were transformed with unrelated genes. Protein analysis on leaf tissues of $R_0$ plants also showed reduced levels (10 to 50%) of Δ-9 desaturase when compared to control lines. These data indicated a direct correlation between the presence and expression of the transgene and reduced Δ-9 desaturase levels (Table 1).

TABLE 1

Comparison of Δ-9 desaturase levels in maize lines transformed the pDAB439/TPE and pDAB439/TPnoE relative to control

| Line | SCAb-TP1 Protein | Reduced Δ-9 desaturase |
|---|---|---|
| TPE-04 | + | yes |
| TPE-05 | + | yes |
| TPE-06 | + | yes |
| TPE-07 | + | yes |
| TPE-08 | nd | yes |

TABLE 1-continued

Comparison of Δ-9 desaturase levels in maize lines transformed the pDAB439/TPE and pDAB439/TPnoE relative to control

| Line | SCAb-TP1 Protein | Reduced Δ-9 desaturase |
|---|---|---|
| TPE-09 | + | yes |
| TPE-10 | + | yes |
| TPnoE-01 | nd | yes |
| TPnoE-04 | nd | yes |
| TPnoE-05 | + | yes |
| TPnoE-07 | + | yes |
| TPnoE-11 | + | yes |
| TPnoE-12 | nd | yes |

nd: not determined

Fertile plants containing pDAB463/TPnoE were crossed with inbred CQ715 HO-I (Mycogen Seeds, San Diego, Calif.) as pollen donors and seed were obtained. These seed were planted and molecular analyses were performed on leaf samples to determine the presence of SCAB-TP1 gene, SCAB-TP1 protein and their effect on Δ-9 desaturase levels. Reduction in Δ9-desaturase levels (40–70%) was found to correlated with the presence of the transgene and SCAB-TP1 expressed therefrom.

EXAMPLE 13

Antibody-Mediated Down-Regulation of Maize Palmitoyl-ACP Thioesterase (PTE)

Antibodies directed against the chloroplast transit peptide domain of the PTE protein are used in this example to block import of PTE into the chloroplast where early steps of fatty acid biosynthesis occur.

A. Analysis of PTE Transit Peptides from Various Maize Genotypes

Successful application of antibody mediated downregulation requires that the amino acid sequence of the transit peptide be highly conserved between the maize lines used for transformation and regeneration in the laboratory, and the elite maize lines into which the genes will be introgressed for commercial development. DNA sequences encoding the transit peptide domain of PTE were amplified from eight different corn varieties: CS608, CQ806, HO1, HiII, OQ414, HO601, 2XH753 and 2XH755. The deduced protein sequences were almost identical among all lines, differing only by the absence of one or two amino acids of the 90 amino acids which comprise the transit peptide. These theoretical amino acid sequences were used to design a region for antibody targeting.

B. Design of Antibodies Targeted to the Maize PTE Transit Peptide

The amino acid sequence of PTE precursor protein from maize line CS608 was analyzed to identify a region on the transit peptide portion that exhibits high antigenicity and surface probability. A sequence (PGSPAPAAPKNGLGERPESLDVRG)(SEQ ID NO:56) extending from amino acid residue number 12 to 35 was selected. The sequence information was sent to Zymed Laboratories Inc. for peptide synthesis and polyclonal antibody production in two rabbits.

C. Baculovirus Expression of PTE Precursor Protein

The gene coding for PTE precursor (including signal peptide) was cloned into the baculovirus transfer vector pAcSG2 (PharMingen, San Diego, Calif.). A cotransfection was performed in a 6-well plate with $6\times10^5$Sf9 cells/well. BacPAK6 linear DNA (Clontech, Palo Alto, Calif.) was used as parental DNA in the cotransfection. Bacfectin reagent was used to facilitate cotransfection (included with BacPAK6 DNA). Transfection media was harvested at 3 and 6 days post-transfection. Sf9 cells ($6\times10^5$ cells/well) were infected with 100 μl transfection media. After 3 days, cells were harvested and western blots were performed. Blots were probed with rabbit polyclonal antibody generated against the mature PTE protein or to the transit peptide of the precursor protein (rabbit 1 or rabbit 2). The blot probed with antibody to the mature protein showed 2 distinct bands for PTE with or without the transit peptide. Blots probed with antibody to the transit peptide only detected the higher molecular weight form of the PTE containing the transit peptide.

Production of hybridoma cell lines that produce antibodies that bind to the PTE precursor protein, cloning of the antibody genes and single chain antibody gene, and transformation into corn can be carried out as described in foregoing Examples 5 through 9.

What is claimed is:

1. A plant cell in which the steady-state level of maize stearoyl-ACP Δ-9 desaturase is down-regulated, comprising a nucleic acid construct which comprises in the 5' to 3' direction of transcription a promoter functional in a plant cell, SEQ ID NO:31, and a termination region functional in a plant cell wherein said construct expresses SEQ ID NO:32 in said plant cell such that SEQ ID NO:32 binds to maize stearoyl-ACP Δ-9 desaturase transit peptide resulting in the down-regulation of the steady-state level of maize stearoyl-ACP Δ-9 desaturase in said plant cell.

2. The nucleic acid construct of claim 1.

3. A plant or progeny thereof obtained from the plant cell of claim 1, wherein said plant or progeny comprises said nucleic acid construct.

* * * * *